(12) United States Patent
Hornberger et al.

(10) Patent No.: US 9,745,289 B2
(45) Date of Patent: Aug. 29, 2017

(54) ALDOSTERONE SYNTHASE INHIBITORS

(71) Applicant: Boehringer Ingelheim International GmbH, Ingelheim am Rhein (DE)

(72) Inventors: Keith R. Hornberger, Southbury, CT (US); Kenneth Michael Meyers, Seymour, CT (US); Peter Allen Nemoto, Southbury, CT (US); Simon Surprenant, New Milford, CT (US); Hui Yu, New Milford, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/882,486

(22) Filed: Oct. 14, 2015

(65) Prior Publication Data

US 2016/0108026 A1    Apr. 21, 2016

Related U.S. Application Data

(60) Provisional application No. 62/064,234, filed on Oct. 15, 2014.

(51) Int. Cl.
| | |
|---|---|
| *C07D 405/04* | (2006.01) |
| *C07D 417/14* | (2006.01) |
| *C07D 413/14* | (2006.01) |
| *C07D 405/14* | (2006.01) |

(52) U.S. Cl.
CPC ......... *C07D 405/14* (2013.01); *C07D 405/04* (2013.01); *C07D 413/14* (2013.01); *C07D 417/14* (2013.01)

(58) Field of Classification Search
CPC .. C07D 413/14; C07D 417/14; C07D 405/14; C07D 405/04
USPC ....................................... 546/268.1
See application file for complete search history.

(56) References Cited

U.S. PATENT DOCUMENTS

| | | | | |
|---|---|---|---|---|
| 9,181,272 B2 * | 11/2015 | Balestra | ............... | C07D 471/04 |
| 9,334,285 B2 * | 5/2016 | Burke | ............... | C07D 491/052 |
| 2010/0292225 A1 | 11/2010 | Chamoin et al. | | |
| 2013/0143863 A1 * | 6/2013 | Aebi | ............... | C07D 401/04 |
| | | | | 514/210.18 |
| 2014/0323468 A1 * | 10/2014 | Balestra | ............... | C07D 471/04 |
| | | | | 514/211.1 |
| 2016/0024105 A1 * | 1/2016 | Burke | ............... | C07D 491/052 |
| | | | | 514/312 |

FOREIGN PATENT DOCUMENTS

| | | |
|---|---|---|
| WO | 2010042477 A1 | 4/2010 |
| WO | 2014055595 A1 | 4/2014 |
| WO | 2014130608 A1 | 8/2014 |
| WO | WO 2014130608 * | 8/2014 |

OTHER PUBLICATIONS

Hu; J. Med. Chem. 2014, 57, 5011-5022.*
Heim; Journal of Medicinal Chemistry 2008, 51, 5064-5074.*
Azizi; Nephrol Dial Transplant 2013, 28, 36-43.*
Banki; PLoS One 2012, 7, e39938.*
Andersen; Curr Hypertens Rep,2013, 15, 484-488.*
Hargovan; Journal of the Royal Society of Medicine Cardiovascular Disease 2014, 0, 1-9.*
Dorrance; F1000Prime Reports 2014, 6-61.*
International Search Report, Mailed Feb. 16, 2016, PCT/ISA220, for PCT/US2015055421.
Lucas, J. Med. Chem., vol. 51, "In Vivo Active aldosterone synthase inhibitors with improved selectivity: Lead optimization providing a series of Pyridine substituted 3,4 Dihydro-1H quinolin-2-one derivatives", 2008.

* cited by examiner

*Primary Examiner* — Noble Jarrell
*Assistant Examiner* — Daniel Carcanague
(74) *Attorney, Agent, or Firm* — Paula K. Wittmayer; David L. Kershner

(57) ABSTRACT

The present invention relates to compounds of formula I:

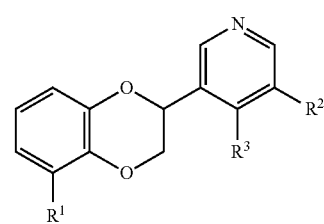

and pharmaceutically acceptable salts thereof, wherein $R^1$, $R^2$ and $R^3$, are as defined herein. The invention also relates to pharmaceutical compositions comprising these compounds, methods of using these compounds in the treatment of various diseases and disorders, processes for preparing these compounds and intermediates useful in these processes.

32 Claims, No Drawings

ALDOSTERONE SYNTHASE INHIBITORS

FIELD OF THE INVENTION

This invention relates to heteroaryl compounds that are useful as inhibitors of aldosterone synthase (CYP11B2) and are thus useful for treating a variety of diseases that are mediated or sustained by aldosterone activity, including renal disease, diabetic nephropathy, cardiovascular diseases and fibrotic disorders. This invention also relates to pharmaceutical compositions comprising these compounds, methods of using these compounds in the treatment of various diseases and disorders, processes for preparing these compounds and intermediates useful in these processes.

BACKGROUND

Aldosterone is a steroid hormone having mineralcorticoid activity. It is produced primarily by the adrenal glomerulosa in response to angiotensin II, adrenocorticotropic hormone and increased serum potassium levels. A primary physiological role of aldosterone in the kidney is to maintain sodium and potassium balance by regulating cation exchange ($Na^+$ reabsorption and $K^+$ secretion) in the distal nephron. However, aldosterone has also been shown to be a pro-inflammatory and profibrotic hormone in blood vessels, heart and kidneys. The effects of aldosterone on gene expression are mediated via binding to the mineralocorticoid receptor (MR) and a canonical nuclear hormone receptor pathway. However, the hormone also elicits rapid, non-genomic responses, including acute regulation of the activity of tubular ion transporters, for example $Na^+/H^+$ exchangers (NHEs), $H^+$-ATPase, ENaC, and $Na^+/K^+$ ATPase (D. W. Good, 2007, Hypertension, 49, 728-739). It is likely that some of these effects are mediated by MR-independent pathways. Conversely, the MR can bind alternative ligands, including deoxycorticosterone, corticosterone, cortisol and progesterone. Thus, inhibition of aldosterone synthesis is predicted to have a pharmacodynamic profile distinct from what is observed with MR antagonists.

Aldosterone is synthesized in the zona glomerulosa of the adrenal glands, where a single enzyme, CYP11B2 (aldosterone synthase), catalyzes the 3-step conversion of 11-deoxycorticosterone (11-DOC) to aldosterone, via corticosterone and 18-hydroxycorticosterone. Adrenal aldosterone synthase activity is regulated by Angiotensin II and K+ levels and unidentified adipocyte-derived mediators. Low levels of aldosterone synthase have also been detected in the heart and CNS, though the physiological relevance is uncertain, perhaps relating to paracrine effects. Systemic aldosterone is believed to derive essentially entirely from the adrenals.

Beyond its role in regulating sodium and potassium balance, aldosterone has been shown to have pro-inflammatory and pro-fibrotic actions in multiple tissues including the kidney, blood vessels and the heart. The harmful effects of inappropriate aldosterone levels on blood pressure and cardiac, renal, cerebral and vascular function and structure, have been widely reported in the literature, including: i) increase in sodium retention through $Na^+/K^+$ ATPase pump induction in distal tubules resulting in volume expansion and high blood pressure, ii) endothelial dysfunction, iii) oxidative stress, iv) renal and cardiac hypertrophy, v) fibroblast proliferation, and, vi) excessive synthesis of extracellular matrix resulting in renal, cardiac and vascular fibrosis.

Benefits of aldosterone blockade/inhibition include reduction of kidney fibrosis and improvement of glomerular filtration rate and albuminuria in models of chronic kidney disease (CKD) and diabetic nephropathy. This is supported by pre-clinical data (for example, Fiebler et al., 2005, Circulation, 111, 3087-3094; Lea et al., 2009, Kidney International, 75, 936-945). Other benefits reported in the literature include decreased blood pressure and end-organ damage (heart, kidney, vessels) in both renin-dependent and salt-sensitive hypertension.

Although many of aldosterone's known effects are mediated through mineralcorticoid receptor (MR) activation, and much of the evidence favoring targeting this pathway comes from experiments with MR antagonists, non-MR mediated effects are reported and knockout mice for MR and aldosterone synthase exhibit different phenotypes (Makhanova et al. 2006, Berger et al. 1998, Funder 2007). These observations further suggest that aldosterone synthase inhibitors may have a different profile and offer advantages compared to MR antagonists.

For example, several aldosterone actions are not inhibited by MR antagonists, including the potentially deleterious effects on the vasculature (increased peripheral vascular resistance), the heart (effects on myocardial re-polarization) and the endocrine system (decreased insulin secretion). Furthermore, MR antagonism leads to an increase in circulating aldosterone, predicted to increase aldosterone signaling via non-MR pathways and, potentially, partially overcoming the MR blockade itself.

Current therapeutic strategies focus on slowing progression and treating conditions underlying diabetic nephropathy: control of blood glucose and control of high blood pressure. Angiotensin converting enzyme (ACE) inhibitors and angiotensin receptor blockers (ARB) have shown renal benefit in diabetic patients. To date, representatives of the ACE inhibitor class and from the ARB class have been approved for the treatment of diabetic nephropathy. These therapies represent limited benefit for the diabetic nephropathy patients.

Although the use of ACE inhibitors and ARBs represents the current standard of care for patients with diabetic nephropathy, patients progressively lose kidney function while on these medications, as seen in the IDNT (E. J. Lewis et al., 2001, N. Engl. J. Med., 345, 851-860) and RENAAL (B. M. Brenner et al., 2001, N. Engl. J. Med., 345, 861-869) studies, which reported a decrease over time in estimated glomerular filtration rate, which is an accurate measure of chronic kidney disease progression in patients treated by these conventional methods. At stage 5 chronic kidney disease, renal replacement therapy is required, in the form of either dialysis or transplant.

Aldosterone synthase inhibition may also be predicted to offer advantages as add-on therapy with ACE inhibitors and ARBs. Notably, 25-50% of patients receiving these agents experience "aldosterone breakthrough" in which aldosterone levels initially lowered by these treatments eventually return to pretreatment levels. This phenomenon would not occur with direct aldosterone synthase inhibition and could enhance efficacy in combination therapy.

There remains a high unmet medical need to treat diabetic nephropathy, to halt or regress disease progression by specifically targeting the underlying pathophysiological mechanisms associated with chronic inflammation and fibrosis, irrespective of the original cause of the disease and when co-administered with current therapies. The studies described above and in the literature provide evidence that inhibitors of aldosterone synthesis will be useful for the treatment of diabetic kidney disease including diabetic nephropathy; non-diabetic kidney disease including glomerulosclerosis, glomerulonephritis, IGA nephropathy, nephritic syndrome and focal segmental glomerulosclerosis (FSGS); cardiovascular diseases including hypertension, pulmonary arterial hypertension, Conn's syndrome, systolic heart failure, diastolic heart failure, left ventricular dysfunction, left ventricular stiffness and fibrosis, left ventricular filing abnormalities, arterial stiffness, atherosclerosis and cardiovascular morbidity associated with primary or secondary hyperaldosteronism; adrenal hyperplasia and primary and secondary hyperaldosteronism.

BRIEF SUMMARY OF THE INVENTION

The present invention provides novel compounds that inhibit aldosterone synthase and thus useful for treating a variety of diseases and disorders that can be alleviated by lowering levels of aldosterone including renal disease, diabetic nephropathy, cardiovascular diseases and fibrotic disorders. This invention also relates to pharmaceutical compositions comprising these compounds, methods of using these compounds in the treatment of various diseases and disorders, processes for preparing these compounds and intermediates useful in these processes.

DETAILED DESCRIPTION OF THE INVENTION

In an embodiment of the invention, there are provided compounds of the formula I

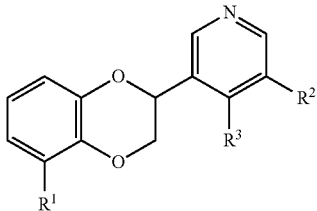

wherein:
$R^1$ is selected from —C(O)NH$_2$, —C(O)NH(CH$_3$) and —CN;
$R^2$ is —(X)—$R^4$, wherein
—(X)— is a bond, —CH$_2$—, or —O—; and
$R^4$ is selected from
—H;
$C_{1-3}$alkyl, optionally substituted with one to four groups selected from —F, —OH, and —SO$_2$C$_{1-3}$alkyl;
halogen;
—CN;
—SO$_2$C$_{1-3}$ alkyl;
—C(O)N(C$_{1-3}$alkyl)$_2$;
—NHC(O)R$^5$ or —N(CH$_3$)C(O)R$^5$, provided that —(X)— is —CH$_2$— and wherein R$^5$ is selected from C$_{3-6}$cycloalkyl and C$_{1-3}$alkyl optionally substituted with one to three —F groups;
—NHSO$_2$C$_{1-3}$alkyl;
—CH(cyclopropyl)NHSO$_2$C$_{1-3}$ alkyl;
—OCH$_2$C(O)N(C$_{1-3}$alkyl)$_2$, provided that —(X)— is —CH$_2$—;
—S(=O)(=NH)CH$_3$, provided that —(X)— is —CH$_2$—;
heterocyclyl selected from tetrahydropyranyl, tetrahydrofuranyl, pyrrolidinyl, 1,1-dioxo[1,2]-thiazine, morpholinyl, oxazolidinyl, piperidinyl, azetidinyl, wherein said heterocyclyl is optionally substituted with one to three groups selected from —C(O)C$_{1-3}$alkyl, halogen, —OH, oxo and C$_{1-3}$ alkyl;
—C(O)-heterocyclyl, provided that —(X)— is —CH$_2$, wherein said heterocyclyl is selected from morpholin-4-yl, pyrrolidin-1-yl and piperidin-1-yl, optionally substituted with one or two groups selected from —F and —OH;
$C_{3-6}$cycloalkyl optionally substituted with —CN or —OH; and
phenyl, optionally substituted with —SO$_2$NH$_2$; and
$R^3$ is H, or C$_{1-3}$alkyl optionally substituted with —OH; or
$R^2$ and $R^3$ together form an annelated five-membered cycloalkyl ring optionally substituted with —OH;
or a salt or a stereoisomer thereof.

In another embodiment, there are provided compounds of the formula I as described according to the embodiment above and wherein
$R^1$ is —C(O)NH$_2$ or —CN;
$R^2$ is —(X)—$R^4$, wherein
—(X)— is a bond, and
$R^4$ is selected from
—CH$_3$;
—CF$_3$;
—CHF$_2$;
—CH$_2$OH;
—CH(OH)CH$_3$;
—CH(OH)CF$_3$;
—F;
—CN;
heterocyclyl selected from tetrahydropyranyl and pyrrolidinyl, wherein said heterocyclyl is optionally substituted with one to three groups selected from C$_{1-3}$alkyl, halogen, —OH and oxo;
$C_{3-6}$cycloalkyl optionally substituted with —CN or —OH; and phenyl, optionally substituted with —SO$_2$NH$_2$; or
—(X)— is O, and
$R^4$ is selected from
$C_{1-3}$alkyl;
—CH$_2$SO$_2$C$_{1-3}$alkyl; and
heterocyclyl selected from tetrahydropyranyl, tetrahydrofuranyl, pyrrolidinyl, piperidinyl, and azetidinyl, wherein said heterocyclyl is optionally substituted with one to three groups selected from —C(O)C$_{1-3}$alkyl, halogen, —OH, oxo and C$_{1-3}$alkyl; or
X is (—CH$_2$—), and
$R^4$ is selected from
—SO$_2$C$_{1-3}$alkyl;
—C(O)N(C$_{1-3}$alkyl)$_2$;
—NHC(O)R$^5$ or —N(CH$_3$)C(O)R$^5$, wherein R$^5$ is selected from cyclopropyl and C$_{1-3}$alkyl optionally substituted with one to three —F groups;
—OCH$_2$C(O)N(C$_{1-3}$alkyl)$_2$;
—NHSO$_2$C$_{1-3}$alkyl;
—S(=O)(=NH)CH$_3$;
heterocyclyl selected from pyrrolidinyl, 1,1-dioxo[1,2]-thiazine, morpholinyl and oxazolidinyl, wherein said heterocyclyl is optionally substituted with one to three groups selected from —C(O)C$_{1-3}$alkyl, halogen, —OH, oxo and C$_{1-3}$alkyl; and
—C(O)-heterocyclyl, wherein the heterocyclyl is selected from morpholin-4-yl, pyrrolidin-1-yl and piperidin-1-yl, optionally substituted with one or two groups selected from —F and —OH; and
$R^3$ is H or C$_{1-3}$alkyl optionally substituted with —OH;
or a salt or a stereoisomer thereof.

In another embodiment, there are provided compounds of the formula I as described according to any of the embodiments above and wherein
$R^2$ is —(X)—$R^4$, wherein
—(X)— is a bond, and
$R^4$ is selected from
—$CF_3$;
—$CHF_2$;
—$CH_2OH$;
—$CH(OH)CH_3$;
—$CH(OH)CF_3$;
—F;
—CN;
heterocyclyl selected from tetrahydropyranyl and pyrrolidinyl, wherein said heterocyclyl is substituted with one to three groups selected from $C_{1-3}$alkyl, —F, —OH and oxo;
$C_{3-6}$cycloalkyl, substituted with —CN or —OH; and
phenyl, optionally substituted with —$SO_2NH_2$; and
$R^3$ is H, or $C_{1-3}$alkyl optionally substituted with —OH;
or a salt or a stereoisomer thereof.

In another embodiment, there are provided compounds of the formula I as described according to any of the embodiments above and wherein
$R^2$ is —(X)—$R^4$, wherein
—(X)— is O, and
$R^4$ is selected from
$C_{1-3}$alkyl;
—$CH_2SO_2C_{1-3}$alkyl; and
heterocyclyl selected from tetrahydropyranyl, tetrahydrofuranyl, pyrrolidinyl, piperidinyl, and azetidinyl, wherein said heterocyclyl is optionally substituted with —C(O)$C_{1-3}$alkyl; and
$R^3$ is H, or $C_{1-3}$alkyl optionally substituted with —OH;
or a salt or a stereoisomer thereof.

In another embodiment, there are provided compounds of the formula I as described according to any of the embodiments above and wherein
$R^2$ is —(X)—$R^4$, wherein
X is (—$CH_2$—), and
$R^4$ is selected from
—$SO_2C_{1-3}$alkyl
—C(O)N($C_{1-3}$alkyl)$_2$;
—NHC(O)$R^5$ or —N(CH$_3$)C(O)$R^5$, wherein $R^5$ is selected from cyclopropyl and $C_{1-3}$alkyl optionally substituted with one to three —F groups;
—OCH$_2$C(O)N($C_{1-3}$alkyl)$_2$;
—NHSO$_2C_{1-3}$alkyl;
—S(=O)(=NH)CH$_3$;
heterocyclyl selected from pyrrolidinyl, 1,1-dioxo[1,2]-thiazine, morpholinyl and oxazolidinyl, wherein said heterocyclyl is optionally substituted with one to two groups selected from oxo and $C_{1-3}$alkyl; and
—C(O)-heterocyclyl, wherein the heterocyclyl is selected from morpholin-4-yl, pyrrolidin-1-yl and piperidin-1-yl, optionally substituted with one or two groups selected from —F and —OH; and
$R^3$ is H, or $C_{1-3}$alkyl optionally substituted with —OH;
or a salt or a stereoisomer thereof.

In another embodiment, there are provided compounds of the formula I as described according to any of the embodiments above and wherein
$R^1$ is —C(O)NH$_2$;
or a salt or a stereoisomer thereof.

In another embodiment, there are provided compounds of the formula I as described according to any of the embodiments above and wherein
$R^1$ is —CN;
or a salt or a stereoisomer thereof.

In another aspect of the invention, there is provided a compound of the general formula I or a stereoisomer or pharmaceutically acceptable salt thereof for use in a therapeutic method as described hereinbefore and hereinafter.

Table 1 shows representative compounds of the invention which can be made by the methods described in the general synthetic schemes, the examples, and known methods in the art.

TABLE 1

| Cpd | Structure | Name |
|---|---|---|
| 1 | 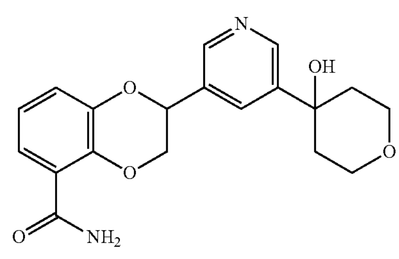 [SMILES: NC(=O)c1cccc2c1OCC(c1cncc(C3(O)CCOCC3)c1)O2] | 2-[5-(4-Hydroxy-tetrahydro-pyran-4-yl)-pyridin-3-yl]-2,3-dihydro-benzo[1,4]dioxine-5-carboxylic acid amide |
| 2 | 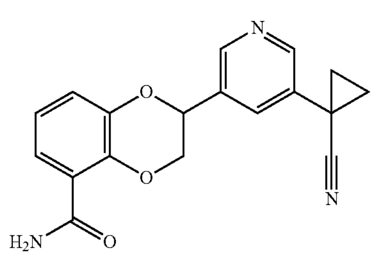 [SMILES: N#CC1(c2cncc(C3COc4c(cccc4C(N)=O)O3)c2)CC1] | 2-[5-(1-Cyano-cyclopropyl)-pyridin-3-yl]-2,3-dihydro-benzo[1,4]dioxine-5-carboxylic acid amide |

TABLE 1-continued

| Cpd | Structure | Name |
|---|---|---|
| 3 | 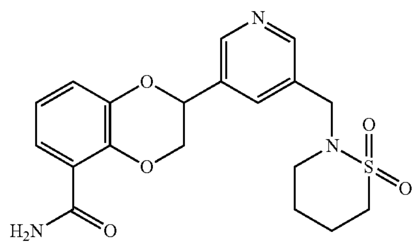 [SMILES: NC(=O)c1cccc2c1OCC(c1cncc(CN3CCCCS3(=O)=O)c1)O2] | 2-[5-(1,1-Dioxo-1$\lambda^6$,-[1,2]thiazinan-2-ylmethyl)-pyridin-3-yl]-2,3-dihydro-benzo[1,4]dioxine-5-carboxylic acid amide |
| 4 | 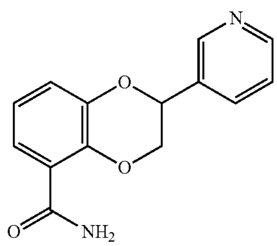 [SMILES: NC(=O)c1cccc2c1OCC(c1cccnc1)O2] | 2-Pyridin-3-yl-2,3-dihydro-benzo[1,4]dioxine-5-carboxylic acid amide |
| 5 | 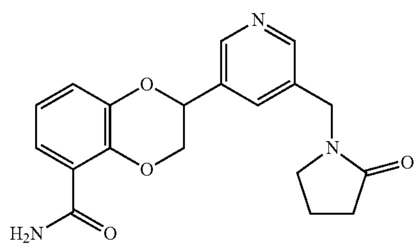 [SMILES: NC(=O)c1cccc2c1OCC(c1cncc(CN3CCCC3=O)c1)O2] | 2-[5-(2-Oxo-pyrrolidin-1-ylmethyl)-pyridin-3-yl]-2,3-dihydro-benzo[1,4]dioxine-5-carboxylic acid amide |
| 6 | 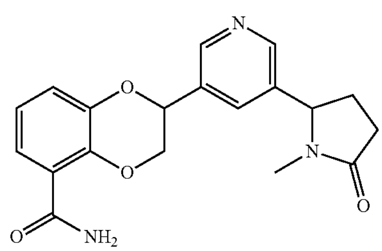 [SMILES: CN1C(=O)CCC1c1cncc(C2COc3c(cccc3C(N)=O)O2)c1] | 2-[5-(-1-Methyl-5-oxo-pyrrolidin-2-yl)-pyridin-3-yl]-2,3-dihydro-benzo[1,4]dioxine-5-carboxylic acid amide |
| 7 | 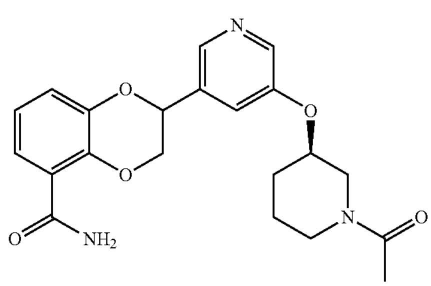 [SMILES: CC(=O)N1CCC[C@@H](Oc2cncc(C3COc4c(cccc4C(N)=O)O3)c2)C1] | 2-[5-((R)-1-Acetyl-piperidin-3-yloxy)-pyridin-3-yl]-2,3-dihydro-benzo[1,4]dioxine-5-carboxylic acid amide |
| 8 | 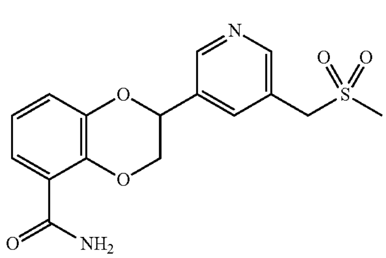 [SMILES: CS(=O)(=O)Cc1cncc(C2COc3c(cccc3C(N)=O)O2)c1] | 2-(5-Methanesulfonylmethyl-pyridin-3-yl)-2,3-dihydro-benzo[1,4]dioxine-5-carboxylic acid amide |

TABLE 1-continued

| Cpd | Structure | Name |
|---|---|---|
| 9 | 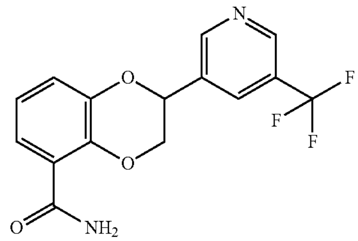 [SMILES: NC(=O)c1cccc2c1OCC(c1cncc(C(F)(F)F)c1)O2] | 2-(5-Trifluoromethyl-pyridin-3-yl)-2,3-dihydro-benzo[1,4]dioxine-5-carboxylic acid amide |
| 10 | 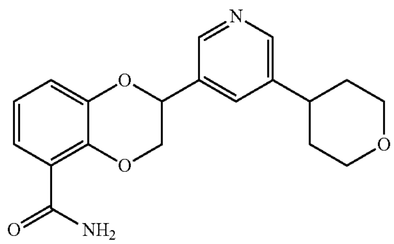 [SMILES: NC(=O)c1cccc2c1OCC(c1cncc(C3CCOCC3)c1)O2] | 2-[5-(Tetrahydro-pyran-4-yl)-pyridin-3-yl]-2,3-dihydro-benzo[1,4]dioxine-5-carboxylic acid amide |
| 11 | 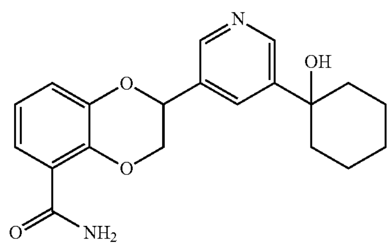 [SMILES: NC(=O)c1cccc2c1OCC(c1cncc(C3(O)CCCCC3)c1)O2] | 2-[5-(1-Hydroxy-cyclohexyl)-pyridin-3-yl]-2,3-dihydro-benzo[1,4]dioxine-5-carboxylic acid amide |
| 12 | 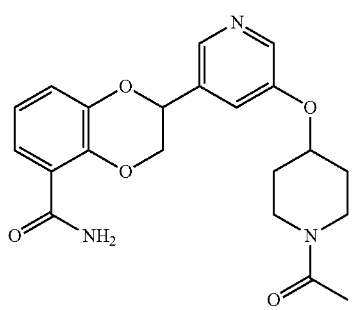 [SMILES: CC(=O)N1CCC(Oc2cncc(C3COc4c(cccc4C(N)=O)O3)c2)CC1] | 2-[5-(1-Acetyl-piperidin-4-yloxy)-pyridin-3-yl]-2,3-dihydro-benzo[1,4]dioxine-5-carboxylic acid amide |
| 13 | 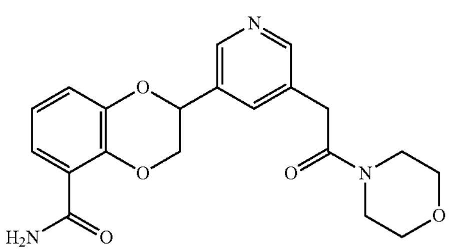 [SMILES: NC(=O)c1cccc2c1OCC(c1cncc(CC(=O)N3CCOCC3)c1)O2] | 2-[5-(2-Morpholin-4-yl-2-oxo-ethyl)-pyridin-3-yl]-2,3-dihydro-benzo[1,4]dioxine-5-carboxylic acid amide |
| 14 | 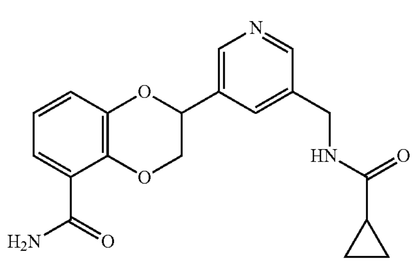 [SMILES: NC(=O)c1cccc2c1OCC(c1cncc(CNC(=O)C3CC3)c1)O2] | 2-{5-[(Cyclopropanecarbonyl-amino)-methyl]-pyridin-3-yl}-2,3-dihydro-benzo[1,4]dioxine-5-carboxylic acid amide. |

TABLE 1-continued

| Cpd | Structure | Name |
|---|---|---|
| 15 | 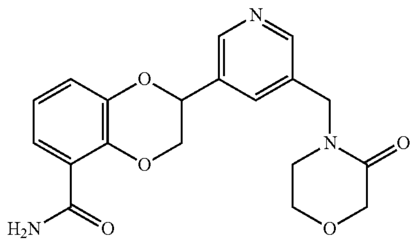 [SMILES: NC(=O)c1cccc2c1OCC(c1cncc(CN3CCOCC3=O)c1)O2] | 2-[5-(3-Oxo-morpholin-4-ylmethyl)-pyridin-3-yl]-2,3-dihydro-benzo[1,4]dioxine-5-carboxylic acid amide |
| 16 | 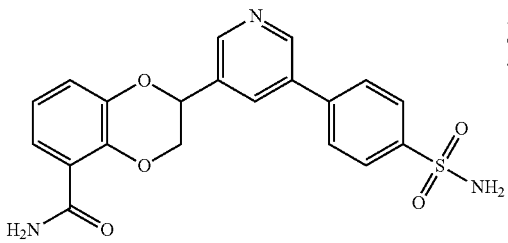 | 2-[5-(4-Sulfamoyl-phenyl)-pyridin-3-yl]-2,3-dihydro-benzo[1,4]dioxine-5-carboxylic acid amide |
| 17 | 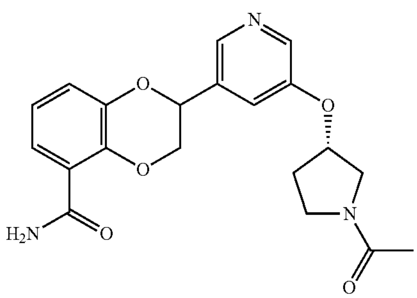 [SMILES: CC(=O)N1CC[C@H](Oc2cncc(C3COc4c(cccc4C(N)=O)O3)c2)C1] | 2-[5-((S)-1-Acetyl-pyrrolidin-3-yloxy)-pyridin-3-yl]-2,3-dihydro-benzo[1,4]dioxine-5-carboxylic acid amide |
| 18 | 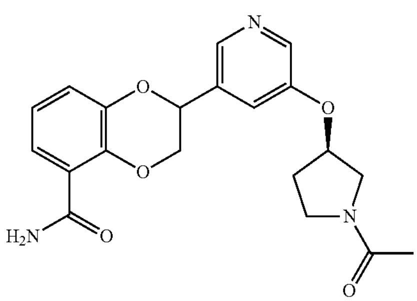 [SMILES: CC(=O)N1CC[C@@H](Oc2cncc(C3COc4c(cccc4C(N)=O)O3)c2)C1] | 2-[5-((R)-1-Acetyl-pyrrolidin-3-yloxy)-pyridin-3-yl]-2,3-dihydro-benzo[1,4]dioxine-5-carboxylic acid amide |
| 19 | 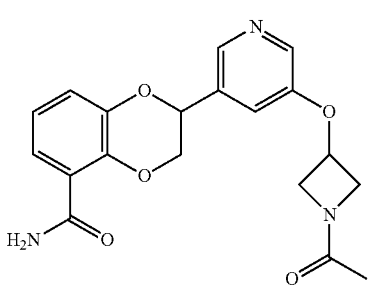 [SMILES: CC(=O)N1CC(Oc2cncc(C3COc4c(cccc4C(N)=O)O3)c2)C1] | 2-[5-(1-Acetyl-azetidin-3-yloxy)-pyridin-3-yl]-2,3-dihydro-benzo[1,4]dioxine-5-carboxylic acid amide |

TABLE 1-continued

| Cpd | Structure | Name |
|---|---|---|
| 20 | 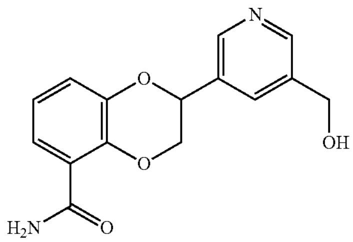 [SMILES: NC(=O)c1cccc2c1OCC(c1cncc(CO)c1)O2] | 2-(5-Hydroxymethyl-pyridin-3-yl)-2,3-dihydro-benzo[1,4]dioxine-5-carboxylic acid amide |
| 21 | 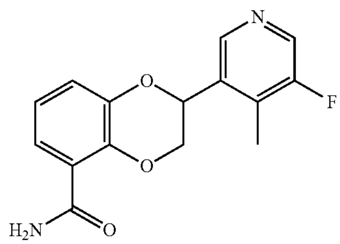 [SMILES: Cc1c(F)cncc1C1COc2c(cccc2C(N)=O)O1] | 2-(5-Fluoro-4-methyl-pyridin-3-yl)-2,3-dihydro-benzo[1,4]dioxine-5-carboxylic acid amide |
| 22 | 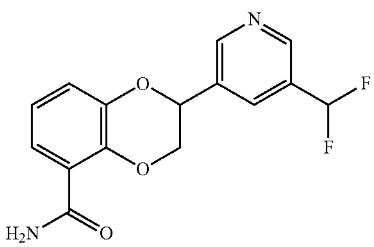 [SMILES: NC(=O)c1cccc2c1OCC(c1cncc(C(F)F)c1)O2] | 2-(5-Difluoromethyl-pyridin-3-yl)-2,3-dihydro-benzo[1,4]dioxlne-5-carboxylic acid amide |
| 23 | 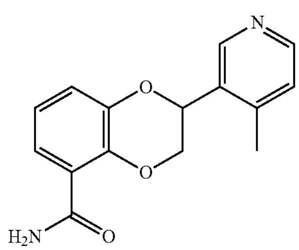 [SMILES: Cc1ccncc1C1COc2c(cccc2C(N)=O)O1] | 2-(4-Methyl-pyridin-3-yl)-2,3-dihydro-benzo[1,4]dioxine-5-carboxylic acid amide |
| 24 | 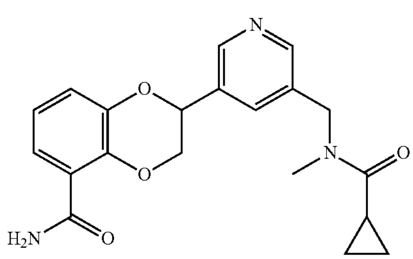 [SMILES: CN(Cc1cncc(C2COc3c(cccc3C(N)=O)O2)c1)C(=O)C1CC1] | 2-{5-[(Cyclopropanecarbonyl-methyl-amino)-methyl]-pyridin-3-yl}-2,3-dihydro-benzo[1,4]dioxine-5-carboxylic acid amide |
| 25 | 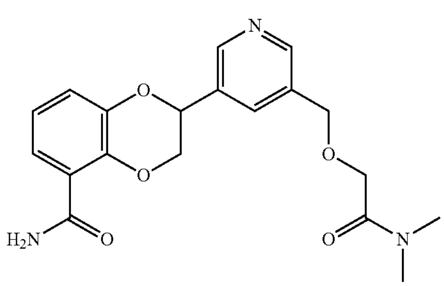 [SMILES: CN(C)C(=O)COCc1cncc(C2COc3c(cccc3C(N)=O)O2)c1] | 2-(5-Dimethylcarbamoylmethoxymethyl-pyridin-3-yl)-2,3-dihydro-benzo[1,4]dioxine-5-carboxylic acid amide |

TABLE 1-continued

| Cpd | Structure | Name |
|---|---|---|
| 26 | 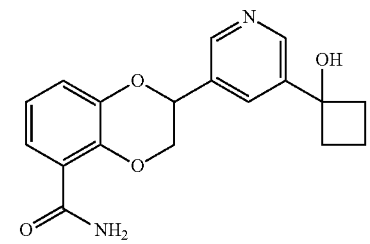 [SMILES: NC(=O)c1cccc2c1OCC(c1cncc(C3(O)CCC3)c1)O2] | 2-[5-(1-Hydroxy-cyclobutyl)-pyridin-3-yl]-2,3-dihydro-benzo[1,4]dioxine-5-carboxylic acid amide |
| 27 | 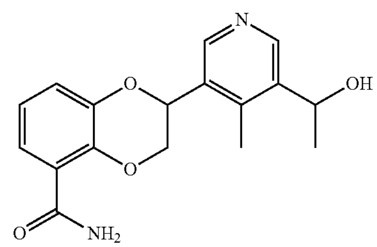 [SMILES: Cc1c(C(C)O)cncc1C1COc2c(cccc2C(N)=O)O1] | 2-[5-(1-Hydroxy-ethyl)-4-methyl-pyridin-3-yl]-2,3-dihydro-benzo[1,4]dioxine-5-carboxylic acid amide |
| 28 | 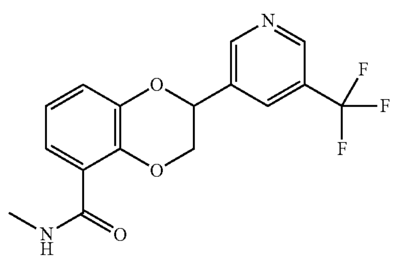 [SMILES: CNC(=O)c1cccc2c1OCC(c1cncc(C(F)(F)F)c1)O2] | 2-(5-Trifluoromethyl-pyridin-3-yl)-2,3-dihydro-benzo[1,4]dioxine-5-carboxylic acid methylamide |
| 29 | 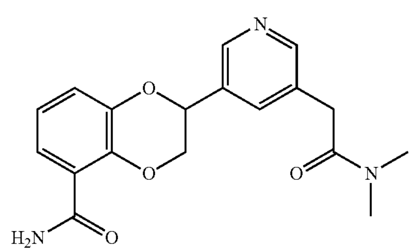 [SMILES: CN(C)C(=O)Cc1cncc(C2COc3c(cccc3C(N)=O)O2)c1] | 2-[5-[2-(Dimethylamino)-2-oxo-ethyl]-3-pyridyl]-2,3-dihydro-1,4-benzodioxine-5-carboxamide |
| 30 | 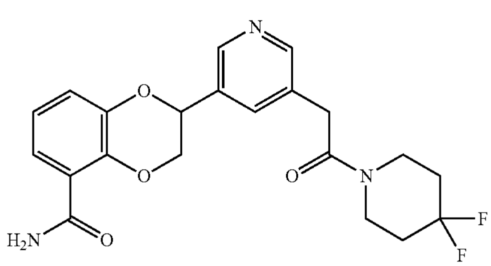 [SMILES: NC(=O)c1cccc2c1OCC(c1cncc(CC(=O)N3CCC(F)(F)CC3)c1)O2] | 2-{5-[2-(4,4-Difluoro-piperidin-1-yl)-2-oxo-ethyl]-pyridin-3-yl}-2,3-dihydro-benzo[1,4]dioxine-5-carboxylic acid amide |
| 31 | 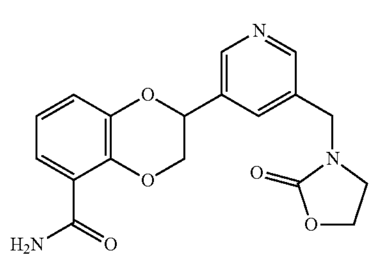 [SMILES: NC(=O)c1cccc2c1OCC(c1cncc(CN3CCOC3=O)c1)O2] | 2-[5-(2-Oxo-oxazolidin-3-ylmethyl)-pyridin-3-yl]-2,3-dihydro-benzo[1,4]dioxine-5-carboxylic acid amide |

TABLE 1-continued

| Cpd | Structure | Name |
|---|---|---|
| 32 | 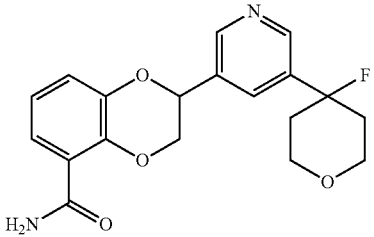 | 2-[5-(4-Fluoro-tetrahydro-pyran-4-yl)-pyridin-3-yl]-2,3-dihydro-benzo[1,4]dioxine-5-carboxylic acid amide |
| 33 | 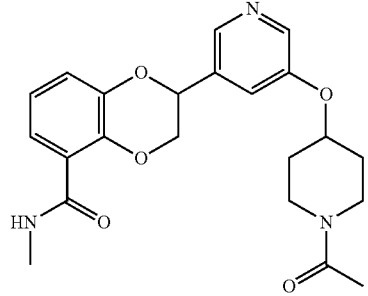 [SMILES: CNC(=O)c1cccc2c1OCC(c1cncc(OC3CCN(C(C)=O)CC3)c1)O2] | 2-[5-(1-Acetyl-piperidin-4-yloxy)-pyridin-3-yl]-2,3-dihydro-benzo[1,4]dioxine-5-carboxylic acid methylamide |
| 34 | 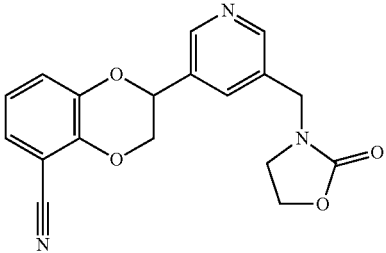 [SMILES: N#Cc1cccc2c1OCC(c1cncc(CN3CCOC3=O)c1)O2] | 2-[5-(2-Oxo-oxazolidin-3-ylmethyl)-pyridin-3-yl]-2,3-dihydro-benzo[1,4]dioxine-5-carbonitrile |
| 35 | 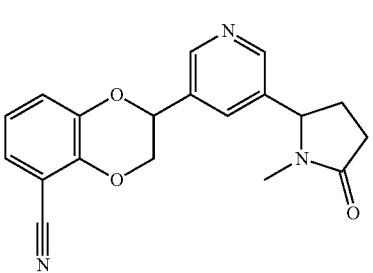 [SMILES: CN1C(=O)CCC1c1cncc(C2COc3c(C#N)cccc3O2)c1] | 2-[5-(1-Methyl-5-oxo-pyrrolidin-2-yl)-pyridin-3-yl]-2,3-dihydro-benzo[1,4]dioxine-5-carbonitrile |
| 36 | 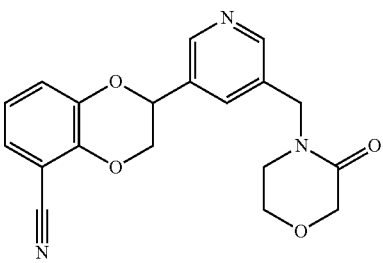 [SMILES: N#Cc1cccc2c1OCC(c1cncc(CN3CCOCC3=O)c1)O2] | 2-[5-(3-Oxo-morpholin-4-ylmethyl)-pyridin-3-yl]-2,3-dihydro-benzo[1,4]dioxine-5-carbonitrile |

TABLE 1-continued

| Cpd | Structure | Name |
|---|---|---|
| 37 | 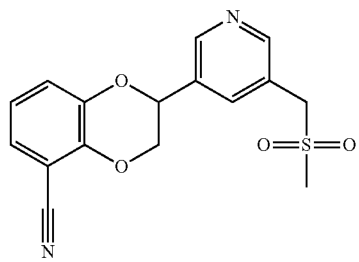 [SMILES: CS(=O)(=O)Cc1cncc(C2COc3c(C#N)cccc3O2)c1] | 2-(5-Methanesulfonylmethyl-pyridin-3-yl)-2,3-dihydro-benzo[1,4]dioxine-5-carbonitrile |
| 38 | 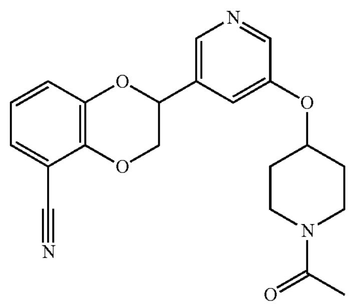 [SMILES: CC(=O)N1CCC(Oc2cncc(C3COc4c(C#N)cccc4O3)c2)CC1] | 2-[5-(1-Acetyl-piperidin-4-yloxy)-pyridin-3-yl]-2,3-dihydro-benzo[1,4]dioxine-5-carbonitrile |
| 39 | 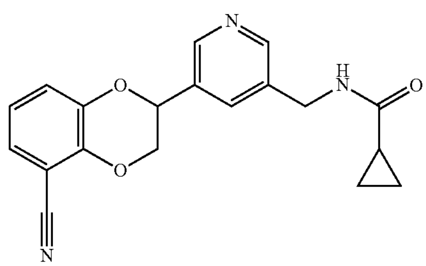 [SMILES: N#Cc1cccc2c1OCC(c1cncc(CNC(=O)C3CC3)c1)O2] | Cyclopropanecarboxylic acid [5-(5-cyano-2,3-dihydro-benzo[1,4]dioxin-2-yl)-pyridin-3-ylmethyl]-amide |
| 40 | 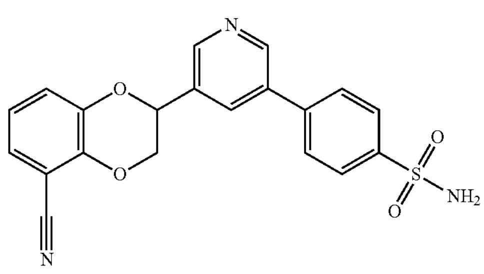 [SMILES: N#Cc1cccc2c1OCC(c1cncc(-c3ccc(S(N)(=O)=O)cc3)c1)O2] | 4-[5-(5-Cyano-2,3-dihydro-benzo[1,4]dioxin-2-yl)-pyridin-3-yl]-benzenesulfonamide |
| 41 | 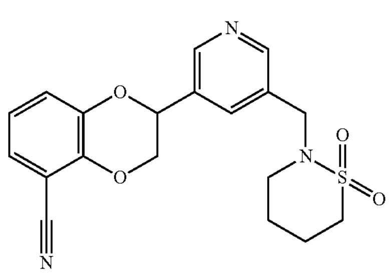 [SMILES: N#Cc1cccc2c1OCC(c1cncc(CN3CCCCS3(=O)=O)c1)O2] | 2-[5-(1,1-Dioxo-1lambda6-[1,2]thiazinan-2-ylmethyl)-pyridin-3-yl]-2,3-dihydro-benzo[1,4]dioxine-5-carbonitrile |

TABLE 1-continued

| Cpd | Structure | Name |
|---|---|---|
| 42 | 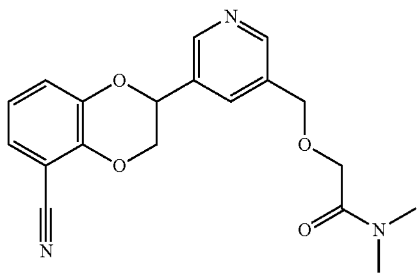 [SMILES: CN(C)C(=O)COCc1cncc(C2COc3c(C#N)cccc3O2)c1] | 2-[5-(5-Cyano-2,3-dihydro-benzo[1,4]dioxin-2-yl)-pyridin-3-ylmethoxy]-N,N-dimethyl-acetamide |
| 43 | 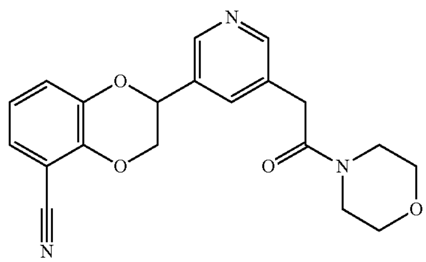 [SMILES: N#Cc1cccc2c1OCC(c1cncc(CC(=O)N3CCOCC3)c1)O2] | 2-[5-(2-Morpholin-4-yl-2-oxo-ethyl)-pyridin-3-yl]-2,3-dihydro-benzo[1,4]dioxine-5-carbonitrile |
| 44 | 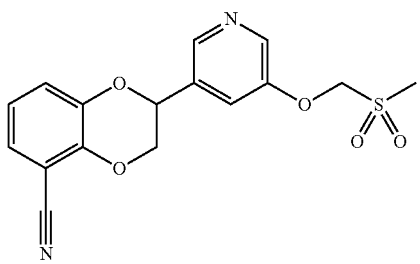 [SMILES: CS(=O)(=O)COc1cncc(C2COc3c(C#N)cccc3O2)c1] | 2-(5-Methanesulfonylmethoxy-pyridin-3-yl)-2,3-dihydro-benzo[1,4]dioxine-5-carbonitrile |
| 45 | 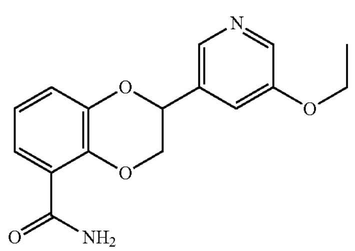 [SMILES: CCOc1cncc(C2COc3c(cccc3C(N)=O)O2)c1] | 2-(5-ethoxy-pyridin-3-yl)-2,3-dihydro-benzo[1,4]dioxine-5-carboxylic acid amide |
| 46 | 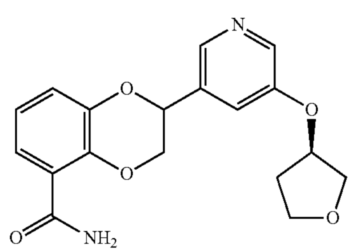 [SMILES: NC(=O)c1cccc2c1OCC(c1cncc(O[C@@H]3CCOC3)c1)O2] | 2-{5-[(R)-(Tetrahydro-furan-3-yl)oxy]-pyridin-3-yl}-2,3-dihydro-benzo[1,4]dioxine-5-carboxylic acid amide |
| 47 | 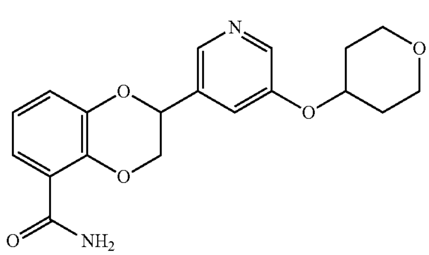 [SMILES: NC(=O)c1cccc2c1OCC(c1cncc(OC3CCOCC3)c1)O2] | 2-[5-(Tetrahydro-pyran-4-yloxy)-pyridin-3-yl]-2,3-dihydro-benzo[1,4]dioxine-5-carboxylic acid amide |

TABLE 1-continued

| Cpd | Structure | Name |
|---|---|---|
| 48 | 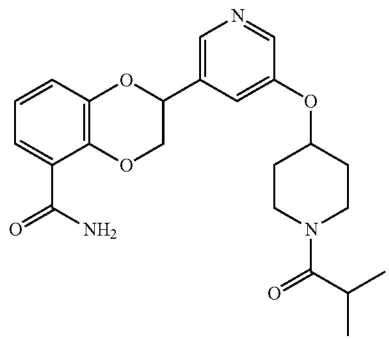 [SMILES: CC(C)C(=O)N1CCC(Oc2cncc(C3COc4c(cccc4C(N)=O)O3)c2)CC1] | 2-[5-(1-isobutyryl-piperidin-4-yloxy)-pyridin-3-yl]-2,3-dihydro-benzo[1,4]dioxine-5-carboxylic acid amide |
| 49 | 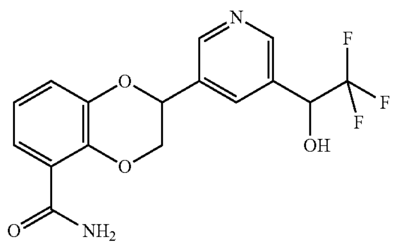 [SMILES: NC(=O)c1cccc2c1OCC(c1cncc(C(O)C(F)(F)F)c1)O2] | 2-[5-(2,2,2-Trifluoro-1-hydroxy-ethyl)-pyridin-3-yl]-2,3-dihydro-benzo[1,4]dioxine-5-carboxylic acid amide |
| 50 | 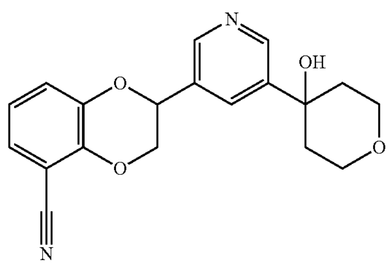 [SMILES: N#Cc1cccc2c1OCC(c1cncc(C3(O)CCOCC3)c1)O2] | 2-[5-(4-Hydroxy-tetrahydro-pyran-4-yl)-pyridin-3-yl]-2,3-dihydro-benzo[1,4]dioxine-5-carbonitrile |
| 51 | 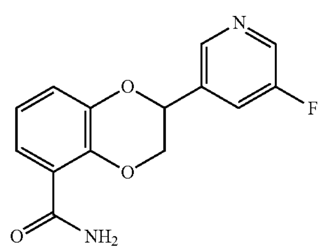 [SMILES: NC(=O)c1cccc2c1OCC(c1cncc(F)c1)O2] | 2-(5-Fluoro-pyridin-3-yl)-2,3-dihydro-benzo[1,4]dioxine-5-carboxylic acid amide |
| 52 | 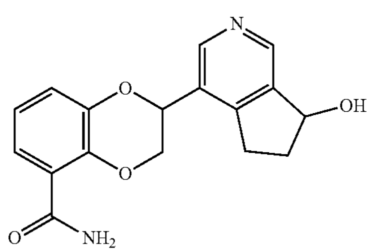 [SMILES: NC(=O)c1cccc2c1OCC(c1cncc3c1CCC3O)O2] | 2-(7-Hydroxy-6,7-dihydro-5H-[2]pyrindin-4-yl)-2,3-dihydro-benzo[1,4]dioxine-5-carboxylic acid amide |
| 53 | 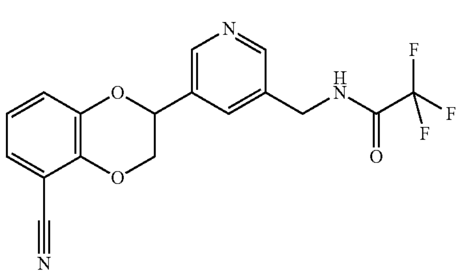 [SMILES: N#Cc1cccc2c1OCC(c1cncc(CNC(=O)C(F)(F)F)c1)O2] | N-[5-(5-Cyano-2,3-dihydro-benzo[1,4]dioxin-2-yl)-pyridin-3-ylmethyl]-2,2,2-trifluoro-acetamide |

TABLE 1-continued

| Cpd | Structure | Name |
|---|---|---|
| 54 | 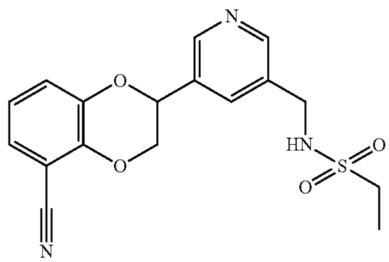 [SMILES: CCS(=O)(=O)NCc1cncc(C2COc3c(C#N)cccc3O2)c1] | Ethanesulfonic acid [5-(5-cyano-2,3-dihydro-benzo[1,4]dioxin-2-yl)-pyridin-3-ylmethyl]-amide |
| 55 | 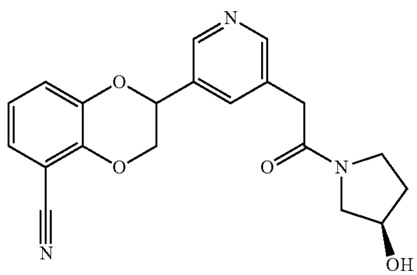 [SMILES: N#Cc1cccc2c1OCC(c1cncc(CC(=O)N3CC[C@@H](O)C3)c1)O2] | 2-{5-[2-((R)-3-Hydroxy-pyrrolidin-1-yl)-2-oxo-ethyl]-pyridin-3-yl}-2,3-dihydro-benzo[1,4]dioxine-5-carbonitrile |
| 56 | 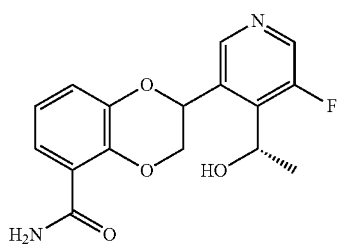 | 2-[5-Fluoro-4-((S)-1-hydroxy-ethyl)-pyridin-3-yl]-2,3-dihydrobenzo[1,4]dioxine-5-carboxylic acid amide |
| 57 | 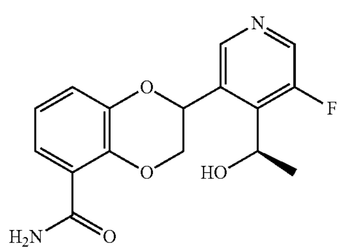 [SMILES: C[C@@H](O)c1c(F)cncc1C1COc2c(cccc2C(N)=O)O1] | 2-[5-Fluoro-4-((R)-1-hydroxy-ethyl)-pyridin-3-yl]-2,3-dihydrobenzo[1,4]dioxine-5-carboxylic acid amide |
| 58 | 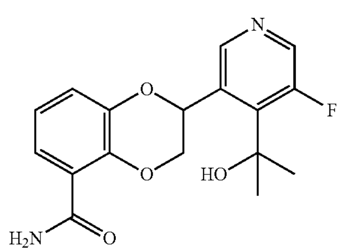 [SMILES: CC(C)(O)c1c(F)cncc1C1COc2c(cccc2C(N)=O)O1] | 2-[5-Fluoro-4-(1-hydroxy-1-methyl-ethyl)-pyridin-3-yl]-2,3-dihydro-benzo[1,4]dioxine-5-carboxylic acid amide |
| 59 | 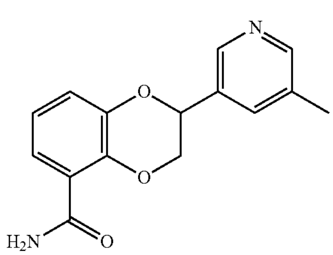 [SMILES: Cc1cncc(C2COc3c(cccc3C(N)=O)O2)c1] | 2-(5-Methyl-pyridin-3-yl)-2,3-dihydro-benzo[1,4]dioxine-5-carboxylic acid amide |

TABLE 1-continued

| Cpd | Structure | Name |
|---|---|---|
| 60 | 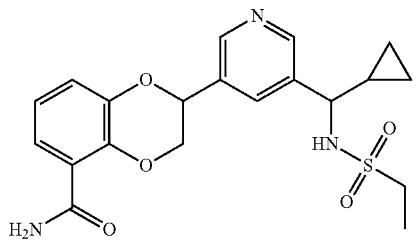 | 2-[5-(cyclopropyl-ethanesulfonylamino-methyl)-pyridin-3-yl]-benzo[1,4]dioxine-5-carboxylic acid amide |
| 61 | 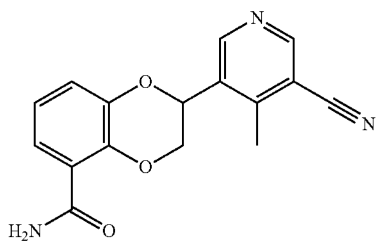 [SMILES: Cc1c(C#N)cncc1C1COc2c(cccc2C(N)=O)O1] | 2-(5-cyano-4-methyl-pyridin-3-yl)-2,3-dihydro-benzo[1,4]dioxine-5-carboxylic acid amide |
| 62 | 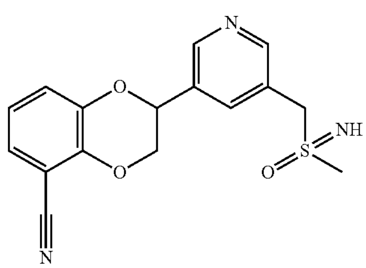 [SMILES: CS(=N)(=O)Cc1cncc(C2COc3c(C#N)cccc3O2)c1] | 2-(5-{[imino(methyl)oxo-$\lambda^6$-sulfanyl]methyl}pyridin-3-yl)-2,3-dihydro-1,4-benzodioxine-5-carbonitrile |

In one embodiment, the invention relates to a compound selected from the group consisting of compounds 1-62 depicted in Table 1 above or a pharmaceutically acceptable salts or a stereoisomer thereof.

In another embodiment, the invention relates to compounds 1, 5, 12, 29, 37, 43, 56, 61, and 62 depicted in Table 1 above or a pharmaceutically acceptable salt or a stereoisomer thereof.

Unless specifically indicated, throughout the specification and the appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Some of the compounds of formula (I) can exist in more than one tautomeric form. The invention includes methods for using all such tautomers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, edetates, camsylates, carbonates, chlorides/hydrochlorides, citrates, edisylates, ethane disulfonates, estolates, esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates, subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of the invention are only those which are contemplated to be 'chemically stable' as will be appreciated by those skilled in the art. For example, peroxides or a compound which would have a 'dangling valency', or a 'carbanion' are not compounds contemplated by the inventive methods disclosed herein.

For all compounds disclosed hereinabove in this application, in the event the nomenclature is in conflict with the structure, it shall be understood that the compound is defined by the structure.

All terms as used herein in this specification, unless otherwise stated, shall be understood in their ordinary meaning as known in the art. For example, "$C_{1-4}$alkyl" is a saturated aliphatic hydrocarbon monovalent radical containing 1-4 carbons such as methyl, ethyl, n-propyl, 1-methylethyl (isopropyl), n-butyl or t-butyl; "$C_{1-4}$ alkoxy" is a $C_{1-4}$ alkyl with a terminal oxygen, such as methoxy, ethoxy, propoxy, butoxy. All alkyl, alkenyl and alkynyl groups shall be understood as being branched or unbranched, cyclized or uncyclized where structurally possible and unless otherwise specified. Other more specific definitions are as follows:

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C-$, $H_3C-CH_2-$, $H_3C-CH_2-CH_2-$, $H_3C-CH(CH_3)-$, $H_3C-CH_2-CH_2-CH_2-$, $H_3C-CH_2-CH(CH_3)-$, $H_3C-CH(CH_3)-CH_2-$, $H_3C-C(CH_3)_2-$, $H_3C-CH_2-CH_2-CH_2-CH_2-$, $H_3C-CH_2-CH_2-CH(CH_3)-$, $H_3C-CH_2-CH(CH_3)-CH_2-$, $H_3C-CH(CH_3)-CH_2-CH_2-$, $H_3C-CH_2-C(CH_3)_2-$, $H_3C-C(CH_3)_2-CH_2-$, $H_3C-CH(CH_3)-CH(CH_3)-$ and $H_3C-CH_2-CH(CH_2CH_3)-$.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes $-(CH_2)-$, $-(CH_2-CH_2)-$, $-(CH(CH_3))-$, $-(CH_2-CH_2-CH_2)-$, $-(C(CH_3)_2)-$, $-(CH(CH_2CH_3))-$, $-(CH(CH_3)-CH_2)-$, $-(CH_2-CH(CH_3))-$, $-(CH_2-CH_2-CH_2-CH_2)-$, $-(CH_2-CH_2-CH(CH_3))-$, $-(CH(CH_3)-CH_2-CH_2)-$, $-(CH_2-CH(CH_3)-CH_2)-$, $-(CH_2-C(CH_3)_2)-$, $-(C(CH_3)_2-CH_2)-$, $-(CH(CH_3)-CH(CH_3))-$, $-(CH_2-CH(CH_2CH_3))-$, $-(CH(CH_2CH_3)-CH_2)-$, $-(CH(CH_2CH_2CH_3))-$, $-(CHCH(CH_3)_2)-$ and $-C(CH_3)(CH_2CH_3)-$.

The term "$C_{3-n}$-cycloalkyl", wherein n is an integer 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heteroaryl" means an aromatic 5 to 6-membered monocyclic heteroaryl or an aromatic 7 to 11-membered heteroaryl bicyclic ring where at least one of the rings is aromatic, wherein the heteroaryl ring contains 1-4 heteroatoms such as N, O and S. Non-limiting examples of 5 to 6-membered monocyclic heteroaryl rings include furanyl, oxazolyl, isoxazolyl, oxadiazolyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic heteroaryl rings include benzimidazolyl, quinolinyl, dihydro-2H-quinolinyl, tetrahydroquinolinyl, isoquinolinyl, quinazolinyl, indazolyl, thieno[2,3-d]pyrimidinyl, indolyl, isoindolyl, benzofuranyl, dihydrobenzofuranyl, benzopyranyl, benzodioxolyl, benzoxazolyl and benzothiazolyl.

The term "heterocyclyl" means a stable nonaromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, azetidinyl, pyrrolidinyl, pyranyl, tetrahydropyranyl, dioxanyl, thiomorpholinyl, 1,1-dioxo-1λ⁶-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro[3,4]octanyl, and 7-azaspiro[3,4]octanyl. The term "heterocyclyl" or is intended to include all the possible isomeric forms.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, a non-limiting example would be —CH$_2$CHF$_2$, —CF$_3$ etc.

Each alkyl, cycloalkyl, heterocycle, aryl or heteroaryl, or the analogs thereof, described herein shall be understood to be optionally partially or fully halogenated.

As used herein, "nitrogen" or N and "sulfur" or S includes any oxidized form of nitrogen and sulfur and the quaternized form of any basic nitrogen. For example, for an —S—C$_{1-6}$ alkyl radical, unless otherwise specified, this shall be understood to include —S(O)—C$_{1-6}$ alkyl and —S(O)$_2$—C$_{1-6}$ alkyl, likewise, —S—R$_a$ may be represented as phenyl-S(O)$_m$— when R$_a$ is phenyl and where m is 0, 1 or 2.

General Synthetic Methods

The compounds of the invention may be prepared by the methods and examples presented below and methods known to those of ordinary skill in the art. The methods that are described here are intended as an illustration and for the enablement of the instant invention without restricting the scope of its subject matter, the claimed compounds, and the examples. Optimum reaction conditions and reaction times may vary depending on the particular reactants used. Unless otherwise specified, solvents, temperatures, pressures, and other reaction conditions may be readily selected by one of ordinary skill in the art. Specific procedures are provided below. Intermediates used in the syntheses below are either commercially available or easily prepared by methods known to those skilled in the art. Reaction progress may be monitored by conventional methods such as thin layer chromatography (TLC) or high pressure liquid chromatography-mass spec (HPLC-MS). Intermediates and products may be purified by methods known in the art, including column chromatography, HPLC, preparative TLC, supercritical fluid chromatography (SFC), and recrystallization.

Compounds of formula (I) may be prepared as illustrated in Scheme 1.

Scheme 1

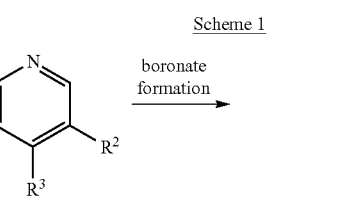

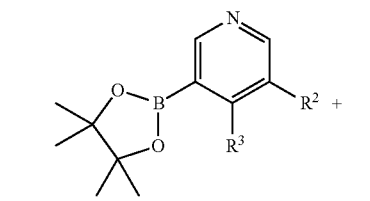

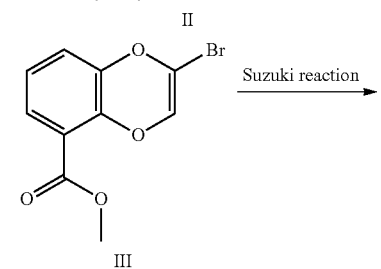

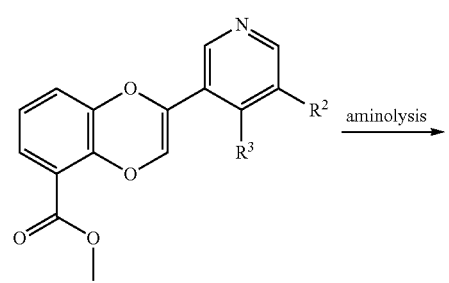

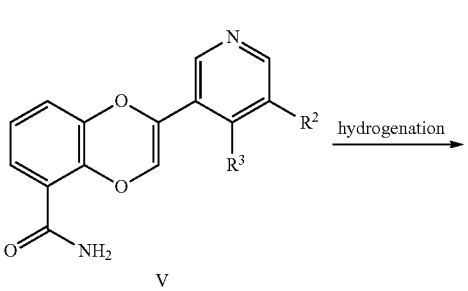

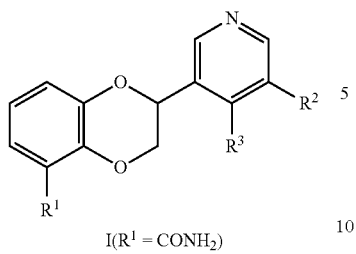

I(R$^1$ = CONH$_2$)

As illustrated in Scheme 1, a suitable heteroaromatic bromide may be converted to boronate ester II via palladium catalyzed coupling reaction with a diboronyl ester such as bis(pinacolato)diboron. Suzuki reaction with vinyl bromide III (Intermediate 1) provides IV. Aminolysis of ester IV provides amide V. Hydrogenation over palladium on carbon provides the desired compound of formula I (R$^1$=CONH$_2$).

Compounds of formula (I) may also be prepared as illustrated in Scheme 2.

Scheme 2

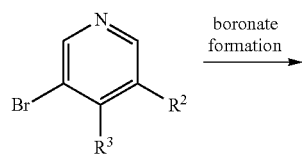
boronate formation

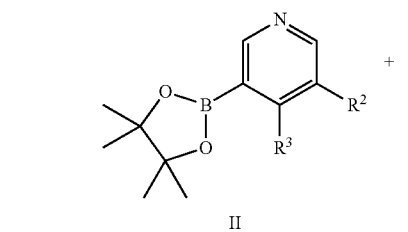

II

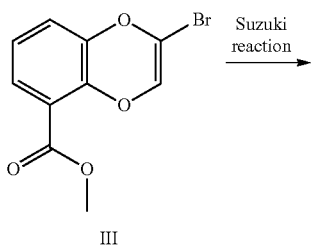

III

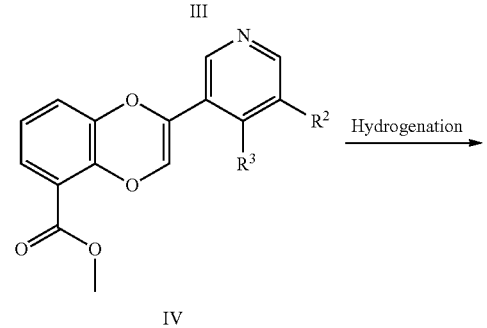

IV

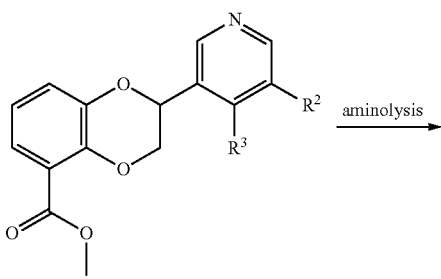

VI aminolysis

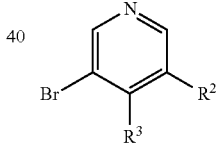

I
(R$^1$ = CONH$_2$)

As illustrated in Scheme 2, compounds of formula I may also be prepared by hydrogenation of compound IV followed by aminolysis to give I.

Compounds of formula (I) may also be prepared as illustrated in Scheme 3.

Scheme 3

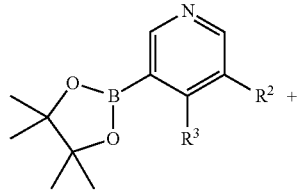
boronate formation

II

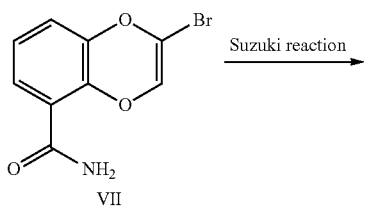

VII
Suzuki reaction

-continued

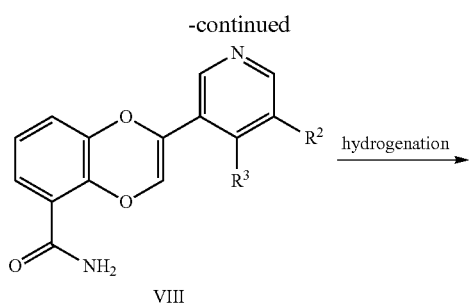

VIII

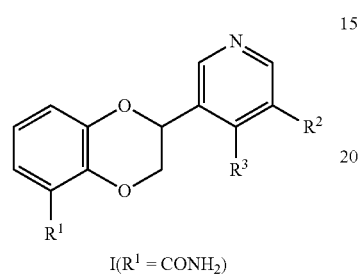

I(R¹ = CONH₂)

As illustrated in Scheme 3, a suitable heteroaromatic bromide may be converted to a boronate ester II via palladium catalyzed coupling reaction with a diboronyl ester such as bis(pinacolato)diboron. Suzuki reaction with vinyl bromide VII (Intermediate 2) provides VIII. Hydrogenation over palladium on carbon provides the desired compound of formula I (R¹=CONH₂).

Compounds of formula I R¹=—CN maybe prepared from compounds of formula 1 R¹=—CONH₂ by reacting with a suitable dehydrating reagent such as trifluoroacetic anhydride in the presence of base as shown is Scheme 4.

Scheme4

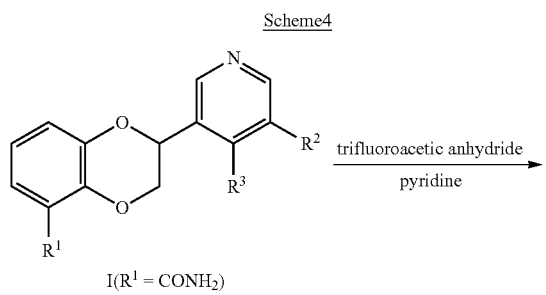

I(R¹ = CONH₂)

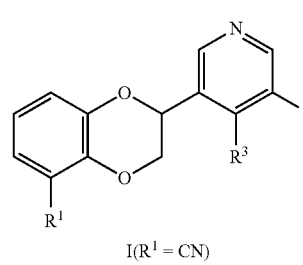

I(R¹ = CN)

SYNTHETIC EXAMPLES

Synthesis of Intermediates

Intermediate 1:
2-bromo-benzo[1,4]dioxine-5-carboxylic acid methyl ester

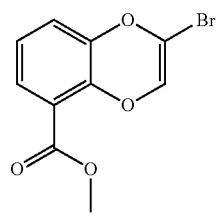

Step A: To a suspension of 2,3-dihydro-benzo[1,4]dioxine-5-carboxylic acid (49.7 g, 275.6 mmol) in 1000 mL of MeOH, is added acetyl chloride (40.0 ml, 560.5 mmol) in a drop-wise manner. Upon complete addition, the reaction is stirred at room temperature for 18 hours. The reaction mixture is then concentrated in vacuo and the residue is dissolved in EtOAc and washed with sat. NaHCO₃. The aqueous layer is separated, and extracted with EtOAc. The combined organic layers are washed with brine, dried under Na₂SO₄, filtered and concentrated to afford 50.7 g of 2,3-dihydro-benzo[1,4]dioxine-5-carboxylic acid methyl ester.

Step B: To a mixture of 2,3-dihydro-benzo[1,4]dioxine-5-carboxylic acid methyl ester (50.7 g, 261.1 mmol) in carbon tetrachloride (300 ml) is added 2,2'-azobis(isobutyronitrile) (125 mg, 0.7 mmol) and N-bromosuccinimide (90.0 g, 505.7 mmol). The reaction mixture is refluxed using a 60 W lamp (covered with aluminum foil) for 24 hours. After this time another 100.0 g (561.8 mmol) of N-bromosuccinimide, 175 mg (1.1 mmol) of 2,2'-azobis(isobutryonitrile) and 100 mL of carbon tetrachloride are added. The reaction mixture is stirred under the same conditions for another 24 hours. After this time, another 40.0 g (224.7 mmol) of N-bromosuccinimide and 100 mg (0.6 mmol) of 2,2'-azobis(isobutryonitrile) are added. The reaction mixture is stirred under the same conditions for another 72 hours after which time the reaction appeared complete. To the reaction mixture is added 1 L of ether. The resulting solid is filtered off and washed with ether. The combined organics are concentrated and the crude solid is dissolved in 20% EtOAc/heptane, and purified by a plug of silica gel (500 g), eluting with 20% EtOAc/heptane. The product fractions are collected and concentrated to afford 86.5 g of 2,3-dibromo-2,3-dihydro-benzo[1,4]dioxine-5-carboxylic acid methyl ester.

Step C: A suspension of 2,3-dibromo-2,3-dihydro-benzo[1,4]dioxine-5-carboxylic acid methyl ester (22.7 g, 64.5 mmol) in 200 mL of MeOH is warmed to 50° C. and treated with 500 mL of sodium methoxide (0.5M in methanol, 250 mmol). The reaction mixture is warmed to 65° C. and stirred for 2 hours. The reaction mixture is treated with silica gel and concentrated. The dry residue is purified via silica gel flash column chromatography eluting with 0-15% EtOAc/heptane to afford 2.6 g of the title compound.

Intermediate 2:
2-bromo-benzo[1,4]dioxine-5-carboxylic acid amide

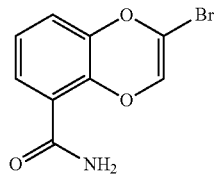 [SMILES: NC(=O)c1cccc2c1OC=C(Br)O2]

A 20 mL reaction vessel is charged with 2-bromo-benzo[1,4]dioxine-5-carboxylic acid methyl ester (1.2 g, 4.4 mmol) and 7N ammonia solution in methanol (13.0 mL, 88.5 mmol). The vessel is capped and heated at 75 C for 18 hours. Upon cooling to room temperature, the mixture is concentrated to dryness. The remaining solid is diluted with MeOH (10 mL) and sonicated. Filtration affords 1.00 g of 2-bromo-benzo[1,4]dioxine-5-carboxylic acid amide.

Intermediate 3:
2-bromo-benzo[1,4]dioxine-5-carboxylic acid methylamide

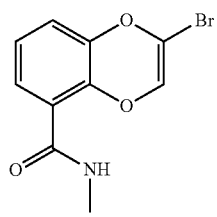

The title compound is prepared in a similar manner to Intermediate 2 replacing ammonia with methylamine.

Intermediate 4: 3-bromo-5-fluoro-4-methyl-pyridine

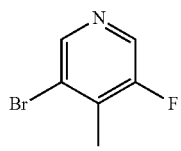

A solution of diisopropylamine (1.9 mL, 13.7 mmol) in 20 mL of THF is cooled to 0° C. and treated with n-butyllithium (6.7 mL, 13.6 mmol). The mixture is stirred at 0° C. for 15 minutes then cooled to −78° C. 3-Bromo-5-fluoropyridine (2.0 g, 11.4 mmol) is added drop-wise as a solution in 20 mL of THF. This mixture is stirred at −78° C. for 45 minutes. A separate solution of iodomethane (2.1 mL, 34.1 mmol) in 20 mL of THF is cooled to −78° C. The anion solution is then cannulated into the iodomethane solution. Once the transfer is complete, the mixture is stirred at −78° C. for 30 minutes. The cooling bath is removed and the mixture is stirred for 30 minutes and then quenched with saturated NH$_4$Cl solution. The mixture is diluted with EtOAc and water. The organic layer is washed with brine, dried over MgSO$_4$, filtered and concentrated. The residue is purified via silica gel flash column chromatography eluting with 0-10% EtOAc/heptane to afford 1.4 g of the title compound.

Intermediate 5: 3-bromo-5-difluoromethyl-pyridine

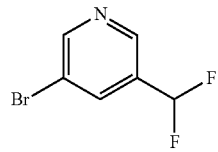

A solution of 5-bromo-3-formylpyridine (1.5 g, 8.1 mmol) in 15.00 mL of DCM is cooled to −78° C. and then treated with diethylaminosulfur trifluoride (5.3 mL, 40.3 mmol) drop-wise. The solution is allowed to warm to room temperature overnight. The reaction mixture is added drop-wise to a stirred cold solution of dilute NH$_4$OH and diluted with more DCM. The organic layer is separate and the aqueous layer is back extracted with DCM. The organic layers are combined and are washed with brine, dried over MgSO4, filtered and concentrated. The residue is purified by silica gel flash column chromatography eluting with 0-30% EtOAc/heptane to afford 1.1 g of the title compound.

Intermediate 6:
3-[(5-bromo-3-pyridyl)methyl]oxazolidin-2-one

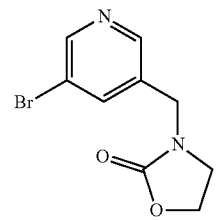 [SMILES: O=C1OCCN1Cc1cncc(Br)c1]

Step A: A solution of (5-bromo-3-pyridyl)methanol (7.0 g, 37.2 mmol) in 10 mL of DCM is cooled to 0° C. Triphenylphosphine (9.8 g, 37.2 mmol) is added followed by the slow addition of carbon tetrabromide (18.5 g, 55.8 mmol) as the reaction is exothermic. The mixture is stirred at 0'C for 3 hours. After the reaction is complete, the reaction mixture is absorbed with silica gel and purified by silica flash column chromatography to afford 7.5 g of 3-bromo-5-(bromomethyl)pyridine.

Step B: 2-Oxazolidone (0.6 g, 7.2 mmol) is dissolved in 20 mL of DMF and cooled to 0° C. 60% sodium hydride (0.29 g, 7.2 mmol) is added. Bubbling is observed. The mixture is stirred for 5 minutes. 3-Bromo-5-(bromomethyl)pyridine (1.2 g, 4.8 mmol) as a solution in 15 mL of DMF is added slowly. The reaction mixture is allowed to warm to room temperature for 16 hours. The reaction is quenched with 10 mL of water. The mixture is filtered through diatomaceous earth and rinsed with EtOAc (50 mL). The EtOAc layer is concentrated. The crude product is by silica gel flash column chromatography eluting with 0-10% MeOH in DCM to afford 0.9 g of the title compound.

The following intermediates are synthesized according to the procedure for Intermediate 6, substituting the appropriate commercially available reagents.

| Intermediate | Structure | Name |
|---|---|---|
| 7 | 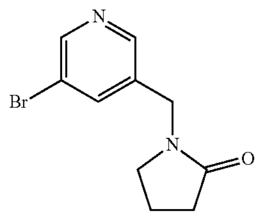 [SMILES: O=C1CCCN1Cc1cncc(Br)c1] | 1-(5-bromo-pyridin-3-ylmethyl)-pyrrolidin-2-one |
| 8 | 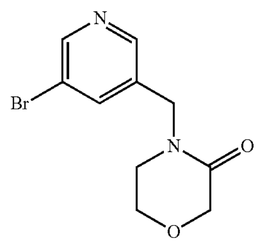 [SMILES: O=C1COCCN1Cc1cncc(Br)c1] | 4-[5-(4,4,5,5-tetramethyl-[1,3,2]dioxaborolan-2-yl)-pyridin-3-ylmethyl]-morpholin-3-one |
| 9 | 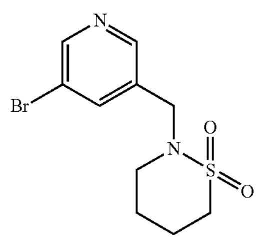 [SMILES: O=S1(=O)CCCCN1Cc1cncc(Br)c1] | 2-(5-bromo-pyridin-3-ylmethyl)-[1,2]thiazinane 1,1-dioxide |

Intermediate 10:
4-(5-bromo-pyridin-3-yl)-benzenesulfonamide

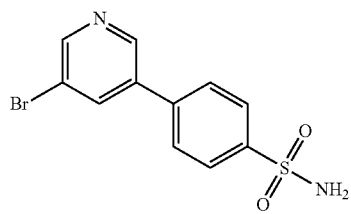 [SMILES: NS(=O)(=O)c1ccc(-c2cncc(Br)c2)cc1]

3,5-Dibromopyridine (1.0 g, 4.2 mmol), (4-aminosulphonyl)benzeneboronic acid (0.8 g, 4.2 mmol), 1,1'-bis(diphenylphosphino)ferrocenedichloropalladium(II) DCM complex (172 mg, 0.211 mmol), 20 mL of 1,4-dioxane, and 2.0M sodium carbonate solution (4.2 mL, 8.4 mmol) are combined in a pressure vessel. The vessel is flushed with argon, sealed and stirred at 120° C. for 2 hours. The reaction mixture is diluted with EtOAc/water. The mixture is filtered through diatomaceous earth, and the layers are separated. The organic layer is washed with brine, dried over MgSO₄, filtered and concentrated. The residue is purified by silica gel flash column chromatography eluting with 50-100% EtOAc/Heptane to afford 0.6 g of the title compound.

Intermediate 11: 1-[(S)-3-(5-bromo-pyridin-3-yloxy)-pyrrolidin-1-yl]-ethanone

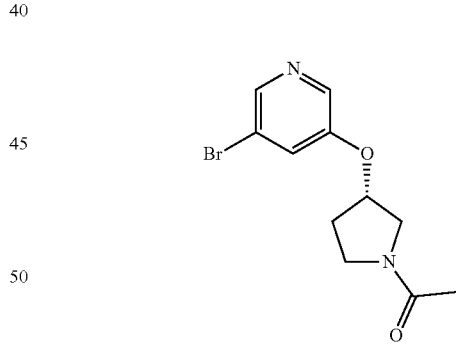

To a stirred solution of triphenylphosphine (28.9 g, 110 mmol) in 100 mL of THF cooled to 0° C. is added diisopropyl azodicarboxylate (20.9 g, 103 mmol) and 5-bromo-pyridin-3-ol (12.0 g, 69 mmol) as a solution in 50 mL THF. 1-((R)-3-Hydroxy-cyclopentyl)-ethanone (8.8 g, 69 mmol) as a solution in 50 mL of THF is added slowly. The reaction is stirred at room temperature for 3 hours. The reaction is quenched with water and extracted with EtOAc (2×200 mL). The combined organic layers are concentrated under reduced pressure. The crude product is purified by silica gel flash chromatography and washed with diethyl ether to afford 6.5 g of the title compound.

The following intermediates are synthesized according to the procedure for Intermediate 10, substituting the appropriate commercially available reagents.

| Intermediate | Structure | Name |
|---|---|---|
| 12 | ![structure] | 1-[(R)-3-(5-bromo-pyridin-3-yloxy)-pyrrolidin-1-yl]-ethanone |
| 13 | ![structure] | 1-[3-(5-bromo-pyridin-3-yloxy)-azetidin-1-yl]-ethanone |
| 14 | ![structure] | 1-[4-(5-bromo-pyridin-3-yloxy)-piperidin-1-yl]-ethanone |

Intermediate 15:
3-bromo-5-methanesulfonylmethyl-pyridine

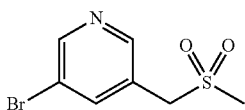

Step A: To a cooled (0° C.) solution of (5-bromo-pyridin-3-yl)-methanol (5.0 g, 26.6 mmol) and triphenylphosphine (8.4 g, 31.9 mmol) in 130 mL of DCM is added carbon tetrabromide (13.2 g, 39.9 mmol). The resulting mixture is stirred at 0° C. for 10 minutes. The mixture is concentrated and purified by silica gel flash chromatography eluting with 0-40% EtOAc in heptane to afford 6.1 g of 3-bromo-5-bromomethyl-pyridine.

Step B: 3-Bromo-5-bromomethyl-pyridine (100 mg, 0.4 mmol), sodium methanesulphinate (122 mg, 1.2 mmol), and 1 mL of DMF are combined in a reaction vial. The vial is sealed and the reaction is stirred at 65° C. in a heating block for 1 hour. The mixture is cooled to room temperature, diluted with EtOAc (30 mL), washed with water (3×15 mL), and brine, dried over sodium sulfate, filtered, and concentrated. The crude product is purified by silica gel flash chromatography eluting with 0-100% EtOAc in heptane to afford 70 mg of the title compound.

Intermediate 16: 1-[(R)-3-(5-bromo-pyridin-3-yloxy)-piperidin-1-yl]-ethanone

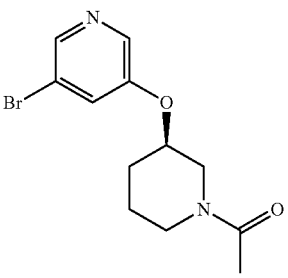 [SMILES: CC(=O)N1CCC[C@@H](Oc2cncc(Br)c2)C1]

Step A: To a cooled (0° C.) solution of PPh$_3$ (1.2 g, 4.5 mmol) in 50 mL of THF is added diisopropyl azodicarboxylate (0.81 mL, 4.1 mmol), drop-wise. After stirring at 0° C. for 15 minutes, 5-bromo-pyridin-3-ol (441 mg, 2.5 mmol) and (S)-3-hydroxy-piperidine-1-carboxylic acid tert-butyl ester (500 mg, 2.5 mmol) are added and the mixture is warmed and stirred at room temperature for 16 hours. The mixture is concentrated and purified by silica gel flash column chromatography to give 596 mg of (R)-3-(5-bromo-pyridin-3-yloxy)-piperidine-1-carboxylic acid tert-butyl ester.

Step B: A solution of (R)-3-(5-bromo-pyridin-3-yloxy)-piperidine-1-carboxylic acid tert-butyl ester (596 mg, 1.7 mmol) in 5 mL of MeOH and 4 N HCl solution in 1,4-dioxane (1.5 mL) is stirred at room temperature for 16 hours. The mixture is concentrated to provide 525 mg of 3-bromo-5-((R)-piperidin-3-yloxy)-pyridine as the hydrochloride salt.

Step C: To a solution of 3-bromo-5-((R)-piperidin-3-yloxy)-pyridine hydrochloride salt (525 mg, 1.8 mmol) in 10 mL of DMF is added acetyl chloride (0.19 mL, 2.7 mmol) and N,N-diisopropylethylamine (1.4 mL, 8.0 mmol). The mixture is stirred at room temperature for 16 hours. The reaction is partitioned between H₂O and EtOAc, and the layers are separated. The aqueous layer is extracted with EtOAc. The organic layers are combined, dried and concentrated. The crude product is purified by silica gel flash column chromatography to provide 271 mg of the title compound.

Intermediate 17: methanesulfonic acid 5-(tetrahydro-pyran-4-yl)-pyridin-3-yl ester

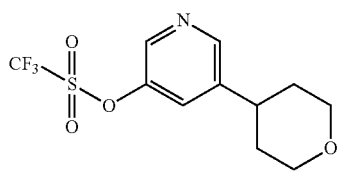 [SMILES: O=S(=O)(Oc1cncc(C2CCOCC2)c1)C(F)(F)F]

Step A: 5-Bromo-pyridin-3-ol (15 g, 86.2 mmol), 4-(4,4,5,5-tetramethyl-[1,3,2]dioxaborolan-2-yl)-3,6-dihydro-2H-pyran (27 g, 129.3 mmol), potassium acetate (12.7 g, 129.3 mmol), and Bis(diphenylphosphino)ferrocene]dichloropalladium(II) (1.3 g, 1.7 mmol) are combined in 150 mL of dioxane and 30 mL of water. The reaction is refluxed for 16 hours. The reaction is concentrated to dryness. The residue is partitioned between H₂O and EtOAc and the layers are separated. The aqueous layer is extracted with EtOAc and the combined organic layers are dried and concentrated. The crude product is purified by silica gel flash column chromatography to provide 10.5 grams of 5-(3,6-dihydro-2H-pyran-4-yl)-pyridin-3-ol.

Step B: To the solution of 5-(3,6-dihydro-2H-pyran-4-yl)-pyridin-3-ol (9.0 g, 50.8 mmol) in one liter of MeOH is added 10% Pd—C. The suspension is degassed under vacuum and is purged with hydrogen. The mixture is stirred under 50 psi of hydrogen at 50° C. for 5 hours. At the end of the reaction, the mixture is filtered and washed with MeOH. The filtrate is concentrated and purified by silica gel flash column chromatography to give 9 grams of 5-(tetrahydro-pyran-4-yl)-pyridin-3-ol.

Step C: To a solution of the 5-(tetrahydro-pyran-4-yl)-pyridin-3-ol (500 mg, 2.8 mmol), DMAP (13 mg, 0.1 mmol), and triethylamine (0.78 mL, 5.6 mmol) in 20 mL of DCM is added triflic anhydride (0.47 mL, 2.8 mmol) dropwise. The reaction is allowed to stir at room temperature overnight. The reaction is diluted with 1N NaOH. The layers are separated and the DCM layer is concentrated to dryness. The residue is purified by silica gel flash column chromatography eluting with 5-50% EtOAc in heptanes to give 415 mg of the title compound.

Intermediate 18: 1-(5-bromo-pyridin-3-yl)-cyclohexanol

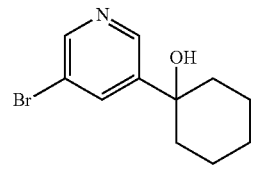 [SMILES: OC1(c2cncc(Br)c2)CCCCC1]

To 3,5-dibromopyridine (1.5 g, 6.3 mmol) in 6 mL of THF at −20° C. is added 1.3M i-PrMgCl_LiCl solution (4.7 mL, 6.1 mmol) in one portion. The mixture is allowed to stir for 30 minutes, warming to −10° C. The mixture is cooled to −20° C. and cyclohexanone (0.79 mL, 7.6 mmol) is added. The reaction is quenched with 50 mL of saturated aqueous NH₄Cl and diluted with 200 mL EtOAc. The organic phase is washed with 2×100 mL of H₂O and 1×100 mL of brine. The organic phase is dried with MgSO₄, filtered and concentrated. The residue is purified by silica gel flash column chromatography eluting with 0-10% MeOH/CH₂Cl₂ to give 560 mg of the title compound.

The following intermediates are synthesized according to the procedure for Intermediate 18, substituting either commercially available reagents or the appropriate intermediates described above.

| Intermediate | Structure | Name |
| --- | --- | --- |
| 19 | 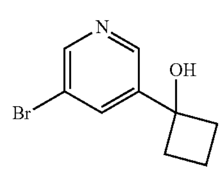 [SMILES: OC1(c2cncc(Br)c2)CCC1] | 1-(5-bromo-pyridin-3-yl)-cyclobutanol |
| 20 | 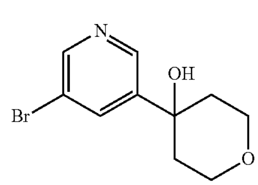 | 4-(5-bromo-pyridin-3-yl)-tetrahydropyran-ol |

Intermediate 21: 5-(5-bromo-pyridin-3-yl)-1-methyl-pyrrolidin-2-one

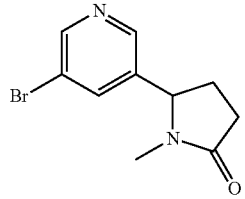

Step A: 3-Bromo-5-(pyrrolidin-2-yl)pyridine (400 mg, 1.8 mmol), 4 mL of glacial acetic acid and 1 mL of water is added to a reaction vial. Bromine (0.8 mL) is added dropwise. The vial is sealed and the reaction is heated to 90° C. in an oil bath and continued to stir at that temperature for 3 hours. The mixture is cooled to room temperature. Water (15 mL) is added to the cooled reaction mixture and the mixture is saturated with solid potassium carbonate. The mixture is extracted with EtOAc (3×30 mL). The combined organics are dried over sodium sulfate, filtered, and concentrated. The residue is purified by silica gel flash column chromatography eluting with 0-6% MeOH in DCM to afford 0.65 g of 3,3-dibromo-5-(5-bromo-pyridin-3-yl)-pyrrolidin-2-one.

Step B: Sodium borohydride (0.74 g, 19.6 mmol) is suspended in 17 mL of ethanol and tellurium metal powder (1.25 g, 9.8 mmol) is added in portions. The mixture is heated under reflux for 15 minutes and the mixture becomes a light purple color. The mixture is cooled to room temperature. 3,3-Dibromo-5-(5-bromo-pyridin-3-yl)-pyrrolidin-2-one (0.65 g, 1.6 mmol) dissolved in 5 mL of ethanol is added slowly. The mixture is stirred at room temperature for 72 hours. The mixture is filtered through diatomaceous earth and washed with MeOH. The filtrate is concentrated. The resulting crude product is purified by silica gel flash column chromatography eluting with 0-6% MeOH in DCM to afford 290 mg of 5-(5-bromo-pyridin-3-yl)-pyrrolidin-2-one.

Step C: To a solution of 5-(5-bromo-pyridin-3-yl)-pyrrolidin-2-one (202 mg, 0.84 mmol) in 5 mL of THF is added 60% NaH (50 mg, 1.3 mmol). The mixture is stirred at room temperature for 5 minutes and methyl iodide (0.078 mL, 1.3 mmol) is then added drop-wise. The mixture is stirred at room temperature for 16 hours. The mixture is then concentrated and purified by silica gel flash column chromatography to give 157 mg of the title compound. Enantiomers are separated using Chiral SFC (Chiralpak AD-H, 30% (1:1 Isopropanol+0.5% TFA:Hexanes):$CO_2$, 70 mL/min, 140 bar, 25° C.).

Intermediate 22: 1-(5-Bromo-4-methyl-pyridin-3-yl)-ethanol

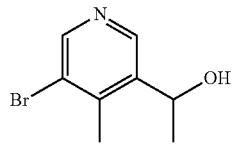

To a solution of 3,5-dibromo-4-methyl-pyridine (2.0 g, 8.0 mmol) in 100 mL of THF cooled in a liquid $N_2$/ethanol bath below −100° C. is added 2.5 M n-butyllithium in hexanes solution (3.2 mL, 8.0 mmol). This is stirred for 5 minutes, then neat acetaldehyde (4.5 mL, 8.0 mmol) is added all at once. The reaction is allowed to warm to −78° C. over 30 minutes. The temperature is held at −78° C. by adding dry ice to the bath. The reaction is kept at −78° C. for 1 hour. The reaction is quenched with sat $NH_4Cl$ at −78° C. The reaction is allowed to warm to room temperature. The reaction is diluted with EtOAc and water. The organic layer is concentrated to dryness. The residue is purified by silica gel flash column chromatography eluting with 20-100% EtOAc in heptanes to give 0.88 g of the title compound. Chiral SFC (LUX Cellulose-4, 12%(1:1:1 MeOH:EtOH:IPA):$CO_2$, 70 mL/min, 120 bar, 40° C.) of 2.5 g of 1-(5-bromo-4-methyl-pyridin-3-yl)-ethanol gives 0.98 g of enantiomer A and 0.98 g of enantiomer B.

Intermediate 23: 3-bromo-5-methanesulfonylmethoxy-pyridine

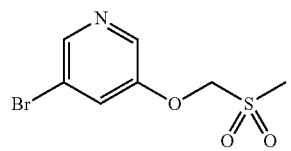

Step A: To a solution of 5-bromo-pyridin-3-ol (500 mg, 2.9 mmol) in 5 mL of DMF is added sodium hydride 60% dispersion in mineral oil (230 mg, 5.8 mmol). The reaction is stirred for 15 minutes when chloromethyl methyl sulfide (0.24 mL, 2.9 mmol) is added. The reaction is stirred for 1 hour, then it is diluted with EtOAc and water. The organic layer is concentrated to dryness to give 330 mg of 3-bromo-5-methylsulfanylmethoxy-pyridine.

Step B: To a solution of 3-bromo-5-methylsulfanyl-methoxy-pyridine (330 mg, 1.4 mmol) in 10 mL of DCM is added 3-chloroperbenzoic acid 77% (608 mg, 3.5 mmol). The reaction is allowed to stir overnight. The mixture is quenched with 1N NaOH. The layers are separated and the organic layer is concentrated to dryness. Silica gel flash column chromatography eluting with EtOAc in heptanes gives 175 mg of the title compound.

Intermediate 24: 2-[(5-bromo-3-pyridyl)methoxy]-N,N-dimethyl-acetamide

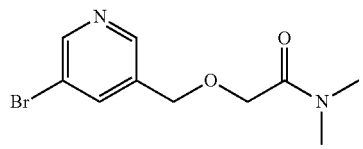

(5-Bromo-pyridin-3-yl)-methanol (2.0 g, 11 mmol) is added to a 0° C. solution of 60% NaH (0.51 g, 12.8 mmol) in 150 mL of THF. The mixture is stirred at room temperature for 1 hour then cooled to 0° C. 2-Chloro-N,N-dimethyl-acetamide (1.42 g, 12 mmol) is added to the mixture. The cooling bath is removed and the mixture is stirred at room temperature for 16 hours. The reaction is quenched with brine (0.5 mL) and filtered through a pad of diatomaceous earth. The filtrate is concentrated, diluted with DCM, treated with MgSO$_4$ and filtered through diatomaceous earth again. The filtrate is concentrated and the crude product is purified by silica gel flash column chromatography eluting with 0-6% MeOH/DCM to 1.95 g of the title compound.

Intermediate 25:
2-(5-bromo-3-pyridyl)-1-morpholino-ethanone

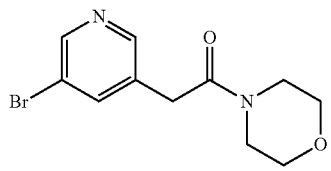 [SMILES: O=C(Cc1cncc(Br)c1)N1CCOCC1]

To the solution of 5-bromo-3-pyridineacetic acid (500 mg, 2.3 mmol) in 3 mL of DMF is added TBTU (1.1 g, 3.4 mmol). Morpholine (0.61 mL, 6.9 mmol) is added dropwise. The resulting reaction mixture is stirred at room temperature for 16 hours. The mixture is diluted with 50 mL of EtOAc, washed with water (3×5 mL), and brine, dried over sodium sulfate, filtered, and concentrated. The resulting crude product is purified by silica gel flash column chromatography eluting with 0-4.5% MeOH/DCM to afford 381 mg of the title compound.

The following intermediates are synthesized according to the procedure for Intermediate 25, substituting either commercially available reagents or the appropriate intermediates described above.

Intermediate 29:
1-(5-bromo-pyridin-3-yl)-cyclopropanecarbonitrile

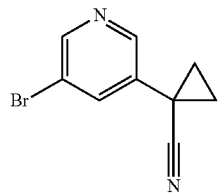 [SMILES: N#CC1(c2cncc(Br)c2)CC1]

To a suspension of (5-bromo-pyridin-3-yl)-acetonitrile (1.0 g, 5.1 mmol) in 50% NaOH (20 mL) is added 1-bromo-2-chloro-ethane (764 mg, 5.3 mmol) and benzyl triethylammonium chloride (15 mg, 0.1 mmol). The resultant mixture is heated to 60° C. for 2 hours. After cooling down to room temperature, EtOAc is added. The layers are separated, and the aqueous layer is extracted with fresh EtOAc. The organic layers are combined, washed with brine, dried over Na$_2$SO$_4$, filtered and concentrated. The product is purified by silica gel flash column chromatography to afford 626 mg of the title compound.

Intermediate 30: cyclopropanecarboxylic acid (5-bromo-pyridin-3-ylmethyl)-amide

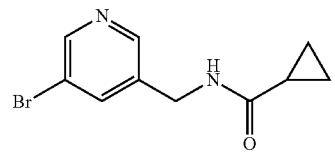 [SMILES: O=C(NCc1cncc(Br)c1)C1CC1]

| Intermediate | Structure | Name |
|---|---|---|
| 26 | ![structure] | 2-(5-bromo-3-pyridyl)-1-(4,4-difluoro-1-piperidyl)ethanone |
| 27 | ![structure] | 2-(5-bromo-pyridin-3-yl)-N,N-dimethyl-acetamide |
| 28 | ![structure] | 2-(5-bromo-pyridin-3-yl)-1-(R)-3-hydroxy-pyrrolidin-1-yl)-ethanone |

To a stirred solution of cyclopropanecarboxylic acid (0.58 g, 6.7 mmol) in 50 mL of DMF is added HATU (3.1 g, 8.0 mmol) followed by (5-bromo-pyridin-3yl)-methylamine (1.3 g, 6.7 mmol) and N,N-diisopropylethylamine (7.5 mL, 42.8 mmol). The resulting mixture is stirred at room temperature for 16 hours after which time it is concentrated to low volume, poured into 150 mL of water and extracted with EtOAc (3×). The combined organics are dried over MgSO₄, filtered and concentrated. The remaining residue is purified via silica gel flash column chromatography eluting with 0-8% MeOH/DCM to give 1.10 g of the title compound.

The following intermediate is synthesized according to the procedure for Intermediate 30, substituting the appropriate commercially available reagent.

| Intermediate | Structure | Name |
|---|---|---|
| 31 | 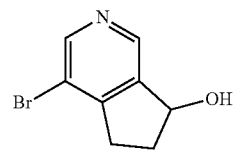 | cyclopropanecarboxylic acid (5-bromo-pyridin-3-ylmethyl)-methyl-amide |

Intermediate 32: 3-bromo-5-(4-fluoro-tetrahydro-pyran-4-yl)-pyridine

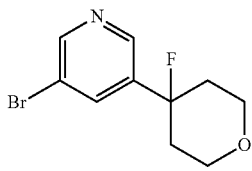

A solution of (diethylamino)sulfur trifluoride (0.63 g, 3.9 mmol) in 6.0 mL of DCM is cooled to −78° C. and treated with a solution of 4-(5-bromo-pyridin-3-yl)-tetrahydro-pyran-4-ol (1.0 g, 3.9 mmol) in 15 mL of DCM. The reaction is stirred at −78° C. for 2 hours then warmed to room temperature and poured over ice. The mixture is stirred until all of the ice has melted at which time the layers are separated. The aqueous phase is extracted once more with DCM and the combined organics are washed with water, brine and then dried (MgSO₄). The organic is filtered and concentrated to give 0.90 g of the title compound.

Intermediate 33:
1-(5-bromo-pyridin-3-yl)-2,2,2-trifluoro-ethanol

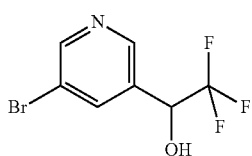 [SMILES: OC(c1cncc(Br)c1)C(F)(F)F]

To a cooled (0° C.) solution of 5-bromo-pyridine-3-carboxaldehyde (2.0 g, 10.8 mmol) in 25 mL of THF is added trimethyl(trifluoromethyl)silane (2.8 mL, 18.8 mmol) and 1.0M TBAF in THF solution (10.8 mL, 10.8 mmol). The mixture is warmed to room temperature for 3 hours. The solvent is evaporated to give the crude product. Purification by silica gel flash column chromatography affords 1.9 g of the title compound.

Intermediate 34:
4-Bromo-6,7-dihydro-5H-[2]pyrindin-7-ol

Step A: A solution of diisopropylamine (3.37 mL, 23.9 mmol) in 100 mL of THF is cooled to 0° C. and then treated with n-butyllithium (11.95 mL, 23.9 mmol). The mixture is stirred at 0° C. for 15 minutes then cooled to −78° C. Methyl 5-bromonicotinate (4.70 g, 21.7 mmol) is added as solution in 20 mL of THF drop-wise. The mixture is stirred at −78° C. for 30 minutes then treated with methyl acrylate (4.89 mL, 54.3 mmol) in 20 mL of THF drop-wise. The mixture is stirred at −78° C. for 1.5 hours then quenched with 50 mL of 10% acetic acid. The reaction mixture is evaporated to dryness. The crude solid is treated with 54 mL of 6N HCl and stirred at 100° C. for 1 hour. The reaction mixture is cooled in ice, basified to pH 7-8 with 5N NaOH and extracted twice with EtOAc. The combined org layer is washed with brine, dried over MgSO₄, filtered and concentrated. Purification by silica gel flash column chromatography eluting with 20-50% EtOAc/heptane affords 817 mg of 4-bromo-5,6-dihydro-[2]pyrindin-7-one.

Step B: A mixture of 4-bromo-5,6-dihydro-[2]pyrindin-7-one (1.96 g, 9.2 mmol) in 100 mL of ethanol is cooled to 0° C. and then treated with sodium borohydride (454.58 mg, 12.0 mmol). The reaction is stirred at room temperature for 1 hour and the solvent is evaporated. The crude solid is taken into EtOAc/water and the layers are separated. The org layer is washed with brine, dried over MgSO₄, filtered and concentrated. Purification by silica gel flash column chromatography eluting with 50-100% EtOAc/heptane affords 1.5 g of the title compound.

Synthesis of Final Compounds

Chiral SFC conditions for enantiomer resolution are set forth in Table 2. When absolute stereochemistry is not established, by definition, the first-eluting enantiomer is referred to as enantiomer A, and the second-eluting enantiomer is referred to as enantiomer B. Where a compound contains two stereocenters, the diastereomers are designated AA, AB, BA, and BB, with the first letter referring to the first resolved stereocenter and the second letter referring to the second resolved stereocenter in a given synthetic sequence, with A and B designations for order of elution as above. LCMS data are measured using the methods set forth in Table 3. LCMS Data for the compounds in Table 1 are shown in Table 4. Compounds that were separated into their enantiomers are shown by separate entries in Tables 4 and 5 for enantiomer A and enantiomer B Likewise, compounds that were separated into their diastereomers are shown by separate entries for diastereomers AA, AB, BA, and BB.

Example 1: 2-[5-(4-Hydroxy-tetrahydro-pyran-4-yl)-pyridin-3-yl]-2,3-dihydro-benzo[1,4]dioxine-5-carboxylic acid amide. (Cpd 1, Table 1)

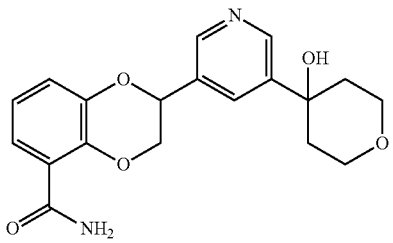 [SMILES: NC(=O)c1cccc2c1OCC(c1cncc(C3(O)CCOCC3)c1)O2]

Step A: 4-(5-Bromo-pyridin-3-yl)-tetrahydro-pyran-4-ol (516 mg, 2.0 mmol), bis(pinacolato)diboron (760 mg, 3.0 mmol), potassium acetate (785 mg, 8.0 mmol), and Bis(diphenylphosphino)ferrocene]dichloropalladium(II) (146 mg, 0.2 mmol) are combined in a vial. Dioxane (5 nit) is added and Ar is bubbled through the mixture for 5 minutes. The vial is capped and heated at 80° C. for 4 hours to provide 4-[5-(4,4,5,5-tetramethyl-[1,3,2]dioxaborolan-2-yl)-pyridin-3-yl]-tetrahydro-pyran-4-ol. This is used in situ for the subsequent Suzuki coupling.

Step B: To the above mixture of 4-[5-(4,4,5,5-tetramethyl-[1,3,2]dioxaborolan-2-yl)-pyridin-3-yl]-tetrahydro-pyran-4-ol is added 2-bromo-benzo[1,4]dioxine-5-carboxylic acid methyl ester (540 mg, 2.0 mmol), [1,1'-bis(diphenylphosphino)ferrocene]dichloropalladium(III) (146 mg, 0.2 mmol), and 2M aqueous sodium carbonate solution (2.0 ml, 4.0 mmol). Ar is bubbled through the mixture for 5 minutes. The vial is capped and heated at 80° C. for 16 hours. The reaction is cooled to room temperature and is poured into water. This is extracted three times with EtOAc. The combined organic extracts are washed with brine, dried (Na$_2$SO$_4$), filtered, and concentrated to dryness. The crude product is purified by silica gel flash chromatography eluting with 1-5% MeOH in DCM to provide 290 mg of 2-[5-(4-hydroxy-tetrahydro-pyran-4-yl)-pyridin-3-yl]-benzo[1,4]dioxine-5-carboxylic acid methyl ester.

Step C: A mixture of 2-[5-(4-hydroxy-tetrahydro-pyran-4-yl)-pyridin-3-yl]-benzo[1,4]dioxine-5-carboxylic acid methyl ester (100 mg, 0.3 mmol) and 10% palladium on carbon, Degussa type (50 mg) in 1 mL of acetic is degassed and placed under a balloon of hydrogen. The reaction is stirred at room temperature for 4 hours. The catalyst is filtered off and washed with methanol. The filtrate is concentrated to dryness. The residue is diluted with EtOAc and washed with 1N NaOH and brine. The EtOAc layer is dried (Na$_2$SO$_4$), filtered, and concentrated to dryness. The crude product is purified via silica gel flash column chromatography eluting with 1-5% MeOH in DCM to provide 60 mg of 2-[5-(4-hydroxy-tetrahydro-pyran-4-yl)-pyridin-3-yl]-2,3-dihydro-benzo[1,4]dioxine-5-carboxylic acid methyl ester.

Step D: A mixture of 2-[5-(4-hydroxy-tetrahydro-pyran-4-yl)-pyridin-3-yl]-2,3-dihydro-benzo[1,4]dioxine-5-carboxylic acid methyl ester (400 mg, 1.1 mmol) and 7 N ammonia in methanol solution (3 mL, 20 mmol) is heated in a sealed tube at 70° C. for 7 days. The reaction is concentrated to dryness. The residue is purified by flash chromatography on a Biotage KP-NH column (1-5% MeOH in DCM) to provide 300 mg of the title compound. The stereoisomers are separated using chiral SFC.

Compound 2 in Table 1 is synthesized according to the procedure outlined in Example 1, substituting either commercially available reagents or the appropriate intermediates described above.

Example 2: 2-[5-(1,1-Dioxo-1λ$^6$,-[1,2]thiazinan-2-ylmethyl)-pyridin-3-yl]-2,3-dihydro-benzo[1,4]dioxine-5-carboxylic acid amide (Cpd 3, Table 1)

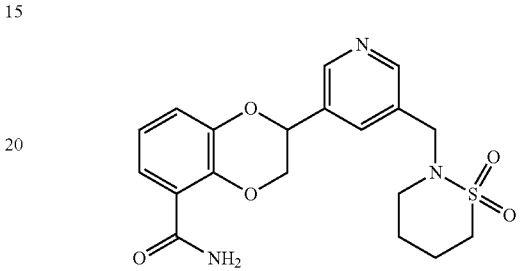

Step A: 2-(5-Bromo-pyridin-3-ylmethyl)-[1,2]thiazinane 1,1-dioxide (1.5 g, 5.0 mmol), bis(pinacolato)diboron (1.90 g, 7.5 mmol), potassium acetate (1.96 g, 20.0 mmol), [1,1'-bis(diphenylphosphino)ferrocene)dichloropalladium (II) (365.86 mg, 0.5 mmol) and 16 mL of 1,4-dioxane are combined in a reaction vessel. The vessel is flushed with argon and sealed. The mixture is stirred at 120° C. for 2 hours and cooled to room temperature.

Step B: 2-Bromo-benzo[1,4]dioxine-5-carboxylic acid methyl ester (1.00 g, 3.7 mmol) is added to the reaction mixture from step A, followed by 5.0 mL of 1,4-dioxane and 2M aqueous sodium carbonate (3.7 mL, 7.4 mmol). The vessel is flushed with argon and sealed. The mixture is stirred at 100° C. for 16 hours. The reaction mixture is diluted with EtOAc and water and filtered through diatomaceous earth. The layers are separated and the organic layer is washed with brine, dried over MgSO$_4$, filtered and concentrated. The crude product is purified by silica gel flash column chromatography eluting with EtOAc to give 1.1 g of dioxo-1λ$^6$,-[1,2]thiazinan-2-ylmethyl)-pyridin-3-yl]-benzo[1,4]dioxine-5-carboxylic acid methyl ester.

Step C: 2-[5-(1,1-Dioxo-1λ$^6$,-[1,2]thiazinan-2-ylmethyl)-pyridin-3-yl]-benzo[1,4]dioxine-5-carboxylic acid methyl ester (1.1 g, 2.6 mmol) and 7N ammonia in MeOH solution (18.6 ml, 130.3 mmol) are combined in pressure vessel. The vessel is sealed and stirred at 85° C. for 16 hours. The resulting gray solid is filtered to give 656 mg of 2-[5-(1,1-dioxo-1λ$^6$,-[1,2]thiazinan-2-ylmethyl)-pyridin-3-yl]-benzo[1,4]dioxine-5-carboxylic acid amide.

Step D: 2-[5-(1,1-Dioxo-1λ$^6$,-[1,2]thiazinan-2-ylmethyl)-pyridin-3-yl]-benzo[1,4]dioxine-5-carboxylic acid amide (630 mg, 1.6 mmol), 50 mL of acetic acid and 10% palladium on carbon (167 mg, 0.16 mmol) are combined. The mixture is stirred under an atmosphere of hydrogen for 3 hours at room temperature and the reaction mixture is filtered through diatomaceous earth. The filtrate is concentrated and the crude solid is purified by silica gel flash column chromatography eluting with 50-100% EtOAc/10% MeOH/EtOAc to give 375 mg of the title compound. The stereoisomers are separated by chiral SFC.

Compounds 4 through 27 and compounds 51 and 59 in Table 1 are synthesized according to the procedure for Example 2, substituting either commercially available reagents or the appropriate intermediates described above.

Compound 28 in Table 1 is synthesized according to the procedure for Example 2, substituting the appropriate commercially available reagent and 33% methylamine in ethanol for ammonia in methanol in Step C.

Example 3: 2-[5-[2-(Dimethylamino)-2-oxo-ethyl]-3-pyridyl]-2,3-dihydro-1,4-benzodioxine-5-carboxamide (Cpd 29, Table 1)

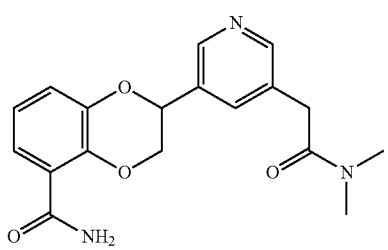 [SMILES: CN(C)C(=O)Cc1cncc(C2COc3c(cccc3C(N)=O)O2)c1]

Step A: 2-(5-Bromo-3-pyridyl)-N,N-dimethyl-acetamide (0.8 g, 3.3 mmol), bis(pinacolato)diboron (1.0 g, 4.1 mmol), potassium acetate (1.3 g, 13.2 mmol), [1,1'-bis(diphenylphosphino)ferrocene)dichloropalladium(II) (0.24 g, 0.3 mmol) and 37 mL of 1,4-dioxane are combined in a pressure vessel. The vessel is flushed with argon and sealed. The mixture is stirred at 120° C. for 45 minutes and cooled to room temperature.

Step B: 2-Bromo-1,4-benzodioxine-5-carboxamide (0.9 g, 3.6 mmol), [1,1'-bis(diphenylphosphino)ferrocene)dichloropalladium(II) (0.12 g, 0.17 mmol), and 2M aqueous sodium carbonate (3.3 mL, 6.6 mmol) are added to the reaction mixture from step A. The vessel is flushed with argon and sealed. The mixture is stirred at 100° C. for 2 hours. The mixture is filtered through diatomaceous earth and rinsed with 10% MeOH in DCM (150 mL). The filtrate is concentrated. The resulting crude product is purified by silica gel flash column chromatography eluting with 0-6% MeOH in DCM as the gradient to afford 0.39 g of 2-[5-[2-(dimethylamino)-2-oxo-ethyl]-3-pyridyl]-1,4-benzodioxine-5-carboxamide.

Step C: To a pre-degassed solution of 2-[5-[2-(dimethylamino)-2-oxo-ethyl]-3-pyridyl]-1,4-benzodioxine-5-carboxamide (0.62 g, 1.8 mmol) in 49 mL of acetic acid is added 124 mg of 10 wt % palladium on carbon. The resulting mixture is evacuated and back-filled with $H_2$ (repeated twice). The mixture is then hydrogenated for 2 hours. The mixture is filtered through diatomaceous earth and rinsed with EtOAc. The filtrate is concentrated. The resulting residue is re-dissolved in EtOAc. Saturated NaHCO$_3$ solution (20 mL) and water (10 mL) are added. The two layers are separated. The aqueous layer is extracted with EtOAc (4×50 mL). The combined organic layers are dried over sodium sulfate, filtered, and concentrated. The resulting crude product is purified by silica gel flash column chromatography eluting with 0-10% MeOH in DCM to afford 0.43 g of 2-[5-[2-(dimethylamino)-2-oxo-ethyl]-3-pyridyl]-2,3-dihydro-1,4-benzodioxine-5-carboxamide. The stereoisomers are separated by chiral SFC.

Compounds 30 through 32 in Table 1 are synthesized according to the procedure for Example 3, substituting either commercially available reagents or the appropriate intermediates described above.

Compound 33 in Table 1 is synthesized according to the procedure for Example 3, substituting 2-bromo-benzo[1,4]dioxine-5-carboxylic acid methylamide for 2-bromo-1,4-benzodioxine-5-carboxamide in Step B.

Example 4: 2-[5-(2-Oxo-oxazolidin-3-ylmethyl)-pyridin-3-yl]-2,3-dihydro-benzo[1,4]dioxine-5-carbonitrile (Cpd 34, Table 1)

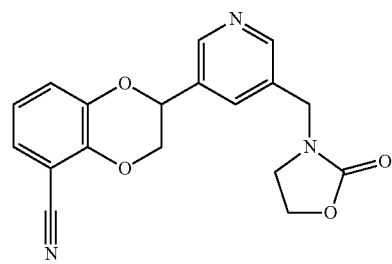 [SMILES: N#Cc1cccc2c1OCC(c1cncc(CN3CCOC3=O)c1)O2]

To a solution of 2-[5-(2-oxo-oxazolidin-3-ylmethyl)-pyridin-3-yl]-2,3-dihydro-benzo[1,4]dioxine-5-carboxylic acid amide, compound 31, enantiomer A (35 mg, 0.10 mmol) in 2.0 mL of 1,4-dioxane is added pyridine (0.16 mL, 1.97 mmol) followed by trifluoroacetic anhydride (0.14 mL, 0.98 mmol). After 5 minutes, the reaction is poured into 7.5 mL of water and 7.5 mL of saturated NaHCO$_3$ solution. The product is extracted into EtOAc (2×) and the combined organics are washed once with water and then dried (MgSO$_4$). The organic is filtered and concentrated to give the crude product which is purified via flash column chromatography on a Biotage KP-NH column eluting with methanol in DCM to afford 25 mg of the title compound.

Compounds 35 through 43 in Table 1 are synthesized according to the procedure for Example 4, substituting the appropriate compounds described above. Chiral SFC is utilized for enantiomer resolution for examples synthesized from racemic starting materials, and conditions can be found in Table 2. All other examples are prepared from enantiomerically pure starting materials.

Compound 44 in table 1 is synthesized according to the procedures in Example 2 and Example 4, substituting the appropriate intermediate described above.

Example 5: 2-(5-Ethoxy-pyridin-3-yl)-2,3-dihydrobenzo[1,4]dioxine-5-carboxylic acid amide (Cpd 45, Table 1)

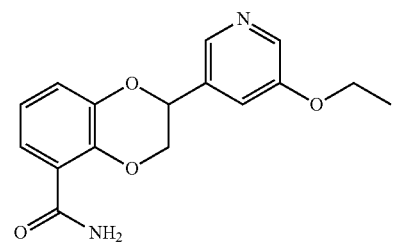 [SMILES: CCOc1cncc(C2COc3c(cccc3C(N)=O)O2)c1]

Step A: 2-(5-Benzyloxy-pyridin-3-yl)-benzo[1,4]dioxine-5-carboxylic acid methyl ester is synthesized from 3-benzyloxy-5-bromo-pyridine and 2-bromo-benzo[1,4]dioxine-5-carboxylic acid methyl ester according to the method of Example 2, steps A and B.

Step B: 2-(5-Benzyloxy-pyridin-3-yl)-benzo[1,4]dioxine-5-carboxylic acid methyl ester (500 mg, 1.3 mmol) is dissolved in 10 mL of DCM and 10 mL of methanol. Then 5% Pd on carbon (280 mg, 0.13 mmol) is added. A hydrogen balloon is attached to the reaction flask and the mixture is stirred under hydrogen atmosphere for 1.5 hours. Then the mixture is filtered and the filtrate is concentrated to give 375 mg of 2-(5-hydroxy-pyridin-3-yl)-2,3-dihydro-benzo[1,4]dioxine-5-carboxylic acid methyl ester.

Step C: Ethanol (0.041 mL, 0.70 mmol), 2-(5-hydroxy-pyridin-3-yl)-2,3-dihydro-benzo[1,4]dioxine-5-carboxylic acid methyl ester (100 mg, 0.35 mmol) and triphenylphosphine (180 mg, 0.70 mmol) are dissolved in 3.0 mL of THF and diisopropyl azodicarboxylate (0.14 mL, 0.70 mmol) is added. The mixture is stirred for 5 hours and the solvent is removed. The residue is purified by flash column chromatography on silica gel to give 79 mg of 2-(5-ethoxy-pyridin-3-yl)-2,3-dihydro-benzo[1,4]dioxine-5-carboxylic acid methyl ester.

Step D: Lithium hydroxide monohydrate (21 mg, 0.50 mmol) is dissolved in 1.0 mL of water and this solution is added into 2-(5-ethoxy-pyridin-3-yl)-2,3-dihydro-benzo[1,4]dioxine-5-carboxylic acid methyl ester (79 mg, 0.25 mmol) solution in 2.0 mL of 1,4-dioxane. The mixture is stirred for 64 hours and 0.3 mL of acetic acid is added. Then all the solvents are removed and 25 mL of water is added. A solid is formed and it is filtered, rinsed with more water and dried to give 71 mg of 2-(5-ethoxy-pyridin-3-yl)-2,3-dihydro-benzo[1,4]dioxine-5-carboxylic acid.

Step E: 2-(5-Ethoxy-pyridin-3-yl)-2,3-dihydro-benzo[1,4]dioxine-5-carboxylic acid (71 mg, 0.24 mmol) is dissolved in 2.0 mL of DMF and 1,1'-carbonyldiimidazole (77 mg, 0.48 mmol) is added. The mixture is heated at 60° C. for 1 hour and it is then cooled down to room temperature. Then 28% ammonium hydroxide aqueous solution (0.33 mL, 2.4 mmol) is added and the mixture is stirred for another hour. Then 25 mL of water is added and a solid is formed. The solid is filtered, rinsed with more water and dried to give 53 mg of the titled product. Enantiomers of the titled compound are separated using chiral SFC.

Compounds 46 and 47 in Table 1 are synthesized according to the procedure for Example 5, substituting ethanol in Step C with the appropriate commercially available alcohols.

Example 6: 2-[5-(1-isobutyryl-piperidin-4-yloxy)-pyridin-3-yl]-2,3-dihydro-benzo[1,4]dioxine-5-carboxylic acid amide (Cpd 48, Table 1)

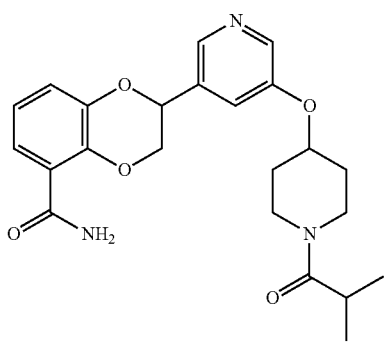

Step A: 4-[5-(5-Methoxycarbonyl-2,3-dihydro-benzo[1,4]dioxin-2-yl)-pyridin-3-yloxy]-piperidine-1-carboxylic acid tert-butyl ester is synthesized according to Example 5, Step A to Step C, substituting ethanol in Step C with commercially available 4-hydroxy-piperidine-1-carboxylic acid tert-butyl ester.

Step B: 4-[5-(5-Methoxycarbonyl-2,3-dihydro-benzo[1,4]dioxin-2-yl)-pyridin-3-yloxy]-piperidine-1-carboxylic acid tert-butyl ester (380 mg, 0.80 mmol) is dissolved in 5.0 mL of DCM and 1.0 mL of trifluoroacetic acid is added. The mixture is stirred for 2 hours and all the solvent is removed. EtOAc (30 mL) is added along with 10 mL of saturated aqueous solution of $NaHCO_3$. The mixture is stirred for 10 min and the aqueous layer is separated and extracted with EtOAc. The organic layers are combined and concentrated to give 300 mg of 2-[5-(piperidin-4-yloxy)-pyridin-3-yl]-2,3-dihydro-benzo[1,4]dioxine-5-carboxylic acid methyl ester.

Step C: 2-[5-(Piperidin-4-yloxy)-pyridin-3-yl]-2,3-dihydro-benzo[1,4]dioxine-5-carboxylic acid methyl ester (300 mg, 0.80 mmol) is dissolved in 5.0 mL of DCM. Then isobutyryl chloride (0.16 mL, 1.52 mmol) and triethyl amine (0.28 mL, 2.04 mmol) are added. After the mixture is stirred for 16 hours, 5 mL of saturated aqueous solution of $NaHCO_3$ (5 mL) is added along with 15 mL of water and 15 mL of DCM. The mixture is stirred for 10 minutes and the aqueous layer is separated and extracted with DCM. The organic layers are combined and concentrated to give the crude product. Purification by flash column chromatography on silica gel affords 160 mg of 2-[5-(1-isobutyryl-piperidin-4-yloxy)-pyridin-3-yl]-2,3-dihydro-benzo[1,4]dioxine-5-carboxylic acid methyl ester.

Step D: Lithium hydroxide monohydrate (30 mg, 0.73 mmol) is dissolved in 1.0 mL of water and this solution is added into 2-[5-(1-isobutyryl-piperidin-4-yloxy)-pyridin-3-yl]-2,3-dihydro-benzo[1,4]dioxine-5-carboxylic acid methyl ester (160 mg, 0.36 mmol) solution in 2.0 mL of 1,4-dioxane. The mixture is stirred for 64 hours and 3 mL of acetic acid is added along with 20 mL of EtOAc and 20 mL of water. The aqueous layer is separated and extracted with EtOAc. All the organic layers are combined and concentrated to give 110 mg of 2-[5-(1-isobutyryl-piperidin-4-yloxy)-pyridin-3-yl]-2,3-dihydro-benzo[1,4]dioxine-5-carboxylic acid.

Step E: 2-[5-(1-Isobutyryl-piperidin-4-yloxy)-pyridin-3-yl]-2,3-dihydro-benzo[1,4]dioxine-5-carboxylic acid (110 mg, 0.26 mmol) is dissolved in 2.0 mL of DMF and 1,1'-carbonyldiimidazole (84 mg, 0.52 mmol) is added. The mixture is heated at 60° C. for 1 hour and it is then cooled down to room temperature. Then 28% ammonium hydroxide aqueous solution (0.36 mL, 2.6 mmol) is added and the mixture is stirred for another hour. Then 25 mL of water is added and a solid is formed. The solid is filtered, rinsed with more water and dried to give 75 mg of the titled product. Enantiomers of the titled compound are separated using chiral SFC.

Example 7: 2-[5-(2,2,2-Trifluoro-1-hydroxy-ethyl)-pyridin-3-yl]-2,3-dihydro-benzo[1,4]dioxine-5-carboxylic acid amide (Cpd 49, Table 1)

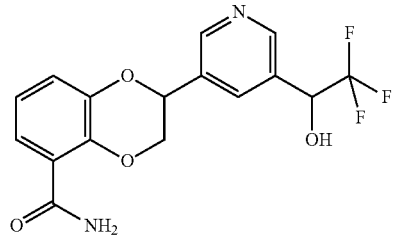 [SMILES: NC(=O)c1cccc2c1OCC(c1cncc(C(O)C(F)(F)F)c1)O2]

Step A: 2-[5-(2,2,2-Trifluoro-1-hydroxy-ethyl)-pyridin-3-yl]-benzo[1,4]dioxine-5-carboxylic acid amide is prepared from 1-(5-bromo-pyridin-3-yl)-2,2,2-trifluoro-ethanol and 2-bromo-benzo[1,4]dioxine-5-carboxylic acid methyl ester according, to Example 2, Step A through Step C. Enantiomers are separated using. Chiral SEC (LUX Celluse-2, 30% (1:1:1 MeOH:EtOH:i-PrOH+0.1% DEA):CO$_2$, 70 mL/min, 120 bar, 35° C.).

Step B: 2-[5-(2,2,2-Trifluoro-1-hydroxy-ethyl)-pyridin-3-yl]-benzo[1,4]dioxine-5-carboxylic acid amide, enantiomer A (125 mg, 0.36 mmol) is hydrogenated according to Example 2, Step D to give 90 mg of product. Chiral SFC of this material delivers 14 mg of 49AA and 14 mg of 49AB.

Step C: 2-[5-(2,2,2-Trifluoro-1-hydroxy-ethyl)-pyridin-3-yl]-benzo[1,4]dioxine-5-carboxylic acid amide, enantiomer B (120 mg, 0.34 mmol) is hydrogenated according to Example 2, Step D to give 90 mg of product. Chiral SFC of this material delivers 13 mg of 49BA and 15 mg of 49BB.

Example 8: 2-[5-(4-Hydroxy-tetrahydro-pyran-4-yl)-pyridin-3-yl]-2,3-dihydro-benzo[1,4]dioxine-5-carbonitrile, (Cpd 50, Table 1)

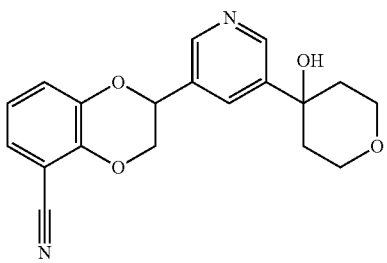 [SMILES: N#Cc1cccc2c1OCC(c1cncc(C3(O)CCOCC3)c1)O2]

A mixture of 2-[5-(4-hydroxy-tetrahydro-pyran-4-yl)-pyridin-3-yl]-2,3-dihydro-benzo[1,4]dioxine-5-carboxylic acid amide, enantiomer B (40 mg, 0.1 mmol) and Palladium (II) chloride (20 mg, 0.1 mmol) in 1 mL of 1:1 ACN:Water is heated in a sealed vial at 50° C. for 16 hours. The mixture is allowed to cool and water is added. The resultant precipitate is filtered off and dried. The solid is dissolved in 10% water in DMSO and is purified by prep HPLC. Fractions are concentrated to dryness to provide 8 mg of the title compound.

Example 9: 2-(7-Hydroxy-6,7-dihydro-5H-[2]pyrindin-4-yl)-2,3-dihydro-benzo[1,4]dioxine-5-carboxylic acid amide (Cpd 52, Table 1)

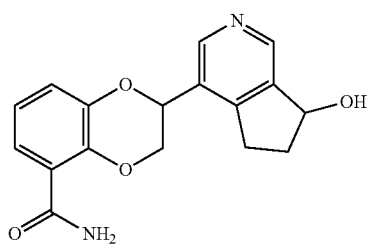

Step A: 2-(7-Hydroxy-6,7-dihydro-5H-[2]pyrindin-4-yl)-benzo[1,4]dioxine-5-carboxylic acid methyl ester is synthesized from 4-bromo-6,7-dihydro-5H-[2]pyrindin-7-ol and 2-bromo-benzo[1,4]dioxine-5-carboxylic acid methyl ester according to Example 2, Steps A and B, Enantiomers are separated using SFC (LUX Cellulose-1, 45% (MeOH)CO$_2$, 125 mL/min, 120 bar, 40° C.).

Step B: 2-(7-Hydroxy-6,7-dihydro-5H-[2]pyrindin-4-yl)-benzo[1,4]dioxine-5-carboxylic acid methyl ester, enantiomer A is converted into the title compound, according to Example 2, Steps C and D. Chiral SFC gives 52AA and 52AB.

Step C: 2-(7-Hydroxy-6,7-dihydro-5H-[2]pyrindin-4-yl)-benzo[1,4]dioxine-5-carboxylic acid methyl ester, enantiomer B is converted into the title compound, according to Example 2, Steps C and D. Chiral separation using SFC gives 52BA and 52BB.

Example 10: N-[5-(5-Cyano-2,3-dihydro-benzo[1,4]dioxin-2-yl)-pyridin-3-ylmethyl]-2,2,2-trifluoro-acetamide (Cpd 53, Table 1) and ethanesulfonic acid [5-(5-cyano-2,3-dihydro-benzo[1,4]dioxin-2-yl)-pyridin-3-ylmethyl]-amide (54, Table 1)

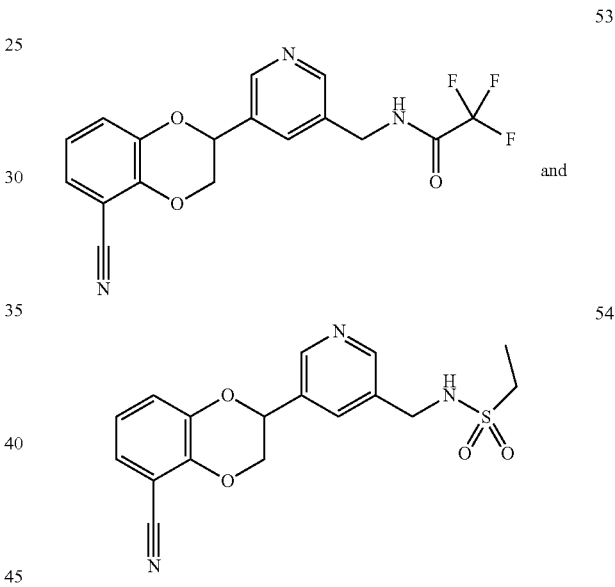

Step A: 2-Bromo-benzo[1,4]dioxine-5-carboxylic acid methyl ester and (5-bromo-pyridin-3-ylmethyl)-carbamic acid tert-butyl ester are converted to [5-(5-carbamoyl-2,3-dihydro-benzo[1,4]dioxin-2-yl)-pyridin-3-ylmethyl]-carbamic acid tert-butyl ester according to Example 2, Step A through Step D.

Step B: [5-(5-Carbamoyl-2,3-dihydro-benzo[1,4]dioxin-2-yl)-pyridin-3-ylmethyl]-carbamic acid tert-butyl ester is converted to [5-(5-cyano-2,3-dihydro-benzo[1,4]dioxin-2-yl)-pyridin-3-ylmethyl]-carbamic acid tert-butyl ester according to Example 4.

Step C: [5-(5-Cyano-2,3-dihydro-benzo[1,4]dioxin-2-yl)-pyridin-3-ylmethyl]-carbamic acid tert-butyl ester (140 mg, 0.4 mmol) is dissolved in 5 mL of DCM. Trifluoroacetic acid (0.5 mL) is added and the reaction mixture is stirred at room temperature for 2 hours. The solvent is removed to give 100 mg of 2-(5-aminomethyl-pyridin-3-yl)-2,3-dihydro-benzo[1,4]dioxine-5-carbonitrile. Crude 2-(5-aminomethyl-pyridin-3-yl)-2,3-dihydro-benzo[1,4]dioxine-5-carbonitrile (100 mg, 0.4 mmol) containing residual trifluoroacetic acid is dissolved in 5 mL of THF. N,N-Diisopropylethylamine (0.12 mL, 0.8 mmol) and ethanesulfonyl chloride (75 μL, 0.8 mmol) are added. The reaction mixture is stirred at room temperature for two hours. It is then concentrated to dryness and is purified by flash chromatography on a Biotage KP-NH column eluting with EtAOc in heptanes to give 26 mg of 53 and 40 mg of ethanesulfonic acid [5-(5-cyano-2,3-dihydro-benzo[1,4]dioxin-2-yl)-pyridin-3-ylmethyl]-amide (54). Enantiomers of 54 are separated using chiral SFC.

Example 11: 2-{5-[2-((R)-3-Hydroxy-pyrrolidin-1-yl)-2-oxo-ethyl]-pyridin-3-yl}-2,3-dihydro-benzo[1,4]dioxine-5-carbonitrile (Cpd 55, Table 1)

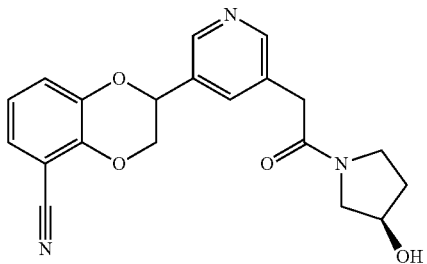 [SMILES: N#Cc1cccc2c1OCC(c1cncc(CC(=O)N3CC[C@@H](O)C3)c1)O2]

Step A: Trifluoro-methanesulfonic acid (R)-3-{2-[5-(5-cyano-2,3-dihydro-benzo[1,4]dioxin-2-yl)-pyridin-3-yl]-acetyl}-cyclopentyl ester is prepared from 2-(5-bromo-pyridin-3-yl)-1-((R)-3-hydroxy-pyrrolidin-1-yl)-ethanone and 2-bromo-benzo[1,4]dioxine-5-carboxylic acid methyl ester according to Example 2, Step A through Step D and Example 4.

Step B: To Trifluoro-methanesulfonic acid (R)-3-{2-[5-(5-cyano-2,3-dihydro-benzo[1,4]dioxin-2-yl)-pyridin-3-yl]-acetyl}-cyclopentyl ester (140 mg, 0.30 mmol) in 5 mL of 1:1 THF:water is added lithium hydroxide (72 mg, 3.0 mmol). The reaction is stirred at room temperature for 16 hours. The reaction is concentrated to dryness and the residue is partitioned between EtOAc and water. The EtOAc layer is concentrated to dryness and the residue is purified by silica gel chromatography to give 90 mg of the racemic title compound. Enantiomers of 55 are separated using chiral SFC.

Example 12: 2-[5-Fluoro-4-((S)-1-hydroxy-ethyl)-pyridin-3-yl]-2,3-dihydro-benzo[1,4]dioxine-5-carboxylic acid amide (Cpd 56, Table 1)

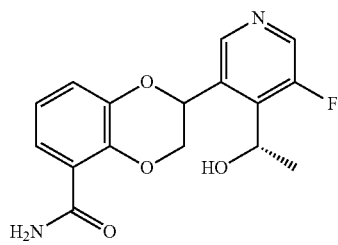

Step A: 3-Bromo-5-fluoro-pyridine (13 g, 74 mmol) is dissolved in 140 mL of dry THF and cooled down to −78° C. LDA solution (44 mL, 2.0 M in THF, 88 mmol) is added and the mixture is stirred for 2 hours at −78° C. Then acetaldehyde solution (30 mL, 5.0 M in THF, 150 mmol) is added at −78° C. and the reaction is continued for another 30 minutes. Then saturated aqueous $NH_4Cl$ solution (200 mL) is added and the mixture is warmed up to room temperature. EtOAc (100 mL) is added along with 75 mL of water. The aqueous layer is separated and extracted with EtOAc (2×75 mL). The organic layers are combined and concentrated to give the crude product. Purification by flash column chromatography affords 14 g of the racemic product. Chiral separation of the racemic product using chiral SFC affords 6.5 g of (R)-1-(3-bromo-5-fluoro-pyridin-4-yl)-ethanol and 6.4 g of (S)-1-(3-bromo-5-fluoro-pyridin-4-yl)-ethanol.

Step B: A solution of (S)-1-(3-bromo-5-fluoro-pyridin-4-yl)-ethanol (1.62 g, 7.4 mmol) in 25 mL of THF is cooled to 0° C. and 60% sodium hydride (736.23 mg, 18.4 mmol) is then added. The mixture is stirred at 0° C. for 1 hour then cooled to −78° C. n-Butyllithium 1.08 M in hexanes (10.23 mL, 11.0 mmol) is added, followed by triisopropyl borate (2.55 mL, 11.0 mmol). The cooling bath is removed and the mixture is stirred at room temperature for 16 hours. The reaction mixture is cooled to 0° C. and then quenched with 5.0 mL of 1:1 solution of conc. $H_2SO_4$:water. The mixture is stirred at room temperature for 1 hour. The organic solvent is evaporated and the aqueous layer is then neutralized to pH 6-7. The aqueous layer is extracted with EtOAc (3×) and the combined organic layers are washed with brine, dried over $MgSO_4$, filtered and concentrated to give crude (S)-4-fluoro-3-methyl-2-oxa-6-aza-1-bora-indan-1-ol.

Step C: 2-Bromo-benzo[1,4]dioxine-5-carboxylic acid methyl ester (1.0 g, 3.7 mmol), crude (5)-4-fluoro-3-methyl-2-oxa-6-aza-1-bora-indan-1-ol (924 mg, 5.5 mmol), [1,1'-bis(diphenylphosphino)ferrocene)dichloropalladium(II) DCM complex (150.63 mg, 0.18 mmol), 1,4-dioxane (15.00 ml) and 2.0M $Na_2CO_3$ aqueous solution (3.69 mL, 7.4 mmol) are added to a pressure vessel. The vessel is flushed with argon, sealed and stirred at 100° C. for 2 hours. The reaction mixture is cooled to room temperature, diluted with EtOAc and 25 mL of water and the mixture is filtered on diatomaceous earth. The layers of the filtrate are separated and the organic layer is washed with brine, dried over $MgSO_4$, filtered and concentrated. Purification by silica gel flash column chromatography eluting with 50-100% EtOAc/heptane) to give 659 mg of 2-[5-fluoro-4-((S)-1-hydroxy-ethyl)-pyridin-3-yl]-benzo[1,4]dioxine-5-carboxylic acid methyl ester.

Step D: 2-[5-Fluoro-4-((S)-1-hydroxy-ethyl)-pyridin-3-yl]-benzo[1,4]dioxine-5-carboxylic acid methyl ester is converted to the title compound according to Example 2, Steps C and D. The benzodiozane enantiomers are separated by chiral SFC.

Compound 57 in Table 1 is synthesized according to the procedure for Example 12, substituting (R)-1-(3-bromo-5-fluoro-pyridin-4-yl)-ethanol in Step B.

Example 13: 2-[5-Fluoro-4-(1-hydroxy-1-methyl-ethyl)-pyridin-3-yl]-2,3-dihydro-benzo[1,4]dioxine-5-carboxylic acid amide (Cpd 58, Table 1)

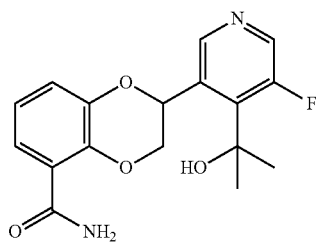 [SMILES: CC(C)(O)c1c(F)cncc1C1COc2c(cccc2C(N)=O)O1]

Step A: To a solution of 2-[5-fluoro-4-(1-hydroxy-ethyl)-pyridin-3-yl]-2,3-dihydro-benzo[1,4]dioxine-5-carboxylic acid amide (cpd 57) (632.00 mg, 2.0 mmol), and Dess-Martin periodinane (1.01 g, 2.4 mmol) in 35 mL of acetonitrile is added trifluoroacetic acid (0.15 mL, 2.0 mmol). The heterogenous mixture is stirred at room temperature for 2 days. The reaction mixture is diluted with 150 mL of 15% MeOH/DCM. 1N NaOH and 2M $Na_2S_2O_3$ are added and the mixture is filtered. The layers are separated, and the organic layer is concentrated. Purification by silica gel flash column chromatography eluting with 50-100% EtOAc/heptane gives 550 mg of 2-(4-acetyl-5-fluoro-pyridin-3-yl)-2,3-dihydro-benzo[1,4]dioxine-5-carboxylic acid amide.

Step B: A solution of 2-(4-acetyl-5-fluoro-pyridin-3-yl)-2,3-dihydro-benzo[1,4]dioxine-5-carboxylic acid amide (440.00 mg, 1.4 mmol) in 44 mL of THF is cooled to 0° C. and then treated with 2.0 M methylmagnesium bromide solution in THF (2.3 mL, 6.6 mmol). The mixture is stirred at 0° C. for 30 minutes. The reaction mixture is quenched with saturated aqueous $NH_4Cl$ solution and diluted with EtOAc/water. The aqueous layer is separated, and back-extracted with EtOAc. The combined organic layers are washed with brine, dried over $MgSO_4$, filtered and concentrated. Purification by column chromatography on a Biotage KP-NH column eluting with 50-100% EtOAc gives 125 mg of the title compound. Enantiomers are separated using chiral SFC.

Example 14: 2-[5-(Cyclopropyl-ethanesulfonylamino-methyl)-pyridin-3-yl]-benzo[1,4]dioxine-5-carboxylic acid amide (Cpd 60, Table 1)

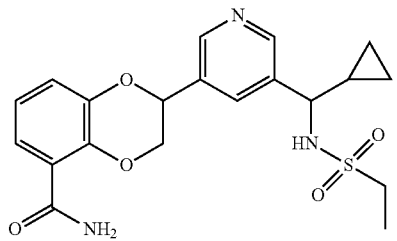

Step A: To a mixture of 5-bromonicotinaldehyde (0.50 g, 2.69 mmol) and ethanesulfonamide (0.37 g, 3.36 mmol) in 9.0 mL of toluene is added titanium(IV) isopropoxide (1.59 mL, 5.4 mmol). The reaction mixture is stirred at 120° C. for 3 hours after which time it is concentrated to dryness. The remaining residue is dissolved in 10 mL of THF and cooled to −40° C. Cyclopropylmagnesium bromide (16.13 mL, 8.1 mmol) is added drop-wise and the reaction mixture is allowed to gradually warm to room temperature. After 16 hours, the reaction mixture is diluted with EtOAc and washed with saturated aqueous $NH_4Cl$ solution then brine. The organic layer is dried ($MgSO_4$), filtered and concentrated. The remaining residue is purified via silica gel flash column chromatography eluting with 0-5% MeOH/DCM to give 0.59 g of ethanesulfonic acid [(5-bromo-pyridin-3-yl)-cyclopropyl-methyl]amide.

Step B: Ethanesulfonic acid [(5-bromo-pyridin-3-yl)-cyclopropyl-methyl]-amide and 2-bromo-benzo[1,4]dioxine-5-carboxylic acid methyl ester are converted to 2-[5-(cyclopropyl-ethanesulfonylamino-methyl)-pyridin-3-yl]-benzo[1,4]dioxine-5-carboxylic acid amide according to Example 2, Steps A-C. Enantiomers are separated using SEC (Regis S,S) Whelk-O 1, 40% (EtOH+1% Isopropylamine):$CO_2$, 80 mL/min, 100 bar, 25° C.).

Step C: 2-[5-(Cyclopropyl-ethanesulfonylamino-methyl)-pyridin-3-yl]-benzo[1,4]dioxine-5-carboxylic acid amide, enantiomer A is hydrogenated according to Example 2, Step D. Chiral SFC yields 60AA and 60AB.

Step D: 2-[5-(Cyclopropyl-ethanesulfonylamino-methyl)-pyridin-3-yl]-benzo[1,4]dioxine-5-carboxylic acid amide, enantiomer B is hydrogenated according to Example 2, Step D. Chiral SFC yield 60BA and 60BB.

Example 15: 2-(5-Cyano-4-methyl-pyridin-3-yl)-2,3-dihydro-benzo[1,4]dioxine-5-carboxylic acid amide (Cpd 61, Table 1)

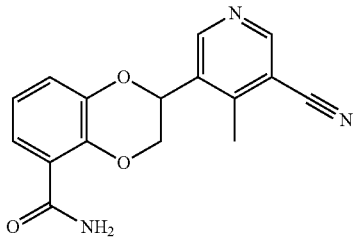 [SMILES: Cc1c(C#N)cncc1C1COc2c(cccc2C(N)=O)O1]

Step A: To a stirred suspension of 5-bromo-4-methyl-nicotinic acid (1.75 g, 8.10 mmol) in 20 mL of DMF is added CDI (1.97 g, 12.2 mmol). The mixture is warmed at 65° C. for 0.75 hour after which time it is cooled to room temperature and treated with ammonium hydroxide (10.1 ml, 81.0 mmol). After stirring for 2 hours the reaction is poured into water (150 ml) and the product is extracted into EtOAc (3×). The combined organics are dried ($MgSO_4$), filtered and concentrated. The crude residue is purified via silica gel flash column chromatography eluting with 0-6% MeOH/DCM to afford 1.4 g of 5-bromo-4-methyl-nicotinamide.

Step B: 5-Bromo-4-methyl-nicotinamide and 2-bromo-benzo[1,4]dioxine-5-carboxylic acid methyl ester are converted to 2-(5-carbamoyl-4-methyl-pyridin-3-yl)-2,3-dihydro-benzo[1,4]dioxine-5-carboxylic acid methyl ester according to Example 1, Steps A-C Step C: To a stirred solution of 2-(5-carbamoyl-4-methyl-pyridin-3-yl)-2,3-dihydro-benzo[1,4]dioxine-5-carboxylic acid methyl ester (180 mg, 0.55 mmol) in 10.0 mL of 1,4-dioxane and pyridine (0.89 ml, 10.9 mmol) is added trifluoroacetic anhydride (0.77 ml, 5.5 mmol) in a drop-wise manner over 10 minutes. Upon complete addition the reaction is stirred for 5 minutes after which time it is poured into water and $NaHCO_3$ (sat., 1:1, 150 mL). The mixture is diluted with EtOAc and the layers are separated. The organic layer is washed once with water and then dried ($MgSO_4$). Filtration and concentration gave 160 mg of 2-(5-cyano-4-methyl-pyridin-3-yl)-2,3-dihydro-benzo[1,4]dioxine-5-carboxylic acid methyl ester.

Step D: A suspension of 2-(5-cyano-4-methyl-pyridin-3-yl)-2,3-dihydro-benzo[1,4]dioxine-5-carboxylic acid methyl ester (160 mg, 0.52 mmol) in 7N ammonia in methanol (5.0 ml, 35.0 mmol) is warmed to 85° C. After 24 hours the reaction is cooled to room temperature and concentrated. The remaining crude is purified via flash column chromatography on a Biotage KP-NH column eluting with DCM to give 70 mg of the title compound. Enantiomers were separated using SFC.

Example 16: 2-(5-{[Imino(methyl)oxo-λ$^6$-sulfanyl]methyl}pyridine-3-yl)-2,3-dihydro-1,4-benzodioxine-5-carbonitrile (Cpd 62, Table 1)

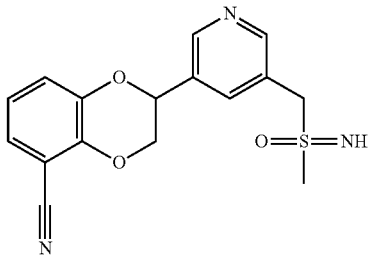 [SMILES: CS(=N)(=O)Cc1cncc(C2COc3c(C#N)cccc3O2)c1]

Step A: (2-(5-Hydroxymethyl-pyridin-3-yl)-2,3-dihydro-benzo[1,4]dioxine-5-carboxylic acid methyl ester is synthesized from (5-bromo-pyridin-3-yl)-methanol and 2-bromo-benzo[1,4]dioxine-5-carboxylic acid methyl ester according to Example 1, steps A through C. Enantiomers are separated by chiral SFC (Chiracel-OJ-H, 0.5% DEA in methanol, 100 mL/min, 100 bar, 25° C.).

Step B: To a cooled (0° C.) solution of (2-(5-hydroxymethyl-pyridin-3-yl)-2,3-dihydro-benzo[1,4]dioxine-5-carboxylic acid methyl ester, enantiomer B (1.80 g, 6.0 mmol) and triphenylphosphine (1.88 g, 7.2 mmol) in 50 mL of DCM is added carbon tetrabromide (2.38 g, 7.2 mmol). The reaction is stirred for 30 minutes after which time the mixture is concentrated in vacuo. The crude residue is purified by silica gel flash column chromatography eluting with 10-100% EtOAc/heptane to give 1.3 g of 2-(5-bromomethyl-pyridin-3-yl)-2,3-dihydro-benzo[1,4]dioxine-5-carboxylic acid methyl ester, enantiomer B.

Step C: A solution of 2-(5-bromomethyl-pyridin-3-yl)-2,3-dihydro-benzo[1,4]dioxine-5-carboxylic acid methyl ester, enantiomer B (1.3 g, 3.6 mmol) in 35 mL of DMF is treated with sodium thiomethoxide (325 mg, 4.6 mmol) and potassium carbonate (987 mg, 7.1 mmol) and stirred at room temperature overnight. After this time the reaction is filtered and the solids are washed with DCM. The combined filtrates are concentrated and the remaining residue is purified via silica gel flash column chromatography eluting with 0-8% MeOH in DCM to give 1 g of 2-(5-methylsulfanylmethyl-pyridin-3-yl)-2,3-dihydro-benzo[1,4]dioxine-5-carboxylic acid methyl ester, enantiomer B.

Step D: To a 0° C. stirred solution of 2-(5-methylsulfanylmethyl-pyridin-3-yl)-2,3-dihydro-benzo[1,4]dioxine-5-carboxylic acid methyl ester, enantiomer B (1.00 g, 3.0 mmol) in 45 mL of chloroform is added 3-chloroperoxybenzoic acid (593 mg, 2.4 mmol) in 4 additions over 20 minutes. The reaction is stirred for 15 minutes at 0° C. and treated with triethylamine (1.5 ml) and concentrated. The remaining residue is purified via flash chromatography on a Biotage KP-NH column eluting with 10-100% EtOAc/heptane to give 600 mg of 2-(5-methanesulfinylmethyl-pyridin-3-yl)-2,3-dihydro-benzo[1,4]dioxine-5-carboxylic acid methyl ester, mixture of diastereomers BA and BB.

Step E: To a solution of 2-(5-methanesulfinylmethyl-pyridin-3-yl)-2,3-dihydro-benzo[1,4]dioxine-5-carboxylic acid methyl ester, diastereomers BA and BB (600 mg, 1.7 mmol) in 30 mL of DCM is sequentially added 2,2,2-trifluoro-acetamide (390 mg, 3.5 mmol), magnesium oxide (278 mg, 6.9 mmol), rhodium(II) acetate dimer (53 mg, 0.1 mmol), and iodobenzene diacetate (835 mg, 2.6 mmol). The reaction is allowed to stir at room temperature for 17 hours. After this time, the reaction is re-charged with the reactants using the original equivalents. After stirring overnight at room temperature the reaction is filtered and the solids are washed with DCM. The combined filtrates are concentrated and the remaining crude residue is purified via silica gel flash column chromatography eluting with 5-100% EtOAc/heptane to give 160 mg of methyl 2-(5-{[methyl(oxo)[(trifluoroacetyl)imino]-λ$^6$-sulfanyl]methyl}pyridine-3-yl)-2,3-dihydro-1,4-benzodioxine-5-carboxylate, mixture of diastereomers BA and BB.

Step F: A 20 mL microwave reaction vessel is charged with methyl 2-(5-{[methyl(oxo)[(trifluoroacetyl)imino]-λ$^6$-sulfanyl]methyl}pyridine-3-yl)-2,3-dihydro-1,4-benzodioxine-5-carboxylate, diastereomers BA and BB (160 mg, 0.4 mmol) and 7N ammonia in methanol (8 mL). The vessel is capped and warmed at 85° C. for 2 days. After this time the reaction is cooled and concentrated. The crude is purified via HPLC (5-60% ACN/H2O, 20 minutes, TFA modified solvents) and the product-containing fractions are concentrated to give 2-(5-{[imino(methyl)oxo-λ$^6$-sulfanyl]methyl}pyridine-3-yl)-2,3-dihydro-1,4-benzodioxine-5-carboxamide, mixture of diastereomers BA and BB.

Step G: To a mixture of 2-(5-{[imino(methyl)oxo-λ$^6$-sulfanyl]methyl}pyridine-3-yl)-2,3-dihydro-1,4-benzodioxine-5-carboxamide, diasteromers BA and BB (220 mg, 0.5 mmol) in 25 mL of dioxane is added pyridine (0.77 mL, 9.5 mmol) and trifluoroacetic anhydride (0.67 mL, 4.8 mmol) drop-wise. The reaction is stirred at room temperature for 15 minutes after which time the reaction is concentrated to dryness. The remaining residue is treated with 7N MeOH in ammonia (50 mL) and the mixture is concentrated. The remaining residue is purified via HPLC (10-100% CH$_3$CN/H$_2$O over 20 minutes, 0.1% TFA) to give 70 mg of 2-(5-{[imino(methyl)oxo-λ$^6$-sulfanyl]methyl}pyridine-3-yl)-2,3-dihydro-1,4-benzodioxine-5-carbonitrile. Diastereomers BA and BB are resolved by chiral SFC to yield 62BA and 62BB.

Step H: (2-(5-Hydroxymethyl-pyridin-3-yl)-2,3-dihydro-benzo[1,4]dioxine-5-carboxylic acid methyl ester, enantiomer A is converted into 2-(5-{[imino(methyl)oxo-λ$^6$-sulfanyl]methyl}pyridine-3-yl)-2,3-dihydro-1,4-benzodioxine-5-carbonitrile, mixture of diasteromers AA and AB according to the above procedure, Example 16, Steps B through G. diasteromers AA and AB are resolved by chiral SFC to yield 62AA and 62BB.

TABLE 2

| | Chiral SFC Separation Conditions | | | | |
|---|---|---|---|---|---|
| Cpd # | Column | Mobile Phase | Flow Rate (mL/min) | Pressure (bar) | Temp (° C.) |
| 1 | ChiralPak IC | 32%(1:1:1 MeOH:EtOH:IPA + 0.1% DEA):CO$_2$ | 85 | 110 | 40 |
| 2 | RegisPack | 30% (2:1:1 MeOH:EtOH:IPA):CO$_2$ | 130 | 120 | 35 |
| 3 | RegisPack | 45%(EtOH):CO$_2$ | 125 | 120 | 35 |
| 4 | ChiralPak IC | 31%(1:1:1 MeOH:EtOH:IPA + 1% DEA):CO$_2$ | 84 | 130 | 40 |
| 5 | RegisPack | 25%(1:1:1MeOH:EtOH:IPA):CO$_2$ | 75 | 125 | 40 |
| 6A | LUX Cellulose-3 | 25%(1:1:1MeOH:EtOH:IPA):CO$_2$ | 155 | 120 | 35 |

TABLE 2-continued

Chiral SFC Separation Conditions

| Cpd # | Column | Mobile Phase | Flow Rate (mL/min) | Pressure (bar) | Temp (° C.) |
|---|---|---|---|---|---|
| 6B | LUX Cellulose-3 | 25%(1:1:1 MeOH:EtOH:IPA):$CO_2$ | 150 | 120 | 35 |
| 7 | LUX Cellulose-1 | 27%(1:1:1 MeOH:EtOH:IPA):$CO_2$ | 85 | 120 | 40 |
| 8 | ChiralPak IC | 40% (MeOH):$CO_2$ | 85 | 120 | 40 |
| 9 | LUX Cellulose-1 | 28%(1:1:1 MeOH:EtOH:IPA):$CO_2$ | 145 | 120 | 40 |
| 10 | ChiralPak AD-H | 32% (MeOH):$CO_2$ | 90 | 120 | 40 |
| 11 | RegisPack | 25% (1:1:1 MeOH:EtOH:IPA):$CO_2$ | 110 | 130 | 40 |
| 12 | LUX Cellulose-3 | 18%(1:1:1MeOH:EtOH:IPA + 0.1% DEA):$CO_2$ | 70 | 120 | 35 |
| 13 | LUX Cellulose-1 | 32%(1:1:1 MeOH:EtOH:IPA + 0.1% DEA):$CO_2$ | 85 | 120 | 35 |
| 14 | ChiralPak IA | 33%(1:1:1 MeOH:EtOH:IPA + 0.1% DEA):$CO_2$ | 110 | 120 | 35 |
| 15 | LUX Cellulose-1 | 30%((1:1:1MeOH:EtOH:IPA) + 0.1% DEA):$CO_2$ | 90 | 120 | 35 |
| 16 | LUX Cellulose-3 | 40%(1:1:1 MeOH:EtOH:IPA):$CO_2$ | 135 | 120 | 35 |
| 17 | LUX Cellulose-3 | 20%(1:1:1 MeOH:EtOH:IPA):$CO_2$ | 140 | 120 | 35 |
| 18 | LUX Cellulose-1 | 35% (1:1:1 MeOH:EtoH:IPA):$CO_2$ | 140 | 120 | 35 |
| 19 | LUX Cellulose-1 | 35% 3:1:1(MeOH:EtOH:IPA):$CO_2$ | 80 | 120 | 35 |
| 21 | LUX Cellulose-1 | 25% (1:1:1 MeOH:EtOH:IPA):$CO_2$ | 90 | 130 | 40 |
| 23 | LUX Cellulose-1 | 28% (6:7:7MeOH:EtOH:IPA):$CO_2$ | 80 | 120 | 40 |
| 24 | ChiralPak AD-H | 65% (1:1 MeOH:IPA + 0.2% isopropylamine):$CO_2$ | 65 | 100 | 25 |
| 25 | LUX Cellulose-1 | 30% (67% MeOH:33%(1:1EtOH:IPA) + 0.1% DEA):$CO_2$ | 65 | 120 | 35 |
| 26 | RegisPack | 25% (MeOH):$CO_2$ | 70 | 120 | 40 |
| 27 | LUX Cellulose-2 | 40% (MeOH):$CO_2$ | 80 | 120 | 35 |
| 28 | ChiralPak IC | 16%(1:1:1 MeOH:EtOH:IPA):$CO_2$ | 90 | 120 | 40 |
| 29 | RegisPack | 15%(11:5:4 MeOH:EtOH:IPA):$CO_2$ | 90 | 120 | 40 |
| 30 | RegisPack | 25%(2:1 IPA:MeOH)$CO_2$ | 85 | 120 | 40 |
| 32 | LUX Cellulose-1 | 30% (4:3:3 MeOH:EtOH:IPA):$CO_2$ | 80 | 120 | 40 |
| 33 | LUX Cellulose-3 | 15%(1:1:1MeOH:EtOH:IPA):$CO_2$ | 115 | 120 | 40 |
| 36 | LUX Cellulose-3 | 25%(1:1:1 MeOH:EtOH:IPA):$CO_2$ | 120 | 120 | 40 |
| 43 | LUX Cellulose-3 | 28%(1:1:1 MeOH:EtOH:IPA):$CO_2$ | 115 | 120 | 40 |
| 44 | LUX Cellulose-3 | 20%(85:15 MeOH:IPA):$CO_2$ | 85 | 130 | 40 |
| 45 | LUX Cellulose-1 | 30%(1:1:1MeOH:EtOH:IPA):$CO_2$ | 110 | 140 | 40 |
| 48 | LUX Cellulose-3 | 20% 1:1:1(MeOH:EtOH:IPA):$CO_2$ | 80 | 120 | 40 |
| 49A | ChiralPak IC | 25% 1:1:1(MeOH:EtOH:IPA):$CO_2$ | 120 | 120 | 35 |
| 49B | ChiralPak IC | 25% 1:1:1(MeOH:EtOH:IPA):$CO_2$ | 120 | 120 | 35 |
| 51 | LUX Cellulose-1 | 40%(1:1 MeOH:IPA):$CO_2$ | 120 | 120 | 40 |
| 52A | RegisPack | 25% (6:3:1 IPA:MeOH:EtOH):$CO_2$ | 80 | 120 | 40 |
| 52B | RegisPack | 25% (1:1:1 MeOH:EtOH:IPA):$CO_2$ | 80 | 120 | 40 |
| 54 | LUX Cellulose-3 | 20%(2:3:3 MeOH:EtOH:IPA):$CO_2$ | 65 | 130 | 40 |
| 55 | LUX Cellulose-3 | 25%(2:1:1 MeOH:EtOH:IPA):$CO_2$ | 85 | 120 | 40 |
| 56 | Chiracel OD-H | 30% (1:1:1 MeOH:EtOH:IPA):$CO_2$ | 115 | 120 | 35 |
| 57 | ChiralPak IA | 30% (1:1:1 MeOH:EtOH:IPA):$CO_2$ | 120 | 120 | 35 |
| 58 | LUX Cellulose-1 | 22% (1:1:1 MeOH:EtOH:IPA):$CO_2$ | 80 | 120 | 40 |
| 59 | ChiralPak AD-H | 45% (3:1 ACN:MeOH + 0.2% Isopropylamine):$CO_2$ | 80 | 100 | 25 |
| 60A | RegisPack | 35% 1:1:1 (MeOH:EtOH:IPA):$CO_2$ | 145 | 120 | 35 |
| 60B | RegisPack | 30% (1:1:1 MeOH:EtOH:IPA):$CO_2$ | 140 | 120 | 35 |
| 61 | ChiralPak AD-H | 26%(1:1:1 MeOH:EtOH:IPA):$CO_2$ | 90 | 120 | 40 |
| 62A | RegisPack | 45%(MeOH):$CO_2$ | 80 | 120 | 40 |
| 62B | LUX Cellulose-4 | 31% (65:35 MeOH:IPA):$CO_2$ | 70 | 140 | 40 |

TABLE 3

LC/MS Methods

| Method | Mobile Phase A | Mobile Phase B | Gradient | | | Flow (mL/min.) | Column |
|---|---|---|---|---|---|---|---|
| | | | Time (min) | % A | % B | | |
| A | 0.1% Formic Acid in Water | 0.1% Formic Acid in Acetonitrile | 0 | 90.0 | 10.0 | 0.5 | Thermo Scientific, Aquasil C18, 50 × 2.1 mm, 5μ |
| | | | 0.5 | 90.0 | 10.0 | | |
| | | | 1.5 | 1.0 | 99.0 | | |
| | | | 2.5 | 1.0 | 99.0 | | |
| | | | 3.3 | 90.0 | 10.0 | | |
| | | | 4.0 | 90.0 | 10.0 | | |

TABLE 3-continued

LC/MS Methods

| Method | Mobile Phase A | Mobile Phase B | Gradient | Flow (mL/min.) | Column |
|---|---|---|---|---|---|
| B | 95% Water 5% Acetonitrile + 0.05% Formic Acid | Acetonitrile + 0.05% Formic Acid | 90% A to 100% B in 1.19 minutes, hold at 100% B to 1.70 minutes | 0.8 | BEH 2.1 × 50 mm C18, 1.7 μm particle diameter |
| C | 95% Water 5% Acetonitrile + 2.5 mM Ammonium Bicarbonate | Acetonitrile | 90% A to 100% B in 1.19 minutes, hold at 100% B to 1.70 minutes | 0.8 | BEH 2.1 × 50 mm C18, 1.7 μm particle diameter |
| D | 95% Water 5% Acetonitrile + 2.5 mM Ammonium Bicarbonate | Acetonitrile | 90% A to 100% B in 4.45 minutes, hold at 100% B to 4.58 minutes | 0.8 | BEH 2.1 × 50 mm C18, 1.7 μm particle diameter |
| E | 95% Water 5% Acetonitrile + 0.05% Formic Acid | Acetonitrile + 0.05% Formic Acid | 95% A to 100% B in 3.65 minutes, hold at 100% B to 4.95 minutes | 0.6 | HSS T3 2.1 × 100 mm, 1.8 μm particle diameter |
| F | 95% Water 5% Acetonitrile + 0.05% Formic Acid | Acetonitrile + 0.05% Formic Acid | 100% A hold for 1.00 minute, 100% A to 95% B in 4.50 minutes, hold at 100% B to 4.91 minutes | 0.6 | HSS T3 2.1 × 100 mm, 1.8 μm particle diameter |

TABLE 4

LC/MS Data

| Cpd No | Mass Found | Retention Time (Min) | LCMS Method |
|---|---|---|---|
| 1A | 357.2 | 0.37 | B |
| 1B | 357.2 | 0.37 | B |
| 2A | 322.4 | 0.61 | B |
| 2B | 321.9 | 0.62 | B |
| 3A | 404.0 | 0.57 | C |
| 3B | 404.0 | 0.56 | C |
| 4A | 257.1 | 1.66 | A |
| 4B | 257.2 | 1.66 | A |
| 5A | 354.2 | 1.23 | A |
| 5B | 354.2 | 1.23 | A |
| 6AA | 354.2 | 0.44 | B |
| 6AB | 353.9 | 0.44 | B |
| 6BA | 354.0 | 0.44 | B |
| 6BB | 354.0 | 0.44 | B |
| 7A | 398.0 | 0.53 | B |
| 7B | 397.9 | 0.53 | B |
| 8A | 349.2 | 1.16 | A |
| 8B | 349.2 | 1.16 | A |
| 9A | 325.0 | 0.76 | B |
| 9B | 325.0 | 0.76 | B |
| 10A | 341.4 | 0.48 | B |
| 10B | 340.9 | 0.47 | B |
| 11A | 355.1 | 0.56 | B |
| 11B | 355.1 | 0.56 | B |
| 12A | 398.2 | 0.53 | B |
| 12B | 397.8 | 0.51 | B |
| 13A | 384.3 | 1.14 | A |
| 13B | 384.3 | 1.14 | A |
| 14A | 354.0 | 0.5 | B |
| 14B | 354.0 | 0.5 | B |
| 15A | 369.6 | 0.42 | B |
| 15B | 369.7 | 0.42 | B |
| 16A | 412.1 | 1.19 | A |
| 16B | 412.1 | 1.19 | A |
| 17A | 383.8 | 0.51 | C |
| 17B | 384.0 | 0.52 | C |
| 18A | 384.0 | 0.52 | C |
| 18B | 384.0 | 0.52 | C |
| 19A | 370.2 | 0.5 | C |
| 19B | 369.9 | 0.5 | C |
| 20A | 286.9 | 0.43 | C |
| 20B | 286.9 | 0.43 | C |
| 21A | 289.3 | 0.66 | B |
| 21B | 289.0 | 0.66 | B |
| 22A | 307.3 | 0.65 | B |
| 22B | 307.3 | 0.63 | C |
| 23A | 270.9 | 1.15 | A |
| 23B | 271.1 | 1.16 | A |
| 24A | 368.0 | 0.57 | C |
| 24B | 368.0 | 0.57 | C |
| 25A | 372.2 | 0.49 | C |
| 25B | 372.2 | 0.49 | C |
| 26A | 327.2 | 0.48 | B |
| 26B | 327.2 | 0.47 | B |
| 27A | 315.7 | 2.04 | F |
| 27B | 315.5 | 2.12 | F |
| 28A | 339.2 | 1.32 | A |
| 28B | 339.2 | 1.32 | A |
| 29A | 342.0 | 0.48 | C |
| 29B | 342.0 | 0.48 | C |
| 30A | 418.0 | 0.61 | C |
| 30B | 417.9 | 0.61 | C |
| 31A | 355.9 | 0.56 | D |
| 31B | 355.9 | 0.59 | D |
| 32A | 359.3 | 1.26 | A |
| 32B | 359.3 | 1.26 | A |
| 33A | 412.0 | 0.58 | C |
| 33B | 412.0 | 0.57 | C |
| 34A | 338.0 | 0.64 | C |
| 34B | 338.0 | 0.61 | C |
| 35A | 336.1 | 0.63 | B |
| 35B | 336.0 | 0.66 | B |
| 36A | 352.2 | 1.23 | A |
| 36B | 352.2 | 1.22 | A |
| 37A | 331.0 | 0.64 | B |
| 37B | 331.2 | 0.64 | B |
| 38A | 380.3 | 1.31 | A |
| 38B | 380.3 | 1.31 | A |
| 39A | 336.0 | 0.68 | C |
| 39B | 336.0 | 0.68 | C |
| 40A | 394.9 | 0.81 | B |
| 40B | 394.9 | 0.85 | B |

TABLE 4-continued

| | LC/MS Data | | |
|---|---|---|---|
| Cpd No | Mass Found | Retention Time (Min) | LCMS Method |
| 41A | 386.2 | 0.74 | B |
| 41B | 386.3 | 0.74 | B |
| 42A | 354.0 | 1.21 | D |
| 42B | 354.0 | 1.19 | D |
| 43A | 366.2 | 1.24 | A |
| 43B | 366.2 | 1.24 | A |
| 44A | 346.8 | 0.69 | B |
| 44B | 346.9 | 0.69 | B |
| 45A | 300.8 | 0.6 | B |
| 45B | 300.9 | 0.6 | B |
| 46A | 343.2 | 0.54 | B |
| 46B | 342.9 | 0.54 | B |
| 47A | 356.9 | 0.58 | B |
| 47B | 356.8 | 0.58 | B |
| 48A | 426.3 | 0.66 | B |
| 48B | 426.0 | 0.66 | B |
| 49AA | 354.9 | 0.59 | B |
| 49AB | 354.9 | 0.59 | B |
| 49BA | 354.9 | 0.6 | B |
| 49BA | 354.9 | 0.6 | B |
| 50B | 339.2 | 0.59 | B |
| 51A | 275.2 | 0.62 | C |
| 51B | 275.2 | 0.62 | C |
| 52AA | 313.1 | 0.48 | C |
| 52AB | 313.1 | 0.46 | C |
| 52BA | 313.1 | 0.46 | C |
| 52BB | 313.1 | 0.47 | C |
| 53 | 363.8 | 0.78 | B |
| 54A | 359.9 | 0.65 | B |
| 54B | 359.9 | 0.65 | B |
| 55A | 366.3 | 1.29 | A |
| 55B | 366.3 | 1.28 | A |
| 56A | 319.2 | 1.2 | A |
| 56B | 319.2 | 1.2 | A |
| 57A | 319.2 | 1.2 | A |
| 57B | 319.2 | 1.2 | A |
| 58A | 332.9 | 0.7 | C |
| 58B | 332.9 | 0.7 | C |
| 59A | 270.9 | 0.62 | C |
| 59B | 271.3 | 0.41 | B |
| 60AA | 418.0 | 1.64 | E |
| 60AB | 418.0 | 1.62 | E |
| 60BA | 418.0 | 1.65 | E |
| 60BB | 418.0 | 1.63 | E |
| 61A | 296.0 | 0.6 | C |
| 61B | 296.0 | 0.6 | C |
| 62AA | 330.1 | 2.66 | F |
| 62AB | 330.1 | 2.66 | F |
| 62BA | 330.1 | 0.55 | B |
| 62BB | 330.1 | 0.55 | B |

ASSESSMENT OF BIOLOGICAL ACTIVITY

Preparation of Cynomolgus Adrenal Mitochondria

The aldosterone synthase and cortisol synthase inhibition assays employ cynomolgus adrenal gland mitochondria as the source of aldosterone synthase (CYP11B2) and cortisol synthase (CYP11B1). Mitochondria are prepared from frozen cynomolgus monkey adrenal glands according to Method A described in by J. D. McGarry et al. (Biochem. J., 1983, 214, 21-28), with a final resuspension in the AT buffer described in R. Yamaguchi et al. (Cell Death and Differentiation, 2007, 14, 616-624), frozen as aliquots in liquid nitrogen and stored at −80° C. until use. Activity of CYP11B2 and CYP11B1 in these preparations is defined as the amount of enzyme that generates 1 pmol of product in one hour under the conditions described.

Inhibition of Aldosterone Synthase

The compounds of the invention may be evaluated for aldosterone synthase inhibition by the following assay:

Assays are performed in 96-well format in a final volume of 60 μL/well, containing 100 mM potassium phosphate, pH 7.4, 1% (v/v) DMSO, and additionally, 2 μM of corticosterone and 50 units of CYP11B2 activity. Reactions are started by the addition of NADPH to 1 mM and allowed to proceed for 90 minutes at 37° C. Reactions are terminated by the addition of 60 μL of MeCN containing an internal standard for mass spectrometry. One hundred microliters are then transferred to a glass filter plate and centrifuged at 570×g for 5 minutes and the filtrate is collected. Reaction product aldosterone is quantified by mass spectrometry. To determine the assay blank value (0% activity), NADPH is omitted from some reactions.

Dose dependent inhibition is quantified by the inclusion of compound at various concentrations. Maximum activity (100%) is defined by reactions containing NADPH, but without compound. Activities at each concentration are expressed as a percentage of the maximum activity (y-axis) and plotted against concentration of compound (x-axis) and the concentration corresponding to 50% activity ($IC_{50}$) determined using the XLFit curve-fitting program using a 4-parameter logistic model.

Inhibition of Cortisol Synthesis

Assays are performed as for aldosterone synthase except for the use of 150 units of CYP11B1, 11-deoxycortisol as substrate and cortisol measured as product.

Representative compounds of the present invention were tested for activity in the above assays. Preferred compounds have an $IC_{50}$<1,000 nM and more preferred compounds have an $IC_{50}$<100 nM in this assay. As examples, data for representative compounds from Table 1 are shown in Table 5. Data for individual enantiomers are indicated by separate entries for enantiomers A and B.

TABLE 5

| | Biological Data | |
|---|---|---|
| Cpd No | Cyp11B2 Inhibition $IC_{50}$ (nM) | Cyp11B1 Inhibition $IC_{50}$ (nM) |
| 1A | 570 | >100000 |
| 1B | 33 | 24000 |
| 2A | 120 | 60 |
| 2B | 17 | 230 |
| 3A | 140 | >30000 |
| 3B | 33 | 5600 |
| 4A | 68 | 3100 |
| 4B | 22 | 2500 |
| 5A | 310 | >30000 |
| 5B | 39 | 22000 |
| 6AA | 26 | 2200 |
| 6AB | 70 | 10000 |
| 6BA | 190 | >30000 |
| 6BB | 1000 | >30000 |
| 7A | >30,000 | >30000 |
| 7B | 47 | 19000 |
| 8A | >30,000 | >30000 |
| 8B | 28 | 13000 |
| 9A | 110 | 5200 |
| 9B | 10 | 2200 |
| 10A | 66 | 3400 |
| 10B | 14 | 230 |
| 11A | 180 | 24000 |
| 11B | 19 | 4400 |
| 12A | 100 | 18000 |
| 12B | 10 | 2000 |
| 13A | >1000 | >100000 |
| 13B | 95 | 66000 |
| 14A | 29 | 12000 |
| 14B | 660 | >30000 |
| 15A | 48 | 15000 |

TABLE 5-continued

Biological Data

| Cpd No | Cyp11B2 Inhibition IC$_{50}$ (nM) | Cyp11B1 Inhibition IC$_{50}$ (nM) |
|---|---|---|
| 15B | 540 | >30000 |
| 16A | 24 | 5200 |
| 16B | 17 | 54 |
| 17A | 840 | >30000 |
| 17B | 67 | 18000 |
| 18A | 610 | 16000 |
| 18B | 41 | 1100 |
| 19A | 1400 | >30000 |
| 19B | 70 | 24000 |
| 20A | 110 | 8200 |
| 20B | 17 | 6800 |
| 21A | 5 | 2600 |
| 21B | 11 | 5300 |
| 22A | 62 | 2000 |
| 22B | 11 | 2300 |
| 23A | 7.5 | 1400 |
| 23B | 13 | 2000 |
| 24A | 18 | 7000 |
| 24B | 61 | 25000 |
| 25A | 830 | >100000 |
| 25B | 60 | 15000 |
| 26A | 48 | 1800 |
| 26B | 14 | 670 |
| 27A | 17 | 2800 |
| 27B | 31 | 5000 |
| 28A | 2200 | >30000 |
| 28B | 180 | 6100 |
| 29A | 44 | 22000 |
| 29B | 520 | >30000 |
| 30A | 75 | 22000 |
| 30B | 550 | 24000 |
| 31A | 52 | >30000 |
| 31B | 250 | >30000 |
| 32A | 73 | 6000 |
| 32B | 20 | 350 |
| 33A | 7400 | >30000 |
| 33B | 280 | >30000 |
| 34A | 9 | 8500 |
| 34B | 100 | >30000 |
| 35A | 8 | 530 |
| 35B | 33 | 6200 |
| 36A | 100 | >30000 |
| 36B | 14 | 5800 |
| 37A | 61 | 25000 |
| 37B | 12 | 8000 |
| 38A | 66 | 15000 |
| 38B | 6 | 700 |
| 39A | 11 | 7300 |
| 39B | 220 | >30000 |
| 40A | 300 | >30000 |
| 40B | 70 | 11000 |
| 41A | 110 | 24000 |
| 41B | 8 | 3900 |
| 42A | 110 | 18000 |
| 42B | 10 | 1300 |
| 43A | 25 | 22000 |
| 43B | 460 | >30000 |
| 44A | 9 | 2200 |
| 44B | 81 | 13000 |
| 45A | 18 | 210 |
| 45B | 5 | 280 |
| 46A | 260 | 7000 |
| 46B | 17 | 4200 |
| 47A | 110 | 8500 |
| 47B | 10 | 1200 |
| 48A | 51 | 3100 |
| 48B | 20 | 240 |
| 49AA | 90 | 3200 |
| 49AB | 17 | 1100 |
| 49BA | 66 | 2500 |
| 49BA | 15 | 1100 |
| 50B | 8 | 3300 |
| 51A | 140 | 1200 |
| 51B | 38 | 20000 |
| 52AA | 37 | 4100 |
| 52AB | 37 | 820 |
| 52BA | 71 | 16000 |
| 52BB | 42 | 13000 |
| 53 | 35 | 24000 |
| 54A | — | 23000 |
| 54B | — | 14000 |
| 55A | 26 | 11000 |
| 55B | 240 | >30000 |
| 56A | 78 | 14000 |
| 56B | 24 | 14000 |
| 57A | 50 | 16000 |
| 57B | 59 | 15000 |
| 58A | 190 | 23000 |
| 58B | 180 | 3000 |
| 59A | 24 | 1100 |
| 59B | 4 | 890 |
| 60AA | 530 | >30000 |
| 60AB | 60 | >30000 |
| 60BA | 3200 | >30000 |
| 60BB | 81 | >30000 |
| 61A | 52 | 25000 |
| 61B | 44 | 22000 |
| 62AA | 320 | >30000 |
| 62AB | 500 | >30000 |
| 62BA | 25 | 14000 |
| 62BB | 53 | 18000 |

Methods of Therapeutic Use

In accordance with the invention, there are provided novel methods of using the compounds of formula (I). The compounds disclosed herein effectively inhibit aldosterone synthase. The inhibition of aldosterone synthase is an attractive means for preventing and treating a variety of diseases or conditions that can be alleviated by lowering levels of aldosterone. Thus, the compounds are useful for the treatment of diseases and conditions as described in the Background section, including the following conditions and diseases:

Diabetic kidney disease including diabetic nephropathy;

Non-diabetic kidney disease including glomerulosclerosis, glomerulonephritis, IGA nephropathy, nephritic syndrome and focal segmental glomerulosclerosis (FSGS);

Cardiovascular diseases including hypertension, pulmonary arterial hypertension, Conn's syndrome, systolic heart failure, diastolic heart failure, left ventricular dysfunction, left ventricular stiffness and fibrosis, left ventricular filing abnormalities, arterial stiffness, atherosclerosis and cardiovascular morbidity associated with primary or secondary hyperaldosteronism;

Adrenal hyperplasia and primary and secondary hyperaldosteronism.

These disorders have been well characterized in man, but also exist with a similar etiology in other mammals, and can be treated by pharmaceutical compositions of the present invention.

Accordingly, a compound of formula I according to any of the embodiments described herein or a pharmaceutically acceptable salt thereof may be used for the preparation of a medicament for treating a disease or disorder mediated by aldosterone synthase, including diabetic nephropathy, glomerulosclerosis, glomerulonephritis, IGA nephropathy, nephritic syndrome focal segmental glomerulosclerosis (FSGS), hypertension, pulmonary arterial hypertension, Conn's syndrome, systolic heart failure, diastolic heart failure, left ventricular dysfunction, left ventricular stiffness and fibrosis, left ventricular filing abnormalities, arterial stiffness, atherosclerosis and cardiovascular morbidity associated with primary or secondary hyperaldosteronism, adrenal hyperplasia and primary and secondary hyperaldosteronism.

For therapeutic use, the compounds of the invention may be administered via a pharmaceutical composition in any conventional pharmaceutical dosage form in any conventional manner. Conventional dosage forms typically include a pharmaceutically acceptable carrier suitable to the particular dosage form selected. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. In one embodiment, for example, multiple compounds of the present invention can be administered. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds of the present invention and the conventional therapeutics or other adjuvants may be administered separately (either serially or in parallel). Separate dosing allows for greater flexibility in the dosing regime.

As mentioned above, dosage forms of the compounds of this invention may include pharmaceutically acceptable carriers and adjuvants known to those of ordinary skill in the art and suitable to the dosage form. These carriers and adjuvants include, for example, ion exchangers, alumina, aluminum stearate, lecithin, serum proteins, buffer substances, water, salts or electrolytes and cellulose-based substances. Preferred dosage forms include tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements for the compounds of the present invention may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

What is claimed is:
1. A compound of the formula I

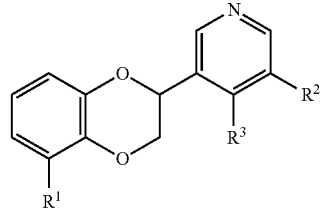

wherein:
$R^1$ is selected from —C(O)NH$_2$, —C(O)NH(CH$_3$) and —CN;
$R^2$ is —(X)—R$^4$, wherein
—(X)— is a bond, —CH$_2$—, or —O—; and
$R^4$ is selected from
—H;
C$_{1-3}$alkyl, optionally substituted with one to four groups selected from —F, —SO$_2$C$_{1-3}$alkyl, and —OH;
halogen;
—CN;
—SO$_2$C$_{1-3}$alkyl;
—C(O)N(C$_{1-3}$alkyl)$_2$, provided —(X)— is not —O—;
—NHC(O)R$^5$ or —N(CH$_3$)C(O)R$^5$, provided that —(X)— is —CH$_2$— and wherein R$^5$ is selected from C$_{3-6}$cycloalkyl and C$_{1-3}$alkyl optionally substituted with one to three —F groups;
—NHSO$_2$C$_{1-3}$alkyl;
—CH(cyclopropyl)NHSO$_2$C$_{1-3}$alkyl;
—OCH$_2$C(O)N(C$_{1-3}$alkyl)$_2$, provided that —(X)— is —CH$_2$—;
—S(=O)(=NH)CH$_3$, provided that —(X)— is —CH$_2$—;
heterocyclyl selected from tetrahydropyranyl, tetrahydrofuranyl, pyrrolidinyl, 1,1-dioxo[1,2]-thiazine, morpholinyl, oxazolidinyl, piperidinyl, azetidinyl, wherein said heterocyclyl is optionally substituted with one to three groups selected from —C(O)C$_{1-3}$alkyl, halogen, —OH, oxo and C$_{1-3}$alkyl;
—C(O)-heterocyclyl, provided that —(X)— is —CH$_2$, wherein said heterocyclyl is selected from morpholin-4-yl, pyrrolidin-1-yl and piperidin-1-yl, optionally substituted with one or two groups selected from —F and —OH;
C$_{3-6}$cycloalkyl optionally substituted with —CN or —OH; and
phenyl, optionally substituted with —SO$_2$NH$_2$; and
$R^3$ is H, or C$_{1-3}$alkyl optionally substituted with —OH; or
$R_2$ and $R^3$ together form an annelated five-membered cycloalkyl ring optionally substituted with —OH;
or a salt or a stereoisomer thereof.
2. The compound according to claim 1, wherein:
$R^1$ is —C(O)NH$_2$ or —CN;
$R^2$ is —(X)—R$^4$, wherein
—(X)— is a bond, and
$R^4$ is selected from
—CH$_3$,
—CF$_3$;

—CHF$_2$;
—CH$_2$OH;
—CH(OH)CH$_3$;
—CH(OH)CF$_3$;
—F;
—CN;
heterocyclyl selected from tetrahydropyranyl and pyrrolidinyl, wherein said heterocyclyl is optionally substituted with one to three groups selected from C$_{1-3}$alkyl, halogen, —OH and oxo;
C$_{3-6}$cycloalkyl optionally substituted with —CN or —OH; and
phenyl, optionally substituted with —SO$_2$NH$_2$; or
—(X)— is O, and
R$^4$ is selected from
C$_{1-3}$alkyl;
—CH$_2$SO$_2$C$_{1-3}$alkyl; and
heterocyclyl selected from tetrahydropyranyl, tetrahydrofuranyl, pyrrolidinyl, piperidinyl, and azetidinyl, wherein said heterocyclyl is optionally substituted with one to three groups selected from —C(O)C$_{1-3}$alkyl, halogen, —OH, oxo and C$_{1-3}$alkyl; or
X is (—CH$_2$—), and
R$^4$ is selected from
—SO$_2$C$_{1-3}$alkyl;
—C(O)N(C$_{1-3}$alkyl)$_2$;
—NHC(O)R$^5$ or —N(CH$_3$)C(O)R$^5$, wherein R$^5$ is selected from cyclopropyl and C$_{1-3}$alkyl optionally substituted with one to three —F groups;
—OCH$_2$C(O)N(C$_{1-3}$ alkyl)$_2$;
—NHSO$_2$C$_{1-3}$alkyl;
—S(═O)(═NH)CH$_3$;
heterocyclyl selected from pyrrolidinyl, 1,1-dioxo[1,21-thiazine, morpholinyl and oxazolidinyl, wherein said heterocyclyl is optionally substituted with one to three groups selected from —C(O)C$_{1-3}$alkyl, halogen, —OH, oxo and C$_{1-3}$alkyl; and
—C(O)-heterocyclyl, wherein the heterocyclyl is selected from morpholin-4-yl, pyrrolidin-1-yl and piperidin-1-yl, optionally substituted with one or two groups selected from —F and —OH; and
R$^3$ is H or C$_{1-3}$alkyl optionally substituted with —OH;
or a salt or a stereoisomer thereof.

3. The compound according to claim 1, wherein:
R$^2$ is —(X)—R$^4$, wherein
—(X)— is a bond, and
R$^4$ is selected from
—CF$_3$;
—CHF$_2$;
—CH$_2$OH;
—CH(OH)CH$_3$;
—CH(OH)CF$_3$;
—F;
—CN;
heterocyclyl selected from tetrahydropyranyl and pyrrolidinyl, wherein said heterocyclyl is substituted with one to three groups selected from C$_{1-3}$alkyl, —F, —OH and oxo;
C$_{3-6}$cycloalkyl, substituted with —CN or —OH; and
phenyl, optionally substituted with —SO$_2$NH$_2$; and
R$^3$ is H, or C$_{1-3}$alkyl optionally substituted with —OH;
or a salt or a stereoisomer thereof.

4. The compound according to claim 1, wherein:
R$^2$ is —(X)—R$^4$, wherein
—(X)— is O, and
R$^4$ is selected from
C$_{1-3}$alkyl;
—CH$_2$SO$_2$C$_{1-3}$alkyl; and
heterocyclyl selected from tetrahydropyranyl, tetrahydrofuranyl, pyrrolidinyl, piperidinyl, and azetidinyl, wherein said heterocyclyl is optionally substituted with —C(O)C$_{1-3}$alkyl; and
R$^3$ is H, or C$_{1-3}$alkyl optionally substituted with —OH;
or a salt or a stereoisomer thereof.

5. The compound according to claim 1, wherein:
R$^2$ is —(X)—R$^4$, wherein
X is (—CH$_2$—), and
R$^4$ is selected from
—SO$_2$C$_{1-3}$alkyl;
—C(O)N(C$_{1-3}$alkyl)$_2$;
—NHC(O)R$^5$ or —N(CH$_3$)C(O)R$^5$, wherein R$^5$ is selected from cyclopropyl and C$_{1-3}$alkyl optionally substituted with one to three —F groups;
—OCH$_2$C(O)N(C$_{1-3}$ alkyl)$_2$;
—NHSO$_2$C$_{1-3}$alkyl;
—S(═O)(═NH)CH$_3$;
heterocyclyl selected from pyrrolidinyl, 1,1-dioxo[1,2]-thiazine, morpholinyl and oxazolidinyl, wherein said heterocyclyl is optionally substituted with one to two groups selected from oxo and C$_{1-3}$alkyl; and
—C(O)-heterocyclyl, wherein the heterocyclyl is selected from morpholin-4-yl, pyrrolidin-1-yl and piperidin-1-yl, optionally substituted with one or two groups selected from —F and —OH; and
R$^3$ is H, or C$_{1-3}$alkyl optionally substituted with —OH;
or a salt or a stereoisomer thereof.

6. The compound according to claim 1, wherein:
R$^1$ is —C(O)NH$_2$;
or a salt or a stereoisomer thereof.

7. The compound according to claim 1, wherein:
R$^1$ is —CN;
or a salt or a stereoisomer thereof.

8. The compound according to claim 1 selected from the group consisting of

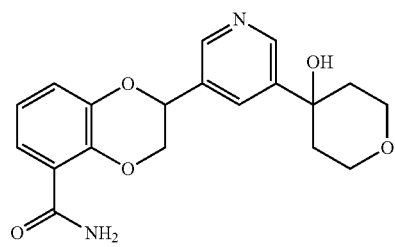

1

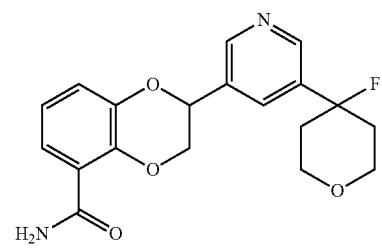

32

| | |
|---|---|
| 2 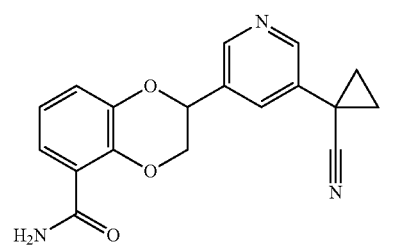 | 5 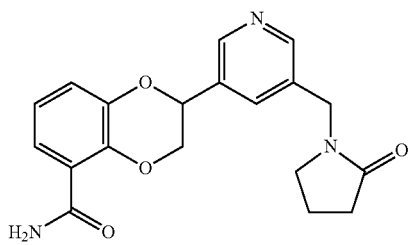 |
| 33 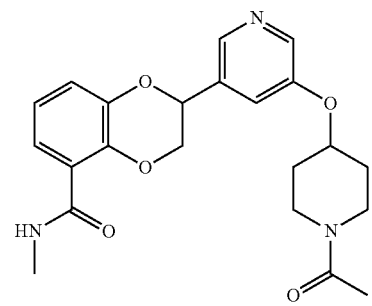 | 36 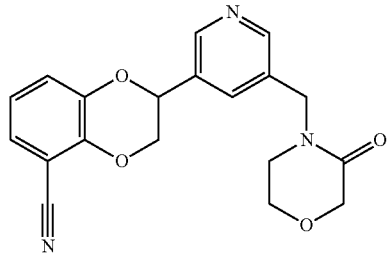 |
| 3 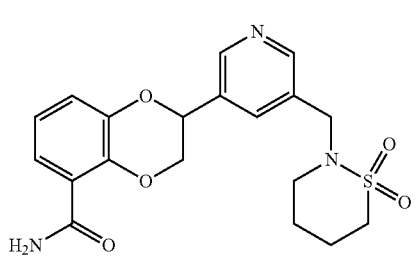 | 6 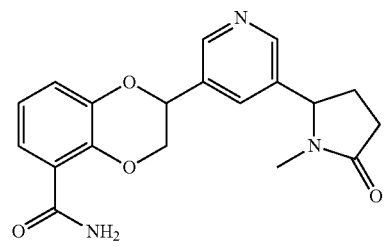 |
| 34 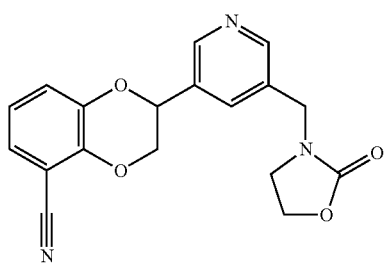 | 37 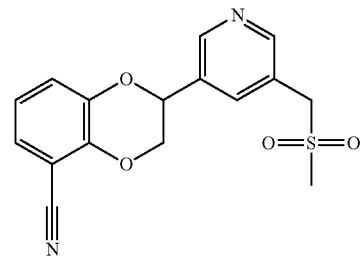 |
| 4 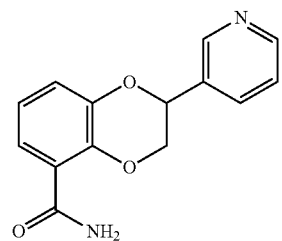 | 7 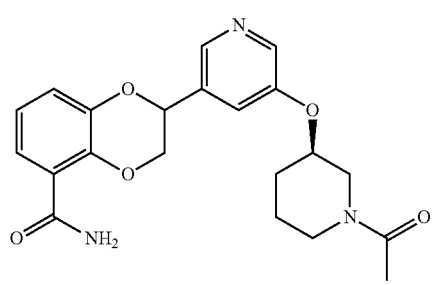 |
| 35 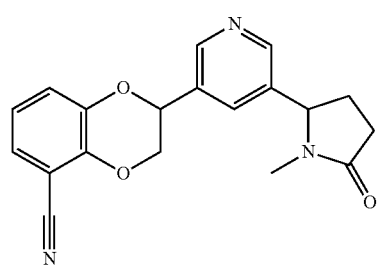 | 38 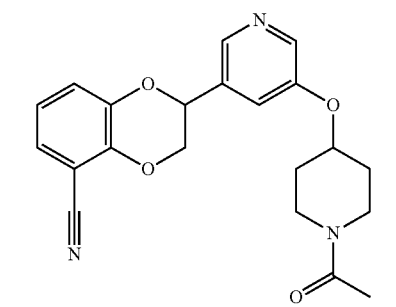 |

8
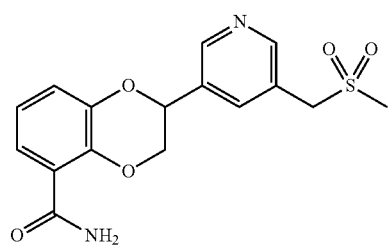
39
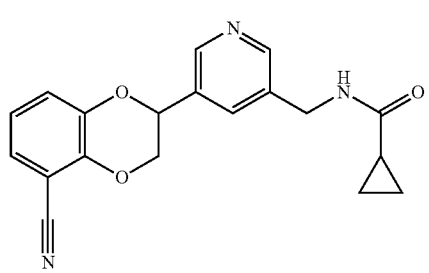
9
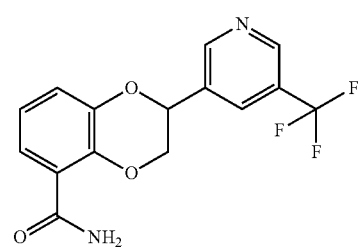
40
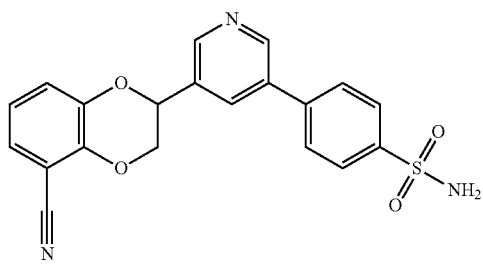
10
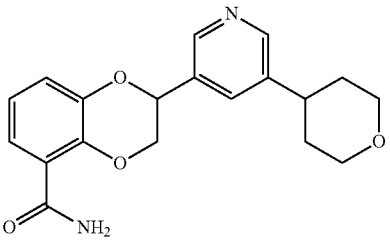
41
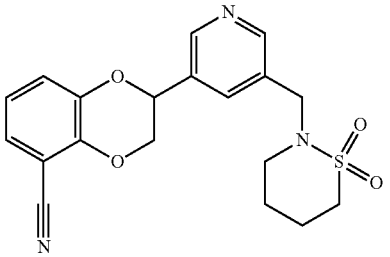
11
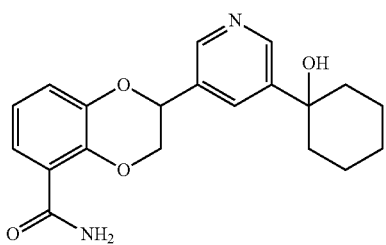
42
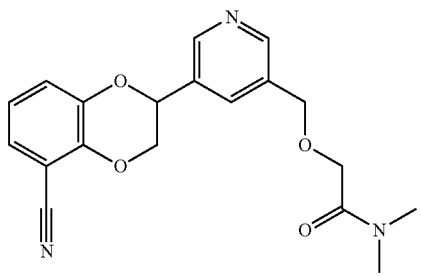
12
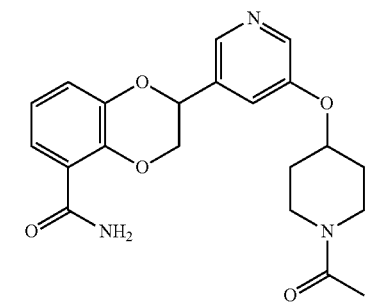
43
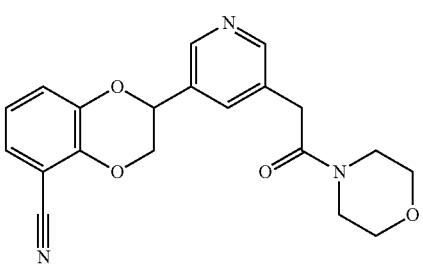
13
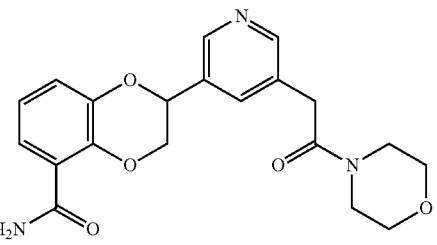
44
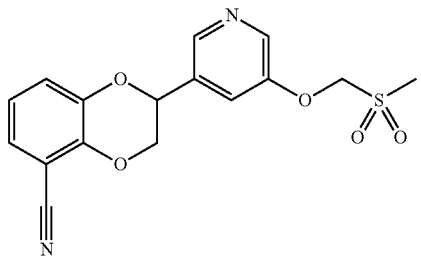

14
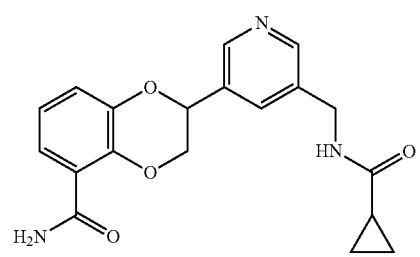
15
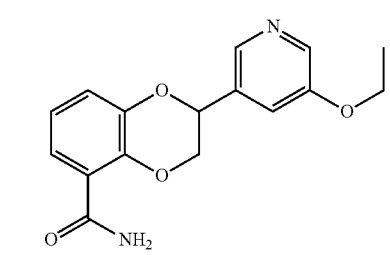
15
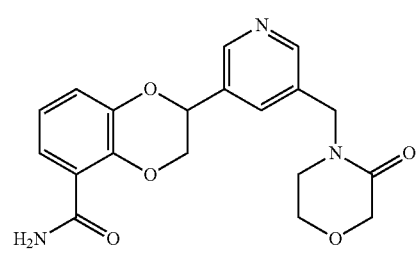
16
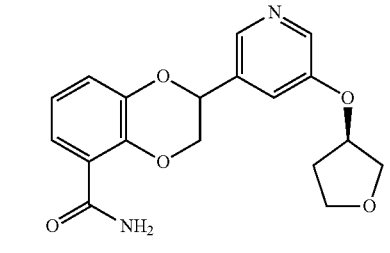
16
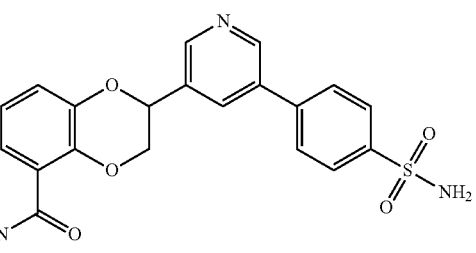
47
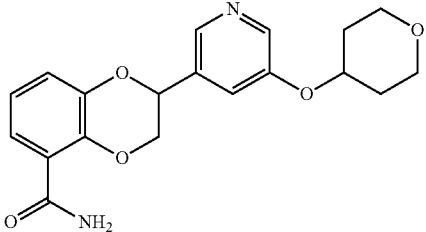
17
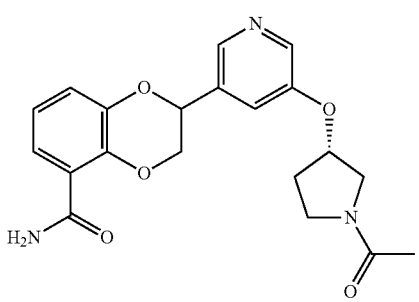
48
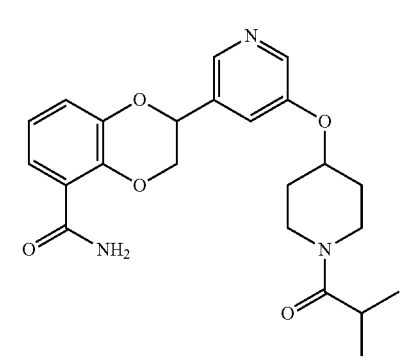
18
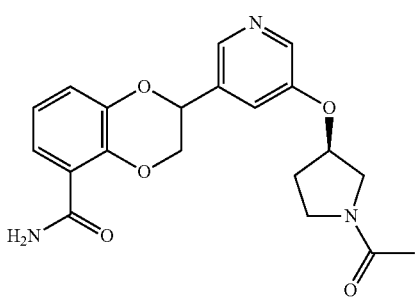
49
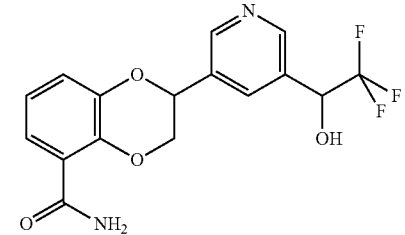
19
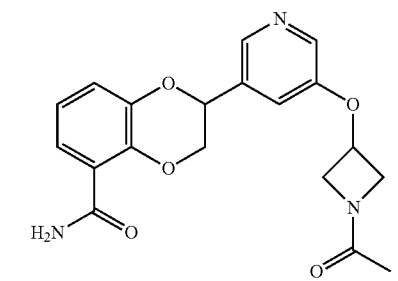

50
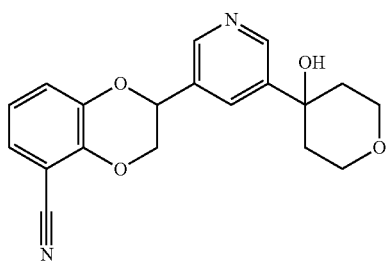
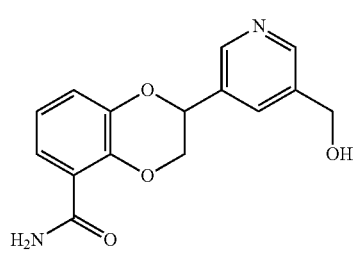
51
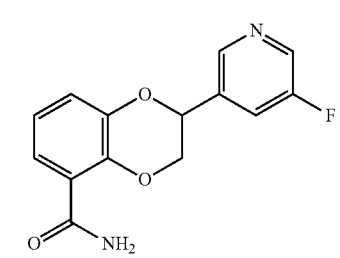
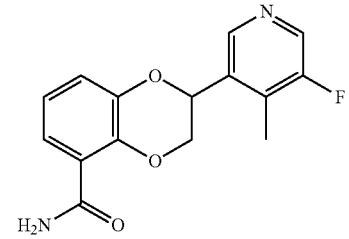
52
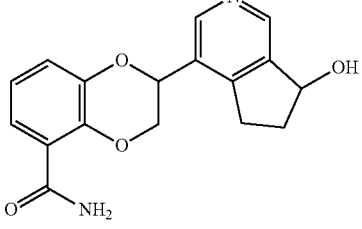
22
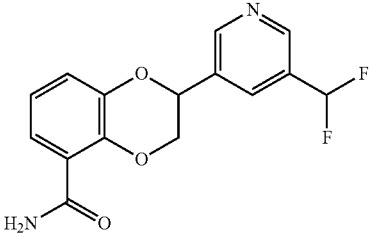
53
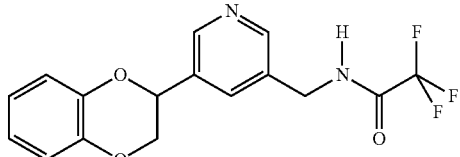
23
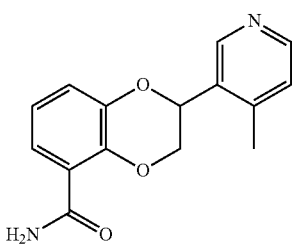
54
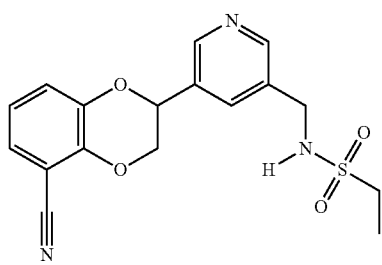
24
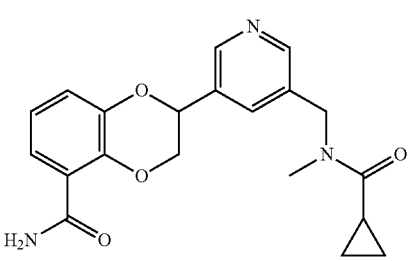
55
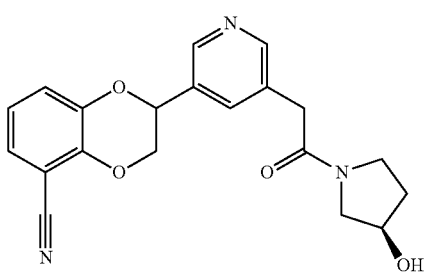
25
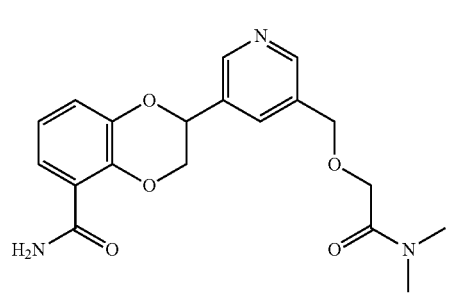

| | |
|---|---|
| 56 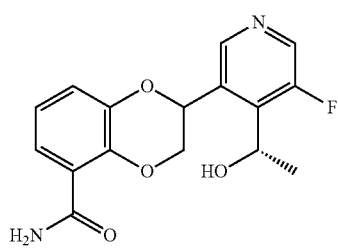 | 59 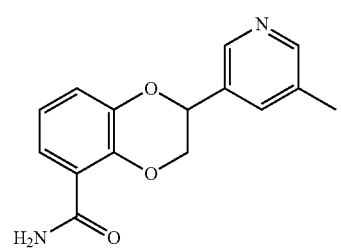 |
| 26 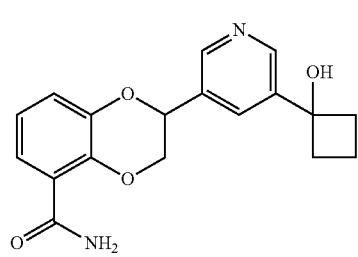 | 29 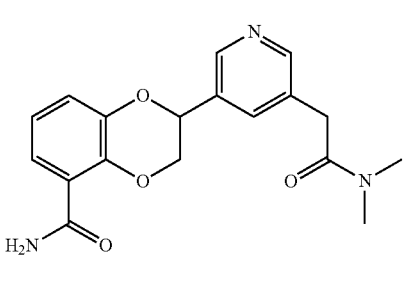 |
| 57 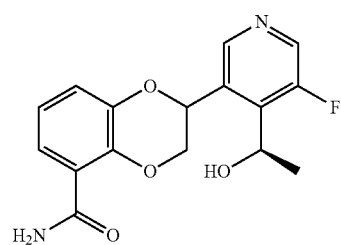 | 60 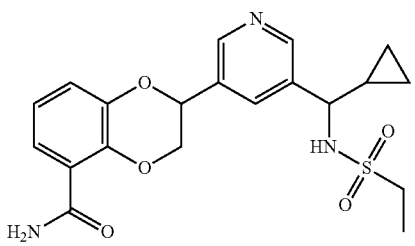 |
| 27 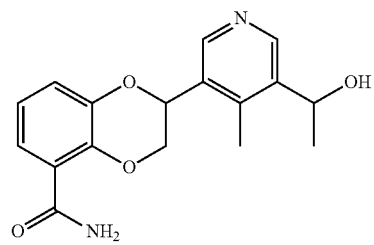 | 30 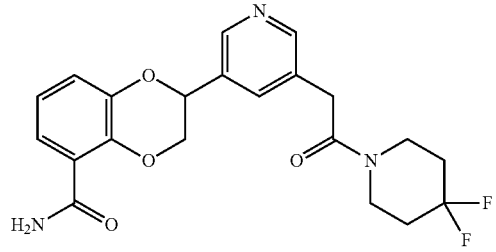 |
| 58 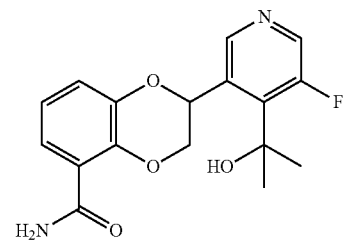 | 61 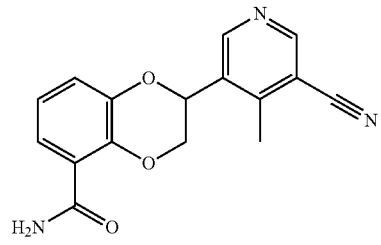 |
| 28 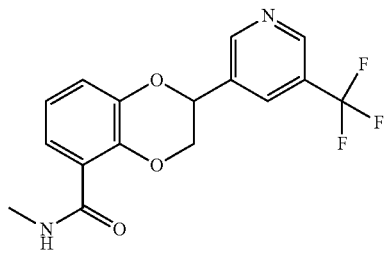 | 31 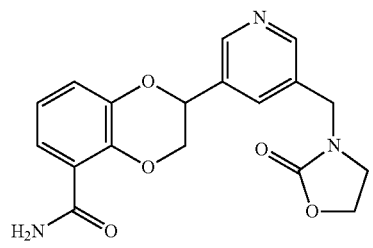 |

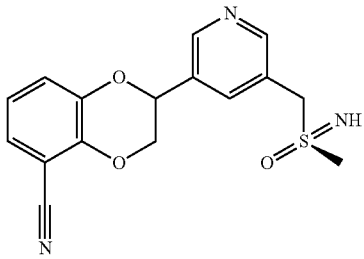

or a pharmaceutically acceptable salt or a stereoisomer thereof.

9. The compound according to claim 8 selected from the group consisting of compound numbers 1, 5, 12, 29, 37, 43, 56, 61, and 62 or a pharmaceutically acceptable salt or a stereoisomer thereof.

10. A pharmaceutical composition comprising a compound according to claim 1 and a pharmaceutically acceptable excipient or carrier.

11. A method of treating a disease or disorder that can be alleviated by inhibition of aldosterone synthase selected from diabetic nephropathy, glomerulosclerosis, glomerulonephritis, IGA nephropathy, nephritic syndrome, focal segmental glomerulosclerosis (FSGS), hypertension, systolic heart failure, diastolic heart failure, left ventricular dysfunction, arterial stiffness, and adrenal hyperplasia and primary and secondary hyperaldosteronism, the method comprising administering a therapeutically effective amount of a compound according to claim 1 to patient in need thereof.

12. The method according to claim 11, wherein the disease or disorder is selected from diabetic nephropathy, glomerulosclerosis, glomerulonephritis, IGA nephropathy, nephritic syndrome and focal segmental glomerulosclerosis (FSGS).

13. The method according to claim 11 wherein the disease is diabetic nephropathy.

14. A method of treating a disease or disorder that can be alleviated by inhibition of aldosterone synthase selected from pulmonary arterial hypertension, Conn's syndrome, left ventricular stiffness and fibrosis, left ventricular filling abnormalities, and atherosclerosis, the method comprising administering a therapeutically effective amount of a compound according to claim 1 to patient in need thereof.

15. The compound according to claim 1, wherein the compound is

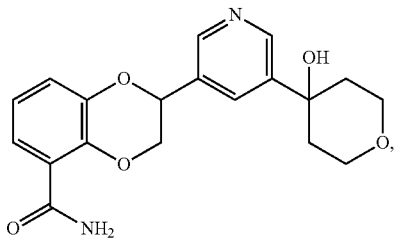 [SMILES: NC(=O)c1cccc2c1OCC(c1cncc(C3(O)CCOCC3)c1)O2]

or a pharmaceutically acceptable salt thereof.

16. The compound according to claim 1, wherein the compound is

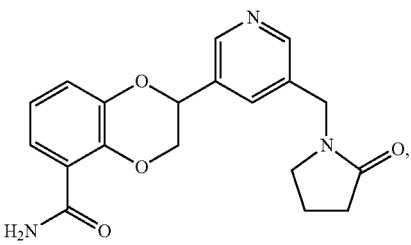 [SMILES: NC(=O)c1cccc2c1OCC(c1cncc(CN3CCCC3=O)c1)O2]

or a pharmaceutically acceptable salt thereof.

17. The compound according to claim 1, wherein the compound is

18. The compound according to claim 1, wherein the compound is or a pharmaceutically acceptable salt thereof.

19. The compound according to claim 1, wherein the compound is

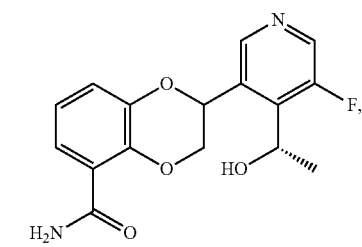 [SMILES: C[C@H](O)c1c(F)cncc1C1COc2c(cccc2C(N)=O)O1]

or a pharmaceutically acceptable salt thereof.

20. The compound according to claim 1, wherein the compound is

89

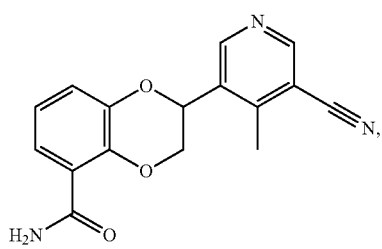

or a pharmaceutically acceptable salt thereof.

21. A pharmaceutical composition comprising the compound according to claim 15, or a pharmaceutically acceptable salt thereof, and at least one pharmaceutically acceptable carrier.

22. A pharmaceutical composition comprising the compound according to claim 16, or a pharmaceutically acceptable salt thereof, and at least one pharmaceutically acceptable carrier.

23. A pharmaceutical composition comprising the compound according to claim 17, or a pharmaceutically acceptable salt thereof, and at least one pharmaceutically acceptable carrier.

24. A pharmaceutical composition comprising the compound according to claim 18, or a pharmaceutically acceptable salt thereof, and at least one pharmaceutically acceptable carrier.

25. A pharmaceutical composition comprising the compound according to claim 19, or a pharmaceutically acceptable salt thereof, and at least one pharmaceutically acceptable carrier.

26. A pharmaceutical composition comprising the compound according to claim 20, or a pharmaceutically acceptable salt thereof, and at least one pharmaceutically acceptable carrier.

27. The method according to claim 11, wherein the compound of formula (I) is

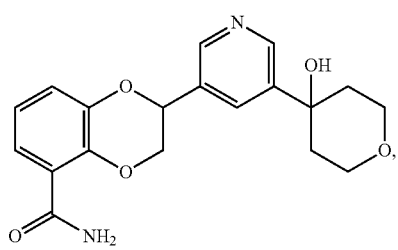 [SMILES: NC(=O)c1cccc2c1OCC(c1cncc(C3(O)CCOCC3)c1)O2]

or a pharmaceutically acceptable salt thereof.

28. The method according to claim 11, wherein the compound of formula (I) is

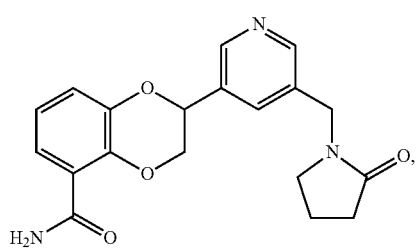 [SMILES: NC(=O)c1cccc2c1OCC(c1cncc(CN3CCCC3=O)c1)O2]

90 or a pharmaceutically acceptable salt thereof.

29. The method according to claim 11, wherein the compound of formula (I) is

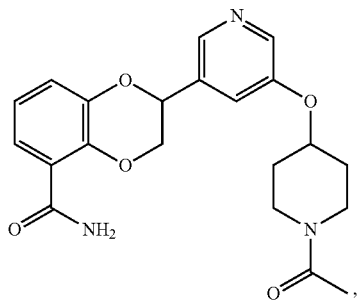 [SMILES: CC(=O)N1CCC(Oc2cncc(C3COc4c(cccc4C(N)=O)O3)c2)CC1]

or a pharmaceutically acceptable salt thereof.

30. The method according to claim 11, wherein the compound of formula (I) is

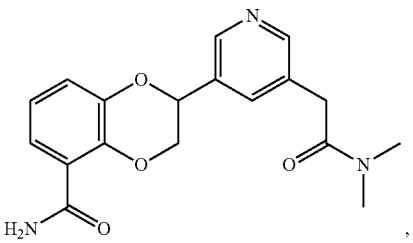 [SMILES: CN(C)C(=O)Cc1cncc(C2COc3c(cccc3C(N)=O)O2)c1]

or a pharmaceutically acceptable salt thereof.

31. The method according to claim 11, wherein the compound of formula (I) is

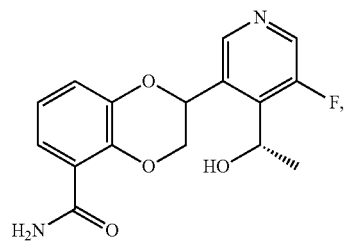 [SMILES: C[C@H](O)c1c(F)cncc1C1COc2c(cccc2C(N)=O)O1]

or a pharmaceutically acceptable salt thereof.

32. The method according to claim 11, wherein the compound of formula (I) is

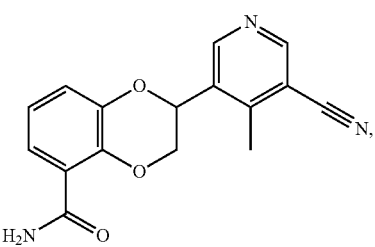

or a pharmaceutically acceptable salt thereof.

* * * * *